United States Patent
Giordani et al.

(10) Patent No.: US 9,162,979 B2
(45) Date of Patent: Oct. 20, 2015

(54) 1,5-DIARY1-2-ALKYLPYRROLE-3-SUBSTITUTED NITRO ESTERS, SELECTIVE COX-2 INHIBITORS AND NITRIC OXIDE DONORS

(75) Inventors: Antonio Giordani, Pavia (IT); Mariangela Biava, Rome (IT); Maurizio Anzini, Pianella/Castelnuovo Berardenga (IT); Vincenzo Calderone, Massa (IT); Lucio Claudio Rovati, Monza (IT)

(73) Assignee: ROTTAPHARM BIOTECH S.R.L., Monza (IT)

( * ) Notice: Subject to any disclaimer, the term of this patent is extended or adjusted under 35 U.S.C. 154(b) by 0 days.

(21) Appl. No.: 13/820,533

(22) PCT Filed: Sep. 7, 2011

(86) PCT No.: PCT/IB2011/053914
§ 371 (c)(1),
(2), (4) Date: Mar. 4, 2013

(87) PCT Pub. No.: WO2012/032479
PCT Pub. Date: Mar. 15, 2012

(65) Prior Publication Data
US 2013/0165494 A1 Jun. 27, 2013

(30) Foreign Application Priority Data
Sep. 7, 2010 (IT) .............................. TO2010A0739

(51) Int. Cl.
| | | |
|---|---|---|
| *A61K 31/40* | (2006.01) | |
| *A01N 43/36* | (2006.01) | |
| *C07D 207/337* | (2006.01) | |
| *A61K 45/00* | (2006.01) | |
| *C07D 207/333* | (2006.01) | |
| *C07D 207/335* | (2006.01) | |

(52) U.S. Cl.
CPC ............ *C07D 207/337* (2013.01); *A61K 31/40* (2013.01); *A61K 45/00* (2013.01); *C07D 207/333* (2013.01); *C07D 207/335* (2013.01)

(58) Field of Classification Search
None
See application file for complete search history.

(56) References Cited

FOREIGN PATENT DOCUMENTS

| WO | 9412463 A1 | 6/1994 |
| WO | 9509831 A1 | 4/1995 |
| WO | 0145703 A1 | 6/2001 |
| WO | 2005070883 A1 | 8/2005 |
| WO | 2008014821 A1 | 2/2008 |
| WO | 2008132025 A1 | 11/2008 |

OTHER PUBLICATIONS

Jean-Michel Dogne', Claudiu T. Supuran, Domenico Pratico, Adverse Cardiovascular Effects of the Coxibs, Journal of Medicinal Chemistry, Apr. 7, 2005.
Ghenet K. Hagos, Robert E. Carroll, Tatiana Kouznetsova, et al., Colon cancer chemoprevention by a novel NO chimera that shows anti-inflammatory and antiproliferative activity in vitro and in vivo, Molecular Cancer Therapeutics, 2007, pp. 2230-2239.
Hermann Stetter, Karl-Heinrich Mohrmann, Walter Schlenker, Addition von Aldehyden an aktivierte Doppelbindungen, XXVII1) Herstellung und Reaktionen von Alkoxy- und acetoxy-2,5-diketonen, Chemische Berichte, 1981, pp. 581-596.
R. Koster, M. Anderson, E.J. De Beer, Acetic acid for analgesic screening, Fed. Proc., 1959, p. 412.

(Continued)

*Primary Examiner* — Jeffrey S Lundgren
*Assistant Examiner* — Stephanie Springer
(74) *Attorney, Agent, or Firm* — Robert E. Alderson, Jr.

(57) ABSTRACT

1,5-diaryl-2-alkylpyrrole-3-substituted nitro esters, of Formula (I)

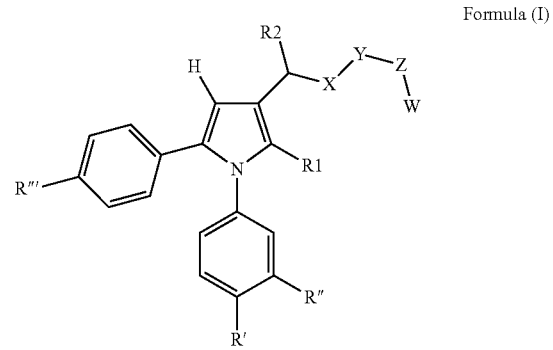

Formula (I)

are provided. Such compounds are potent and selective COX-2 inhibitors which are able to release NO in concentrations that make it possible to counteract the side effects due to selective COX-2 inhibition, without giving rise to hypotensive effects. Formula (I) includes compounds wherein the groups R' and R" are: —H, —F, —Cl, —Br, —CH$_3$, —CF$_3$, —OCH$_3$, —SCH$_3$, R1 is methyl, ethyl, trifluoromethyl, hydroxymethyl, methoxymethyl and the substituent in position –3 of the pyrrole ring is a chain, where the groups X, Y, Z, W and R2 are: X is a carbonyl or a group —(CHR$_3$)—, Y is an oxygen atom or the group —NR$_3$— and Z is a carbonyl or a group —(CHR$_3$)—, or a [—CH(COOH)—] group, or a group —(NR$_3$)—, W is an aliphatic chain substituted with one or two (—O—NO$_2$) groups, R2 is: —H, —OH, —OCH$_3$, or —NHR$_3$. R$_3$ is: —H, —CH$_3$, —CH$_2$CH$_3$, [—CH$_2$(CH$_3$)$_2$]. R''' is methylsulphonyl or sulphonamido. Pharmaceutical formulations and methods of making an using such formulations are also provided.

13 Claims, 2 Drawing Sheets

(56) References Cited

OTHER PUBLICATIONS

G.E. Leighton, R.E. Rodriguez, R.G. Hill, J. Hughes, κ-Opioid agonists produce antinociception after i.v. and i.c.v. but not intrathecal administration in the rat, Br. J. Pharmacol., 1988, pp. 553-560.

Thomas Klein, Manfrid Eltze, Thomas Grebe, Armin Hatzelmann, Martin Koemhoff, Celecoxib dilates guinea-pig coronaries and rat aortic rings and amplifies NO/cGMP signaling by PDE5 inhibition, Cardiovascular Research, 2007, pp. 390-397.

A. Martelli, S. Rapposelli, V. Calderone, NO-Releasing Hybrids of Cardiovascular Drugs, Current Medicinal Chemistry, 2006, pp. 609-625.

Carlos Velazquez, P.N. Praveen Rao, Robert McDonald, Edward E. Knaus, Synthesis and biological evaluation of 3,4-diphenyl-1,2,5-oxadiazole-2-oxides and 3,4-diphenyl-1,2,5-oxadiazoles as potential hybrid COX-2 inhibitor/nitric oxide donor agents, Bioorganic & Medicinal Chemistry, 2005, pp. 2749-2757.

Benjamin Bonavida, Stavroula Baritaki, Sara Huerta-Yepez, Mario I. Vega, Devasis Chatterjee, Kam Yeung, Novel therapeutic applications of nitric oxide donors in cancer: Roles in chemo-and immunosensitization to apoptosis and inhibition of metastases, Nitric Oxide, 2008, pp. 152-157.

Konstantin Chegaev, Loretta Lazzarato, Paolo Tosco, Clara Cena, Elisabetta Marini, Barbara Rolando, Pierre-Alain Carrupt, Roberta Fruttero, Alberto Gasco, NO-Donor COX-2 Inhibitors. New Nitrooxy-Substituted 1,5-Diarylimidazoles Endowed with COX-2 Inhibitory and Vasodilator Properties, J. Med. Chem., 2007, pp. 1449-1457.

Keith S. McCallum, William D. Emmons, The Dissociation Constants and Infrared Spectra of Some Nitratoacids, J. Org. Chem., Nov. 1955, p. 367.

James F. Kerwin, Jr., Jack R. Lancaster, Jr., Paul L. Feldman, Nitric Oxide: A New Paradigm for Second Messengers, Journal of Medicinal Chemistry, Oct. 27, 1995, p. 4343-4362.

Ish K. Khanna, Yi Yu, Renee M. Huff, Richard M. Weier, Xiangdong Xu, Francis J. Koszyk, Paul W. Collins, J. Nita Cogburn, Peter C. Isakson, Carol M. Koboldt, Jaime L. Masferrer, William E. Perkins, Karen Seibert, Amy W. Veenhuizen, Jinhua Yuan, Dai-Chan Yang, Yan Y. Zhang, Selective Cyclooxygenase-2 Inhibitors: Heteroaryl Modified 1,2-Diarylimidazoles Are Potent, Orally Active Antiinflammatory Agents, J. Med. Chem., 2000, pp. 3168-3185.

Isla S Mackenzie, Daniel Rutherford, Thomas M MacDonald, Nitric oxide and cardiovascular effects: new insights in the role of nitric oxide for the management of osteoarthritis, Arthritis Research & Therapy, 2008.

Nengtai Ouyang, Jennie L. Williams, George J. Tsioulias, Jianjun Gao, Michael J. Iatropoulos, Levy Kopelovich, Khosrow Kashfi, Basil Rigas, Nitric Oxide-Donating Aspirin Prevents Pancreatic Cancer in a Hamster Tumor Model, Cancer Res, 2006, pp. 4503-4511.

Wei-Chuan Chen, Matthew D. Vera, Madeleine M. Joullie', Mild, Selective Cleavage of Amino Acid and Peptide β-(Trimethylsilyl)ethoxymethyl (SEM) Esters by Magnesium Bromide, Tetrahedron Letters, 1997, pp. 4025-4028.

Masato Tsutsui, Sei Nakata, Hiroaki Shimokawa, Yutaka Otsuji, Nobuyuki Yanagihara, Spontaneous Myocardial Infarction and Nitric Oxide Synthase, Trends Card. Med., 2008, pp. 275-279.

Maurizio Anzini, Michele Rovini, Andrea Cappelli, Salvatore Vomero, Fabrizio Manetti, Maurizio Botta, Lidia Sautebin, Antonietta Rossi, Carlo Pergola, Carla Ghelardini, Monica Norcini, Antonio Giordani, Francesco Makovec, Paola Anzellotti, Paola Patrignani, Mariangela Biava, Synthesis, Biological Evaluation, and Enzyme Docking Simulations of 1,5-Diarylpirrole-3-Alkoxyethyl Ethers as Selective Cyclooxygenase-2-Inhibitors Endowed with Anti-inflammatory and Antinociceptive, J.Med.Chem. 2008, vol. 51, No. 15, pp. 4476-4481.

Nicolas Beziere, Laurence Goossens, Jean Pommery, Herve' Vezin, Nadia Touati, Jean-Pierre Henichart, Nicole Pommery, New NSAIDs-NO hybrid molecules with antiproliferative properties on human prostatic cancer cell lines, Bioorganic & Medicinal Chemistry Letters, 2008, pp. 4655-4657.

Mariangela Biava, Giulio C. Porretta, Giovanna Poce, Sibilla Supino, Fabrizio Manetti, Stefano Forli, Maurizio Botta, Lidia Sautebin, Antonietta Rossi, Carlo Pergola, Carla Ghelardini, Monica Norcini, Francesco Makovec, Antonio Giordani, Paola Anzellotti, Roberto Cirilli, Rosella Ferretti, Bruno Gallinella, Francesco La Torre, Maurizio Anzini, Paola Patrignani, Synthesis, in vitro, and in vivo biological evaluation and molecular docking simulations of chiral, Bioorg.Med.Chem. 2008, vol. 16, pp. 8072-8081.

Mariangela Biava, Giulio Cesare Porretta, Andrea Cappelli, Salvatore Vomero, Fabrizio Manetti, Maurizio Botta, Lidia Sautebin, Antonietta Rossi, Francesco Makovec, Maurizio Anzini, 1,5-Diarylpyrrole-3-acetic Acids and Esters as Novel Classes of Potent and Highly Selective Cyclooxygenase-2-Inhibitors, J. Med. Chem., 2005, pp. 3428-3432.

John L. Wallace, Serena Viappiani, Manlio Bolla, Cyclooxygenase-inhibiting nitric oxide donators for osteoarthritis, Trends Pharm. Sci., 2009, pp. 112-117.

1,5-DIARY1-2-ALKYLPYRROLE-3-SUBSTITUTED NITRO ESTERS, SELECTIVE COX-2 INHIBITORS AND NITRIC OXIDE DONORS

CROSS-REFERENCE TO RELATED APPLICATIONS

This application is a National Phase Application of PCT International Application No. PCT/IB2011/053914, International Filing Date, Sep. 7, 2011, claiming priority to Italian Patent Application No. TO2010A000739, filed Sep. 7, 2010, both of which are hereby incorporated by reference in their entirety.

FIELD OF THE INVENTION

The present invention relates to 1,5-diaryl-2-alkylpyrrole-3-substituted nitro esters, of formula (I), which are potent, selective COX-2 inhibitors able to release nitric oxide in concentrations that can counteract the side effects due to selective COX-2 inhibition, without giving rise to hypotensive effects. The purpose of the invention includes: preparation of the compounds of formula (I), the respective pharmaceutical formulations and use thereof for treating acute and chronic pain, for treating inflammatory disorders and for drug treatment of some forms of tumours.

BACKGROUND OF THE INVENTION

The non-steroidal anti-inflammatory drugs (NSAIDs) represent a class that is widely used in the treatment of various disorders. To date, treatment with NSAIDs is the best available therapy for pain caused by rheumatoid arthritis (RA) and osteoarthritis (OA), and other examples of common applications are treatment of fibromyalgia, of intestinal inflammation, inflammation of the urogenital tract and of the respiratory system, treatment of dysmenorrhoea and treatment of lupus erythematosus. Although the analgesic action of NSAIDs does not match in potency that of the opiates, their co-administration with usual narcotics has found wide application both for the treatment of postoperative pain and of chronic pain induced by various pathologies including tumoral pathologies. NSAIDs perform their anti-inflammatory and analgesic action via inhibition of cyclooxygenase (COX). At least two isoforms of COX are known: COX-1, expressed constitutively, and COX-2, which is absent from most tissues in physiological conditions and is expressed as a result of pro-inflammatory stimuli (e.g.: cytokines). As the traditional anti-inflammatories (tNSAIDs) are not selective, they inhibit both isoforms often with a preference for COX-1. This poor selectivity leads, with concomitant inhibition of COX-1, to inhibition of synthesis of prostanoids that are essential for maintenance of the functions of the gastric mucosa and of renal homeostasis, giving rise, especially in prolonged use, to severe gastrointestinal (GI) and renal complications. Inhibition of COX-1 by tNSAIDs leads initially to a decrease in thickness of the mucosa (erosion) and then to lesions (ulcer). At the renal level tNSAIDs are known to cause reduced glomerular filtration that gives rise to nephritides and, in particularly sensitive patients, to ischaemia and renal blockade. Clinical use of selective COX-2 inhibitors (Coxibs) has recently shown that the gastric toxicity associated with the use of tNSAIDs can be reduced considerably. Several recent clinical studies have shown that selective COX-2 inhibition, as well as giving rise to anti-inflammatories and analgesics with a safer GI profile, proves effective in the treatment of various precancerous and cancerous forms. In fact, COX-2 is overexpressed in gastric, hepatic, pancreatic, oesophageal, colon, breast, bladder, and lung tumours. However, various clinical and epidemiological studies have shown that long-term use of selective COX-2 inhibitors is associated with a higher incidence of adverse effects relating to the cardiovascular system, and in particular with an increased incidence of myocardial infarction, angina pectoris and transient ischaemic attacks. The cause of this toxicity for the cardiovascular system, which is also found with some tNSAIDs that are rather selective in inhibiting COX-2, arises from the fact that this isoform, constitutively expressed in the vascular epithelium, is fundamental to the synthesis of prostaglandin $PGI_2$, a potent vasodilator (J. M. Dogné et al., J. Med. Chem., 2005, 48, 2251-2257). Thus, high selectivity in inhibition of COX-2 leads, in the cardiovascular system, to prevalence of the pro-aggregative and vasoconstrictive stimulus exerted by thromboxane ($TxA_2$) no longer counterbalanced by the vasodilator effect of $PGI_2$. The side effects associated with the use of tNSAIDs and those relating to the use of Coxibs create the need for new analgesics and anti-inflammatories that have a better profile of tolerability.

Similarly to prostacyclin ($PGI_2$), nitric oxide (NO) at low concentrations has an important role in maintaining appropriate functionality of the cardiovascular system (J. F. Kervin et al., J. Med. Chem., 1995, 38, 4343-4362). Although the potent vasodilator effect of organic nitrates has been known for a long time, it was only discovered at the end of the 1970s that NO (Endothelium Derived Relaxing Factor, EDRF) is one of the mediators released by the vascular endothelium to control vasodilation, thrombosis, permeability and angiogenesis. NO gives rise, through activation of guanylate cyclase, to an increase in cGMP, which leads to vasodilation in smooth muscles, inhibits adhesion of leukocytes to the vessel wall and inhibits platelet aggregation, giving rise to an overall anti-thrombotic action.

It is also known that NO is of fundamental importance in maintaining good cardiac functionality and that gene knockout experiments relating to the genes held to be responsible for expression of the enzymes capable of forming NO leads to spontaneous myocardial infarction (M. Tsutsui et al., Trends Cardiovasc. Med., 2008, 18, 8, 275-79). In the body, NO is synthesized by an enzyme known as nitric-oxide synthase (NOS), of which three isoforms are known: epithelial (eNOS), neuronal (nNOS) and inducible (iNOS). It is well known that appropriate derivatives of nitric acid (organic nitrates) as well as other organic compounds such as nitrosothiols and 1,2,5-oxadiazoles-2-oxide (furoxane N-oxide) are able to release NO of "exogenous" origin, so as to be utilizable in the treatment of cardiovascular pathologies (A. Martelli et al., Curr. Med. Chem. 2006, 13, 6, 609-25). The synthesis of molecules capable of selectively inhibiting COX-2 and at the same time of releasing NO appropriately, can give rise to new anti-inflammatory and analgesic drugs, without the cardiovascular and renal side effects that characterized the Coxibs. Some COX inhibitors that are donors of NO (CINOD: COX Inhibitors Nitric Oxide Donors) are known, for example naproxcinod (WO 9509831) and NO-flurbiprofen (WO 94012463). Although, for these products, complete absence of adverse events in the cardiovascular and renal area was recently claimed (WO 2008/132025), these compounds were designed more for overcoming the effects of gastric toxicity known for the COX-1 inhibitors than for the effects of cardiovascular and renal toxicity connected with inhibition of COX-2. In fact, protective effects exerted by NO are also known in the GI system, such as modulation of blood flow, control of permeability of the epithelium, secretion of mucus and of bicarbonate and capacity for improving the properties of self-repair in the damaged mucosa (J. L. Wallace et al., Trends Pharm. Sci., 2009, 30, 112-117). Selective COX-2 inhibitors that are at the same time NO donors have been reported, for example for rofecoxib (WO 2005/070883) or for cimicoxib (K. Chegaev et al., J. Med. Chem., 2007, 50, 1449-1457) as well as for other heterocyclic COX-2 inhibitors (C. Velazquez et al., Bioorg. & Med. Chem., 2005, 2749-2757). WO 2008/014821 describes inhibitors that are selective for COX-2, which have favourable pharmacokinetic and pharmacodynamic properties, which are reflected in excellent pharmacological properties. The possibility of combining, in these inhibitors, a function of being able to release NO appropriately, at the same time maintaining adequate activity in inhibition of COX-2, would give rise to new anti-inflammatory and analgesic drugs characterized by absence of the cardiovascular and renal effects typical of the selective COX-2 inhibitors, and would make it possible to improve their GI profile. Moreover, it should be borne in mind that although NO at high concentrations (such as the micromolar concentrations produced by iNOS) has deleterious effects on the cartilage in disorders such as OA and RA, at low concentrations (such as the nanomolar/picomolar concentrations produced by cNOS) NO has an anti-apoptotic and protective effect for the chondrocytes. Moreover, it is known that low concentrations of NO can have an important role in increasing blood flow, improving the supply of nutrients and oxygen to the synovia and to the subchondral bone. As well as the role of NO in the control of pain, via activation of cGMP in the nerve cells which, leading to hyperpolarization, consequently gives rise to blocking of pain transmission. These synergistic effects with inhibition of COX-2, exerted by release of small amounts of NO, are not only useful in the treatment of disorders such as OA and RA (I. S. Mackenzie et al., Arthritis Research & Therapy, 2008, 10: S3) but also in the treatment of various types of tumours (B. Bonavida et al., Nitric Oxide, 2008, 152-157). In fact, it was recently shown that NO-donors can inhibit the capacity of some types of tumours to metastasize as well as being able to restore apoptosis, making the tumour cell sensitive to chemotherapy. The role of nitro-aspirin (NO-ASA) in inhibiting the development of pancreatic tumour was described recently (N. Ouyang et al., Cancer Res., 2006, 66:8, 4503), as well as the efficacy of other CINODs in the treatment of colon tumour (G. K. Hagos et al., Mol. Cancer Ther., 2007, 2230-39) and prostate cancer (N. Beziere et al., Bioorganic & Med. Chem. Lett, 2008, 4655-57).

SUMMARY OF THE INVENTION

The present invention relates to compounds represented by the following Formula (I):

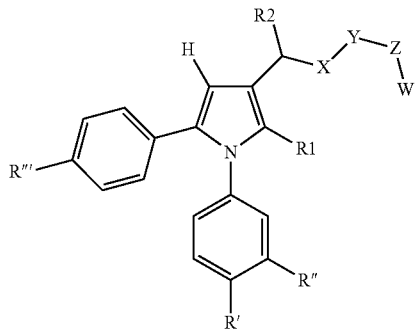

Formula (I)

Where:
the substituent in position −1 of the pyrrole ring is a phenyl, substituted in the meta and para positions with groups R' and R" selected independently from: hydrogen (—H), fluorine (—F), chlorine (—Cl), bromine (—Br), methyl (—$CH_3$), trifluoromethyl (—$CF_3$), methoxy (—$OCH_3$), thiomethyl (—$SCH_3$);

the substituent R1 is selected independently from the following groups: methyl (—$CH_3$), ethyl (—$C_2H_5$), trifluoromethyl (—$CF_3$), hydroxymethyl (—$CH_2OH$), methoxymethyl (—$CH_2OCH_3$);

the substituent in position −3 of the pyrrole ring is a chain, where the groups X, Y, Z, W and R2 have the following meanings:

X is selected from the groups: carbonyl —(C=O)—, methylene/methine —($CHR_3$)— where $R_3$ is as defined hereunder;

Y is selected from an oxygen atom (—O—) or the group —$NR_3$— where $R_3$ is as defined hereunder;

Z is selected from a carbonyl —(C=O)—, a methylene/methine group —($CHR_3$)—, a [—CH(COOH)—] group, or an —($NR_3$)— group where $R_3$ is as defined hereunder;

W is a saturated aliphatic chain with 1 to 3 carbon atoms, linear or branched, substituted with one or two nitro ester groups (—O—$NO_2$);

R2 is selected independently from the groups: hydrogen (—H), hydroxyl (—OH), methoxy (—$OCH_3$), or amino (—$NHR_3$);

The group $R_3$ is selected independently from: hydrogen (—H), methyl (—$CH_3$), ethyl (—$CH_2CH_3$), isopropyl [—$CH_2(CH_3)_2$];

the group R'" is selected independently from: methylsulphonyl (—$SO_2Me$) and sulphonamido (—$SO_2NH_2$);

provided that:
when X is a C=O group and Y is an oxygen atom (—O—), Z is not a carbonyl group (C=O);
when X is a methylene/methine group —($CHR_3$)—Y is not a methylene/methine group —($CHR_3$)—;

the methylene/methine group [—$CH(R_3)$—] is a group represented by a carbon atom forming part of the chain, where the other two substituents can either be two hydrogen atoms ($R_3$=H), in which case said group is a methylene (—$CH_2$—), or are respectively a hydrogen atom and an alkyl group selected from: methyl, ethyl, isopropyl, in which case said group is a methine —($CHR_3$)—, $R_3$=methyl, ethyl, isopropyl;

the [—CH(COOH)—] group is a group represented by a carbon atom forming part of the chain, whose other two substituents are respectively a hydrogen atom and a carboxylate (—COOH).

Bearing in mind the meanings of X, Y and Z, in some cases the compounds of formula (I) can be chiral, and thus exist either as single enantiomers of configuration S or R, or as mixtures thereof including the racemic mixture (1:1). Enantiomers also exist when the chain W is branched, i.e. when at least one non-terminal group —$ONO_2$ is present in said chain.

The present invention also relates to single enantiomers of the compounds of formula (I) in the (R) or (S) form, the respective racemic mixtures and mixtures enriched with said enantiomers. When the compound of formula (I) has two or more chiral centres, several diastereomers are possible. The present invention also relates to diastereomers of the compounds of formula (I) where every chiral centre can be independently in the (R) or (S) configuration, the respective diastereomeric mixtures (1:1) or enriched mixtures.

DETAILED DESCRIPTION

Figure 1:
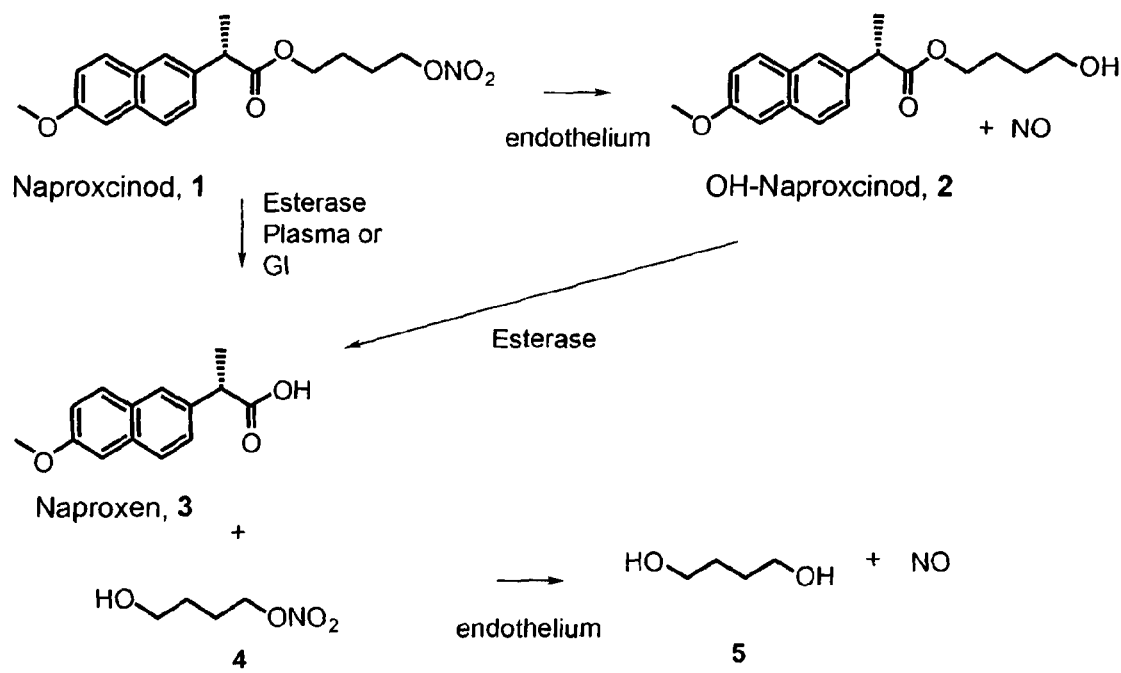
FIG. 1 schematically shows the two routes through which naproxcinod can release NO.

The compounds of Formula (I) can, depending on the meanings of the substituents X, Y and Z of the chain in position −3 of the pyrrole ring, be divided into groups according to the functional groups present, namely:

Compounds of Formula I-a:
when, in the compounds of Formula (I), group X is a carbonyl —(C=O)— and group Y is an oxygen atom (—O—), the compounds of Formula (I) are esters of formula (I-a):

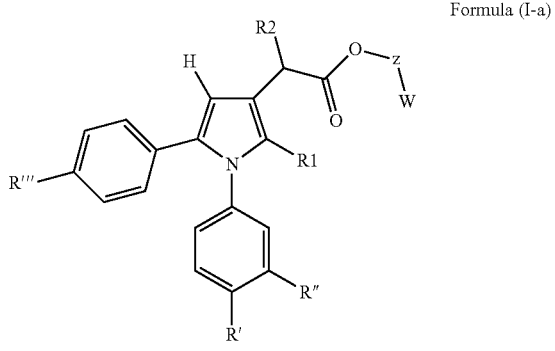

Formula (I-a)

In this case group Z is a methylene group or a methine group and the other substituents have the meaning defined for the compounds of Formula (I).

Representative examples of compounds of formula (I-a) are:
2-(nitrooxy)ethyl-2-[1-phenyl-2-methyl-5-(4-methylsulphonylphenyl)-1H-pyrrol-3-yl]acetate Example 1

2-(nitrooxy)ethyl-2-[(1-(4-fluorophenyl)-2-methyl-5-(4-(methylsulphonyl)phenyl)-1H-pyrrol-3-yl)]acetate Example 2

2-(nitrooxy)ethyl-2-[(1-(3-fluorophenyl)-2-methyl-5-(4-methanesulphonylphenyl)-1H-pyrrol-3-yl)acetate]

Example 3

2-(nitrooxy)ethyl-2-[1-(4-methoxyphenyl)-2-methyl-5-(4-methylsulphonylphenyl)-1H-pyrrol-3-yl]-acetate Example 4

2-(nitrooxy)ethyl-2-[1-(4-methylthiophenyl)-2-methyl-5-(4-methylsulphonylphenyl)-1H-pyrrol-3-yl]-acetate Example 5

3-(nitrooxy)propyl-2-[1-phenyl-2-methyl-5-(4-methylsulphonylphenyl)-1H-pyrrol-3-yl-acetate Example 6

3-(nitrooxy)propyl-2-[1-(4-fluorophenyl)-2-methyl-5-(4-methylsulphonylphenyl)-1H-pyrrol-3-yl]-acetate Example 7

3-(nitrooxy)propyl-2-[1-(3-fluorophenyl)-2-methyl-5-(4-methylsulphonylphenyl)-1H-pyrrol-3-yl]-acetate Example 8

3-(nitrooxy)propyl-2-[1-(4-methoxyphenyl)-2-methyl-5-(4-methylsulphonylphenyl)-1H-pyrrol-3-yl]-acetate Example 9

3-(nitrooxy)propyl-2-[1-(4-methylthiophenyl)-2-methyl-5-(4-methylsulphonylphenyl)-1H-pyrrol-3-yl]-acetate Example 10

4-(nitrooxy)butyl-2-[1-(4-fluorophenyl)-2-methyl-5-(4-methylsulphonylphenyl)-1H-pyrrol-3-yl]-acetate Example 11

4-(nitrooxy)butyl-2-[1-(3-fluorophenyl)-2-methyl-5-(4-methylsulphonylphenyl)-1H-pyrrol-3-yl]-acetate Example 12

4-(nitrooxy)butyl-2-[1-(4-methoxyphenyl)-2-methyl-5-(4-methylsulphonylphenyl)-1H-pyrrol-3-yl]-3-acetate Example 13

4-(nitrooxy)butyl-2-[1-(4-methylthiophenyl)-2-methyl-5-(4-methylsulphonylphenyl)-1H-pyrrol-3-yl]-acetate Example 14

(R,S)-2,3-bis(nitrooxy)propyl-2-[1-phenyl-2-methyl-5-(4-methylsulphonylphenyl)-1H-pyrrol-3-yl]-acetate Example 15

Representative examples of compounds of formula (I-a) where R2 is amino (—NH$_2$) are:
(R,S)-2-(nitrooxy)ethyl-[2-amino-2-[1-(4-fluorophenyl)-2-methyl-5-(4-methylsulphonylphenyl)-1H-pyrrol-3-yl]]-acetate Example 16

(R,S)-2-(nitrooxy)ethyl-[2-amino-2-[1-(3-fluorophenyl)-2-methyl-5-(4-methylsulphonylphenyl)-1H-pyrrol-3-yl]]-acetate Example 17

(R,S)-3-(nitrooxy)propyl-[2-amino-2-[1-(4-fluorophenyl)-2-methyl-5-(4-methylsulphonylphenyl)-1H-pyrrol-3-yl]]-acetate

Example 18

(R,S)-3-(nitrooxy)propyl-[2-amino-2-[1-(3-fluorophenyl)-2-methyl-5-(4-methylsulphonylphenyl)-1H-pyrrol-3-yl]]-acetate

Example 19

(R,S)-2-(nitrooxy)butyl-[2-amino-2-[1-(4-fluorophenyl)-2-methyl-5-(4-methylsulphonylphenyl)-1H-pyrrol-3-yl]]-acetate

Example 20

(R,S)-2-(nitrooxy)butyl-[2-amino-2-[1-(3-fluorophenyl)-2-methyl-5-(4-methylsulphonylphenyl)-1H-pyrrol-3-yl]]-acetate

Example 21

The structures relating to the representative examples of the compounds of formula (I-a) listed above are shown in Table 1.

TABLE 1

Representative examples of Compounds of Formula (I-a):

| Example | Structure | Empirical formula | MW |
|---|---|---|---|
| Example 1 | 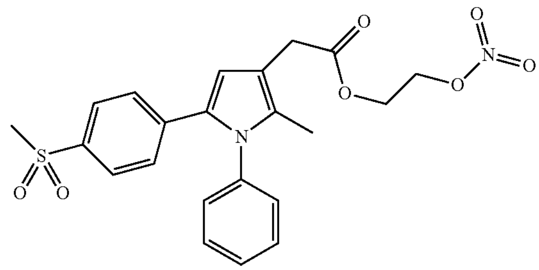 [SMILES: Cc1c(CC(=O)OCCO[N+](=O)[O-])cc(-c2ccc(S(C)(=O)=O)cc2)n1-c1ccccc1] | $C_{22}H_{22}N_2O_7S$ | 458.49 |
| Example 2 | 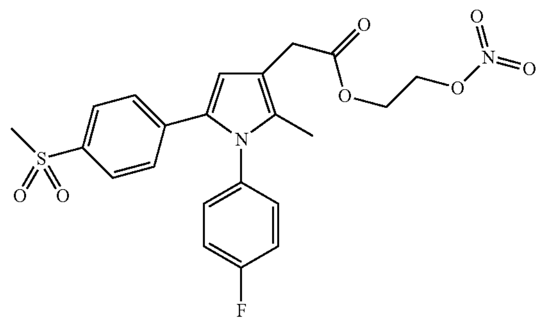 [SMILES: Cc1c(CC(=O)OCCO[N+](=O)[O-])cc(-c2ccc(S(C)(=O)=O)cc2)n1-c1ccc(F)cc1] | $C_{22}H_{21}FN_2O_7S$ | 476.48 |
| Example 3 | 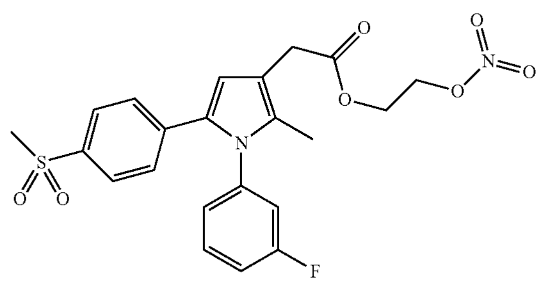 [SMILES: Cc1c(CC(=O)OCCO[N+](=O)[O-])cc(-c2ccc(S(C)(=O)=O)cc2)n1-c1cccc(F)c1] | $C_{22}H_{21}FN_2O_7S$ | 476.48 |
| Example 4 | 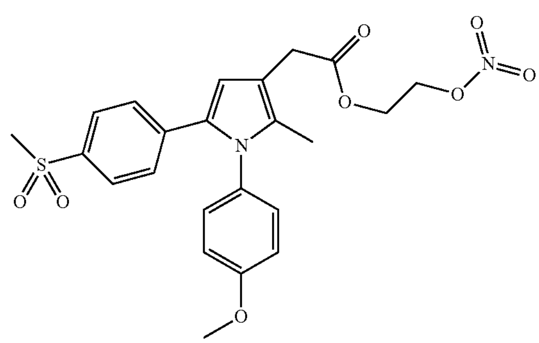 [SMILES: COc1ccc(-n2c(-c3ccc(S(C)(=O)=O)cc3)cc(CC(=O)OCCO[N+](=O)[O-])c2C)cc1] | $C_{23}H_{24}N_2O_8S$ | 488.52 |

TABLE 1-continued

Representative examples of Compounds of Formula (I-a):

| Example | Structure | Empirical formula | MW |
|---|---|---|---|
| Example 5 | 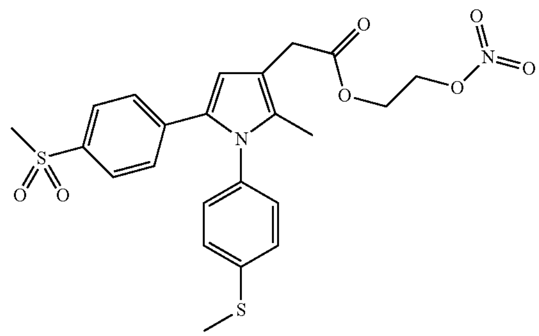 [SMILES: CSc1ccc(-n2c(-c3ccc(S(C)(=O)=O)cc3)cc(CC(=O)OCCO[N+](=O)[O-])c2C)cc1] | $C_{23}H_{24}N_2O_7S_2$ | 504.58 |
| Example 6 | 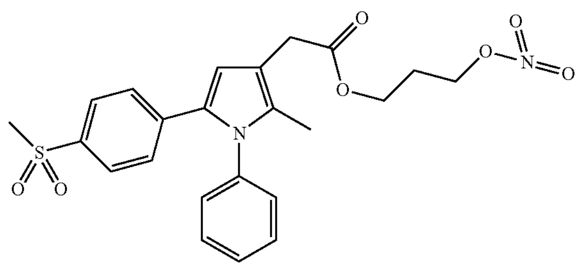 [SMILES: Cc1c(CC(=O)OCCCO[N+](=O)[O-])cc(-c2ccc(S(C)(=O)=O)cc2)n1-c1ccccc1] | $C_{23}H_{24}N_2O_7S$ | 472.52 |
| Example 7 | 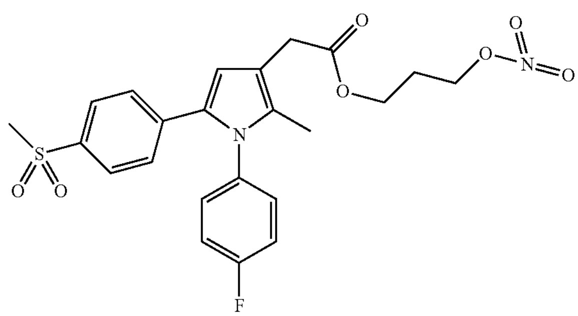 [SMILES: Cc1c(CC(=O)OCCCO[N+](=O)[O-])cc(-c2ccc(S(C)(=O)=O)cc2)n1-c1ccc(F)cc1] | $C_{23}H_{23}FN_2O_7S$ | 490.51 |
| Example 8 | 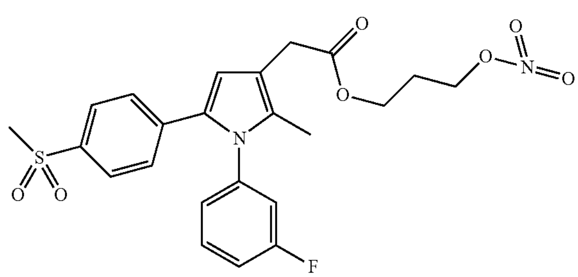 [SMILES: Cc1c(CC(=O)OCCCO[N+](=O)[O-])cc(-c2ccc(S(C)(=O)=O)cc2)n1-c1cccc(F)c1] | $C_{23}H_{23}FN_2O_7S$ | 490.51 |
| Example 9 | 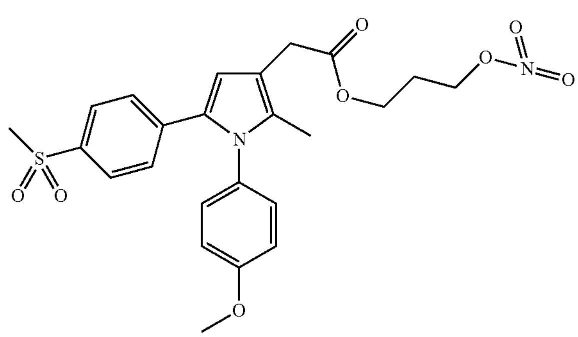 [SMILES: COc1ccc(-n2c(-c3ccc(S(C)(=O)=O)cc3)cc(CC(=O)OCCCO[N+](=O)[O-])c2C)cc1] | $C_{24}H_{26}N_2O_8S$ | 502.55 |

TABLE 1-continued
Representative examples of Compounds of Formula (I-a):
| Example | Structure | Empirical formula | MW |
|---|---|---|---|
| Example 10 | 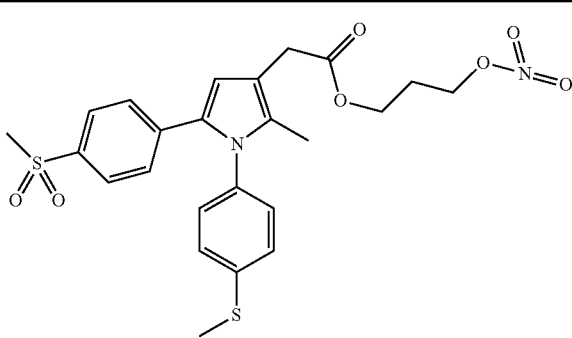 | $C_{24}H_{26}N_2O_7S_2$ | 518.61 |
| Example 11 | 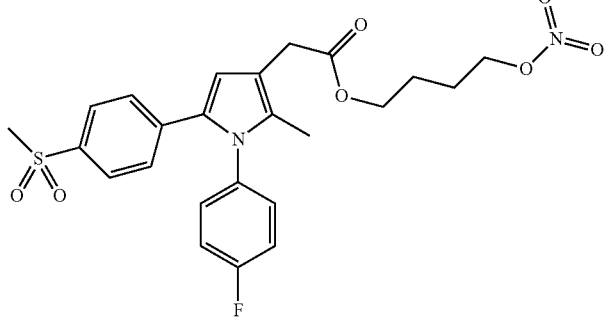 | $C_{24}H_{25}N_2O_7S_2$ | 504.54 |
| Example 12 | 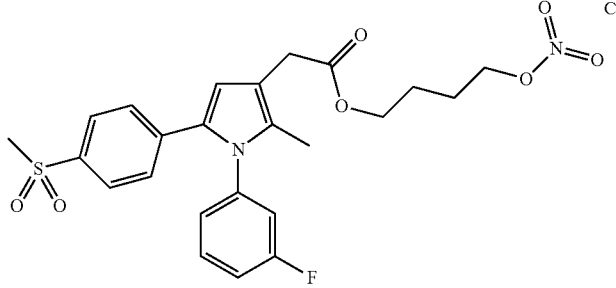 | $C_{24}H_{25}FN_2O_7S$ | 504.54 |
| Example 13 | 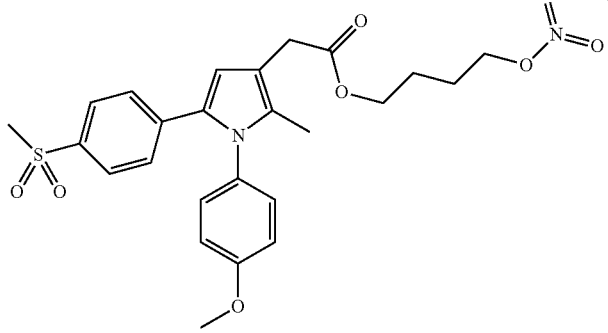 | $C_{25}H_{28}N_2O_8S$ | 516.57 |

TABLE 1-continued

Representative examples of Compounds of Formula (I-a):

| Example | Structure | Empirical formula | MW |
|---------|-----------|-------------------|-----|
| Example 14 | 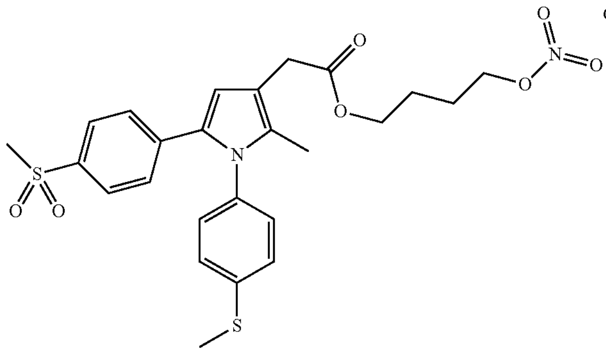 [SMILES: CSc1ccc(-n2c(-c3ccc(S(C)(=O)=O)cc3)cc(CC(=O)OCCCCO[N+](=O)[O-])c2C)cc1] | $C_{25}H_{28}N_2O_7S_2$ | 532.64 |
| Example 15 | 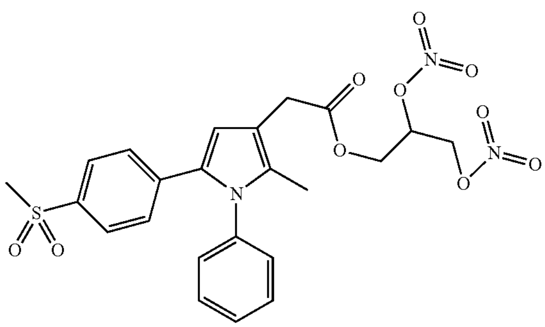 [SMILES: Cc1c(CC(=O)OCC(CO[N+](=O)[O-])O[N+](=O)[O-])cc(-c2ccc(S(C)(=O)=O)cc2)n1-c1ccccc1] | $C_{23}H_{23}N_3O_{10}S$ | 533.52 |
| Example 16 | 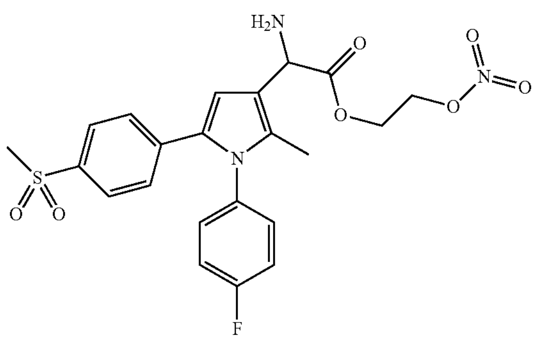 [SMILES: Cc1c(C(N)C(=O)OCCO[N+](=O)[O-])cc(-c2ccc(S(C)(=O)=O)cc2)n1-c1ccc(F)cc1] | $C_{22}H_{22}FN_3O_7S$ | 491.50 |
| Example 17 | 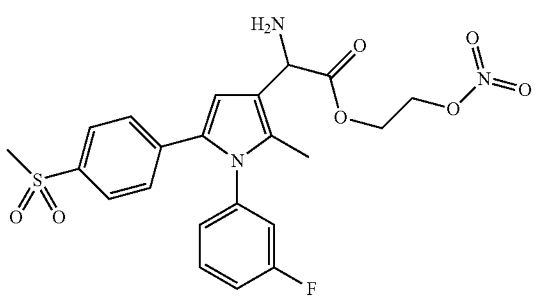 [SMILES: Cc1c(C(N)C(=O)OCCO[N+](=O)[O-])cc(-c2ccc(S(C)(=O)=O)cc2)n1-c1cccc(F)c1] | $C_{22}H_{22}FN_3O_7S$ | 491.50 |

TABLE 1-continued
Representative examples of Compounds of Formula (I-a):
| Example | Structure | Empirical formula | MW |
|---------|-----------|-------------------|-----|
| Example 18 | 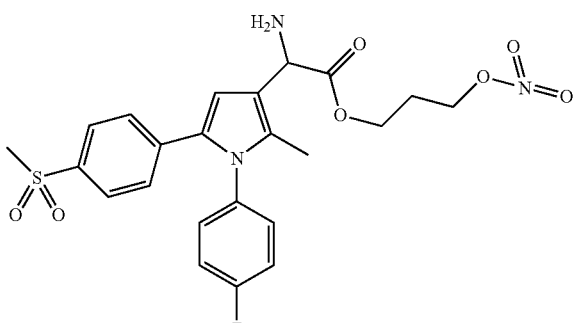 | C23H24FN3O7S | 505.53 |
| Example 19 | 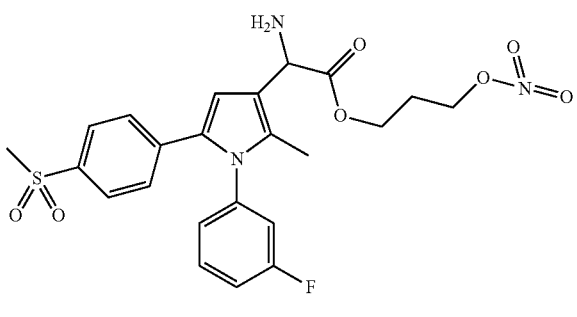 [SMILES: Cc1c(C(N)C(=O)OCCCO[N+](=O)[O-])cc(-c2ccc(S(C)(=O)=O)cc2)n1-c1cccc(F)c1] | C23H24FN3O7S | 505.53 |
| Example 20 | 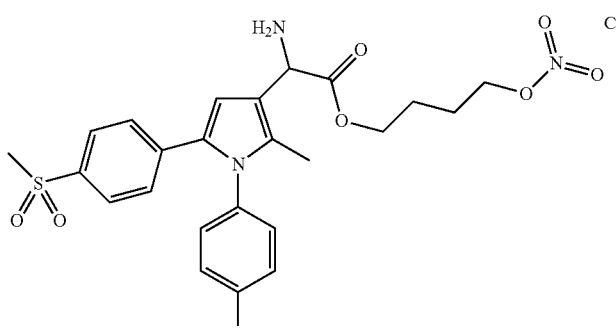 | C24H26FN3O7S | 519.55 |
| Example 21 | 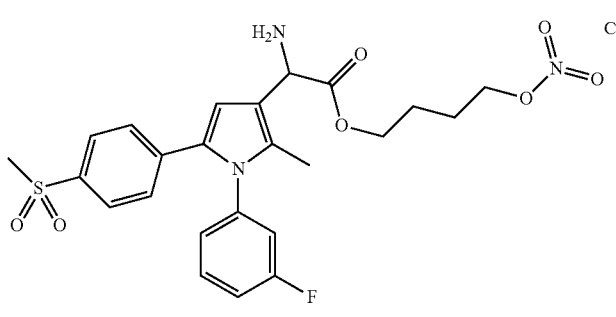 | C24H26FN3O7S | 519.55 |

Compounds of Formula I-b:
when, in the compounds of Formula (I), group X is a carbonyl —(C=O)— and group Y is an —NR$_3$ group, the compounds of Formula (I) are amides of formula (I-b):

Compounds of formula (I-b)

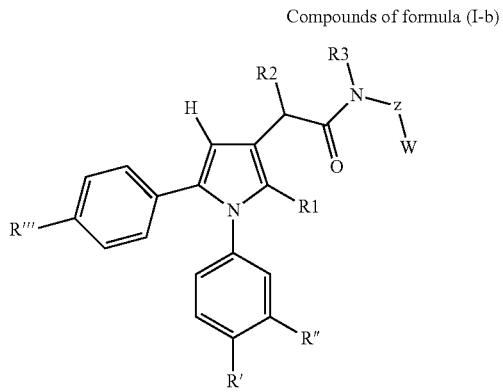

In this case group Z will be a methylene/methine group (—CHR$_3$), or a [—CH(COOH)—] group; where R$_3$, W and the other substituents are as defined for the compounds of Formula (I).

Representative examples of compounds of formula (I-b) where R2 is hydrogen are:
N-[(2-nitroxy)ethyl]-2-[1-phenyl-2-methyl-5-(4-methylsulphonylphenyl)-1H-pyrrol-3-yl]acetamide Example 22

N-[(2-nitroxy)ethyl]-2-[1-(4-fluorophenyl)-2-methyl-5-(4-methylsulphonylphenyl)-1H-pyrrol-3-yl]acetamide Example 23

N-[(2-nitroxy)ethyl]-2-[1-(3-fluorophenyl)-2-methyl-5-(4-methylsulphonylphenyl)-1H-pyrrol-3-yl]acetamide Example 24

N-[(3-nitroxy)propyl]-2-[1-phenyl-2-methyl-5-(4-methylsulphonylphenyl)-1H-pyrrol-3-yl]acetamide Example 25

N-[(3-nitroxy)propyl]-2-[1-(4-fluorophenyl)-2-methyl-5-(4-methylsulphonylphenyl)-1H-pyrrol-3-yl]acetamide Example 26

N-[(3-nitroxy)propyl]-2-[1-(3-fluorophenyl)-2-methyl-5-(4-methylsulphonylphenyl)-1H-pyrrol-3-yl]acetamide Example 27

Representative examples of compounds of formula (I-b) where R2 is hydrogen and Z is the —[CH(COOH)]— group are:
(S)-3-(nitroxy)-2-[[1-phenyl-2-methyl-5-(4-methylsulphonylphenyl)-1H-pyrrol-3-yl]acetamido]propanoic acid Example 28

(S)-3-(nitroxy)-2-[[1-(4-fluorophenyl)-2-methyl-5-(4-methylsulphonylphenyl)-1H-pyrrol-3-yl]acetamido]propanoic acid Example 29

(S)-3-(nitroxy)-2-[[1-(3-fluorophenyl)-2-methyl-5-(4-methylsulphonylphenyl)-1H-pyrrol-3-yl]acetamido]propanoic acid Example 30

(R,S)-4-(nitrooxy)-2-[[1-phenyl-2-methyl-5-(4-methylsulphonylphenyl)-1H-pyrrol-3-yl]acetamido]butanoic acid Example 31

(R,S)-4-(nitrooxy)-2-[[1-(4-fluorophenyl)-2-methyl-5-(4-methylsulphonylphenyl)-1H-pyrrol-3-yl]acetamido]butanoic acid Example 32

(R,S)-4-(nitrooxy)-2-[[1-(3-fluorophenyl)-2-methyl-5-(4-methylsulphonylphenyl)-1H-pyrrol-3-yl]acetamido]butanoic acid Example 33

Representative examples of compounds of formula (I-b) where R2 is amino are:
(R,S)-2-amino-N-(2-nitroxy)ethyl-2-[1-phenyl-2-methyl-5-(4-methylsulphonylphenyl)-1H-pyrrol-3-yl]acetamide Example 34

(R,S)-2-amino-N-(2-nitroxy)propyl-2-[1-phenyl-2-methyl-5-(4-methylsulphonylphenyl)-1H-pyrrol-3-yl]acetamide Example 35

The structures relating to the representative examples of the compounds of formula (I-b) listed above are shown in Table 2.

TABLE 2

Representative examples of Compounds of Formula (I-b):

| Example | Structure | Empirical formula | MW |
|---|---|---|---|
| Example 22 | 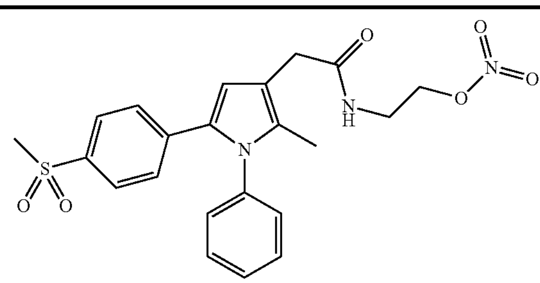 | $C_{22}H_{23}N_3O_6S$ | 457.51 |

TABLE 2-continued

Representative examples of Compounds of Formula (I-b):

| Example | Structure | Empirical formula | MW |
|---|---|---|---|
| Example 23 | 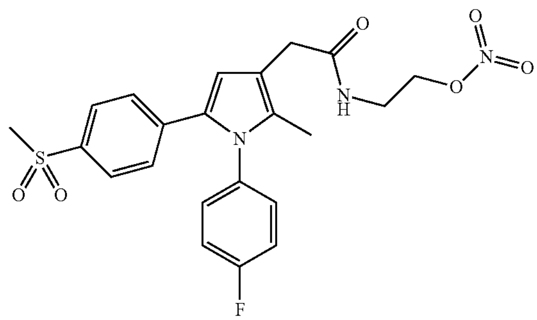 [SMILES: Cc1c(CC(=O)NCCO[N+](=O)[O-])cc(-c2ccc(S(C)(=O)=O)cc2)n1-c1ccc(F)cc1] | C$_{22}$H$_{22}$FN$_3$O$_6$S | 475.50 |
| Example 24 | 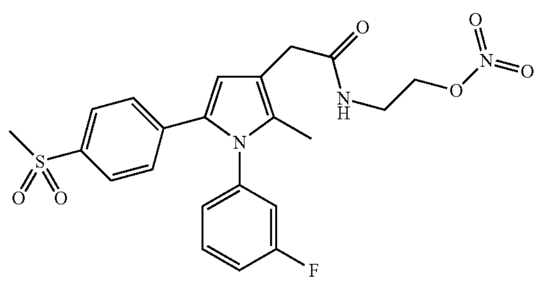 [SMILES: Cc1c(CC(=O)NCCO[N+](=O)[O-])cc(-c2ccc(S(C)(=O)=O)cc2)n1-c1cccc(F)c1] | C$_{22}$H$_{22}$FN$_3$O$_6$S | 475.50 |
| Example 25 | 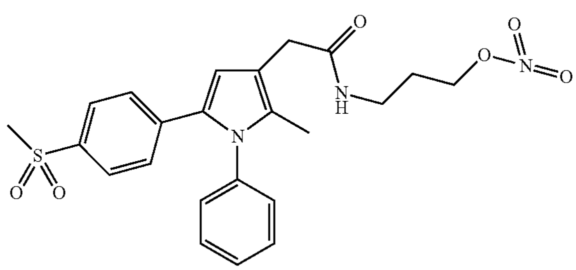 [SMILES: Cc1c(CC(=O)NCCCO[N+](=O)[O-])cc(-c2ccc(S(C)(=O)=O)cc2)n1-c1ccccc1] | C$_{23}$H$_{25}$N$_3$O$_6$S | 471.54 |
| Example 26 | 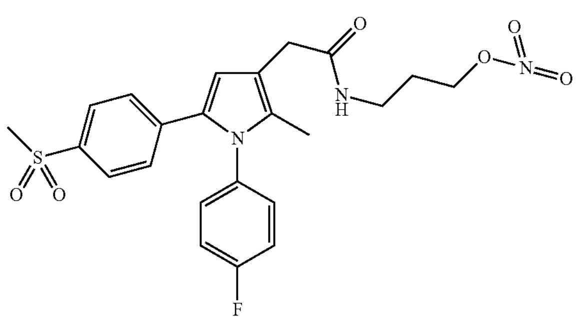 [SMILES: Cc1c(CC(=O)NCCCO[N+](=O)[O-])cc(-c2ccc(S(C)(=O)=O)cc2)n1-c1ccc(F)cc1] | C$_{23}$H$_{24}$FN$_3$O$_6$S | 489.53 |
| Example 27 | 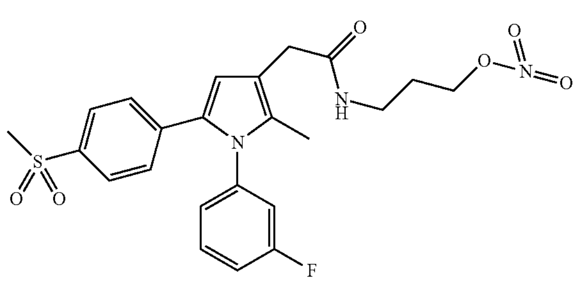 [SMILES: Cc1c(CC(=O)NCCCO[N+](=O)[O-])cc(-c2ccc(S(C)(=O)=O)cc2)n1-c1cccc(F)c1] | C$_{23}$H$_{24}$FN$_3$O$_6$S | 489.53 |

TABLE 2-continued

Representative examples of Compounds of Formula (I-b):

| Example | Structure | Empirical formula | MW |
|---|---|---|---|
| Example 28 | 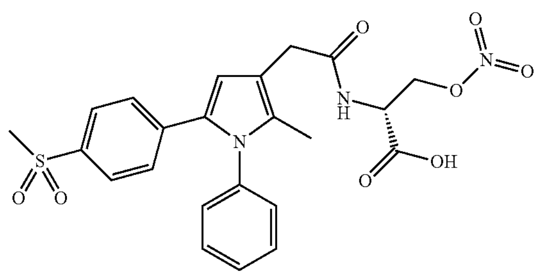 [SMILES: Cc1c(CC(=O)N[C@H](CO[N+](=O)[O-])C(=O)O)cc(-c2ccc(S(C)(=O)=O)cc2)n1-c1ccccc1] | $C_{23}H_{23}N_3O_8S$ | 501.52 |
| Example 29 | 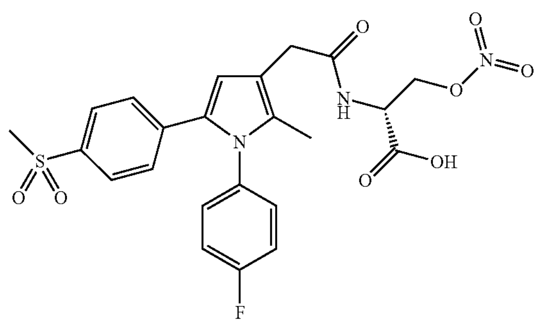 [SMILES: Cc1c(CC(=O)N[C@H](CO[N+](=O)[O-])C(=O)O)cc(-c2ccc(S(C)(=O)=O)cc2)n1-c1ccc(F)cc1] | $C_{23}H_{23}FN_3O_8S$ | 519.51 |
| Example 30 | 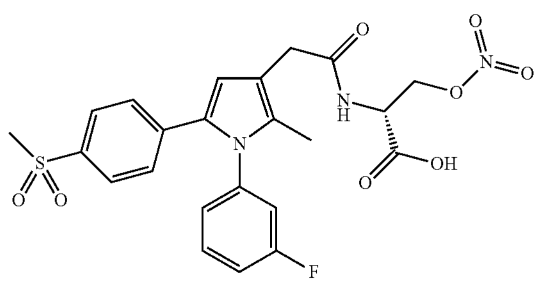 [SMILES: Cc1c(CC(=O)N[C@H](CO[N+](=O)[O-])C(=O)O)cc(-c2ccc(S(C)(=O)=O)cc2)n1-c1cccc(F)c1] | $C_{23}H_{23}FN_3O_8S$ | 519.51 |
| Example 31 | 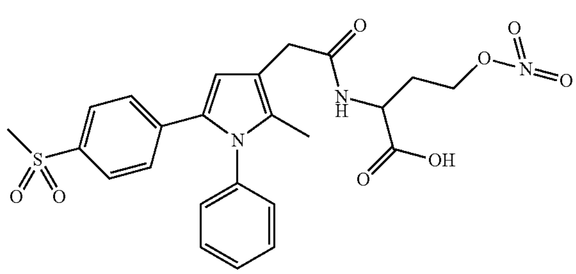 [SMILES: Cc1c(CC(=O)NC(CCO[N+](=O)[O-])C(=O)O)cc(-c2ccc(S(C)(=O)=O)cc2)n1-c1ccccc1] | $C_{24}H_{25}N_3O_8S$ | 515.55 |
| Example 32 | 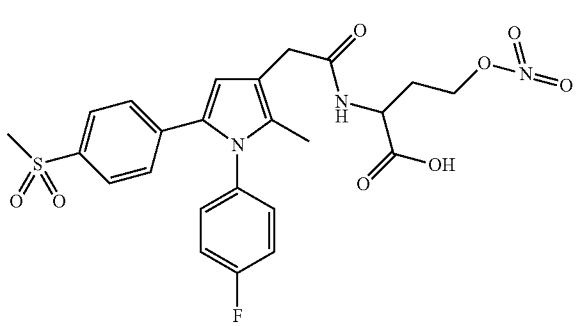 [SMILES: Cc1c(CC(=O)NC(CCO[N+](=O)[O-])C(=O)O)cc(-c2ccc(S(C)(=O)=O)cc2)n1-c1ccc(F)cc1] | $C_{24}H_{25}FN_3O_8S$ | 533.54 |

TABLE 2-continued

Representative examples of Compounds of Formula (I-b):

| Example | Structure | Empirical formula | MW |
|---|---|---|---|
| Example 33 | (structure shown) | $C_{24}H_{25}FN_3O_8S$ | 533.54 |
| Example 34 | (structure shown) | $C_{22}H_{24}N_4O_6S$ | 472.52 |
| Example 35 | (structure shown) | $C_{23}H_{26}N_4O_6S$ | 486.55 |

Compounds of Formula I-c:

when, in the compounds of Formula (I), group X is a methylene/methine —(CHR$_3$)— and group Y is an oxygen atom (—O—), the compounds of Formula (I) are ethers of formula (I-c):

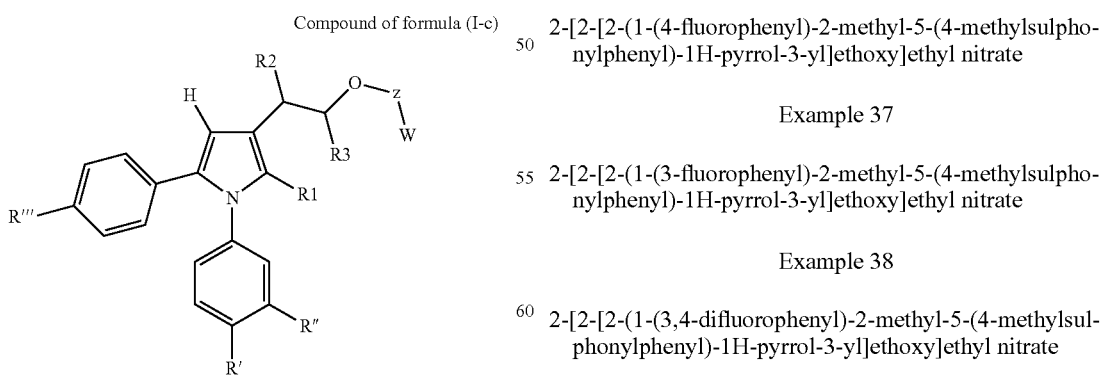

Compound of formula (I-c)

where group Z is a methylene/methine group —(CHR$_3$)— and the other substituents are as defined for the compounds of Formula (I).

Representative examples of compounds of formula (I-c) are:

2-[2-[2-(1-phenyl-2-methyl-5-(4-methylsulphonylphenyl)-1H-pyrrol-3-yl)]ethoxy]ethyl nitrate Example 36

2-[2-[2-(1-(4-fluorophenyl)-2-methyl-5-(4-methylsulphonylphenyl)-1H-pyrrol-3-yl]ethoxy]ethyl nitrate Example 37

2-[2-[2-(1-(3-fluorophenyl)-2-methyl-5-(4-methylsulphonylphenyl)-1H-pyrrol-3-yl]ethoxy]ethyl nitrate Example 38

2-[2-[2-(1-(3,4-difluorophenyl)-2-methyl-5-(4-methylsulphonylphenyl)-1H-pyrrol-3-yl]ethoxy]ethyl nitrate Example 39

3-[2-[2-(1-phenyl-2-methyl-5-(4-methylsulphonylphenyl)-1H-pyrrol-3-yl)ethoxy]propyl nitrate

Example 40

3-[2-[2-(1-(4-fluorophenyl)-2-methyl-5-(4-methylsulphonylphenyl)-1H-pyrrol-3-yl)]ethoxy]propyl nitrate

Example 41

3-[2-(1-(3-fluorophenyl)-2-methyl-5-(4-methylsulphonylphenyl)-1H-pyrrol-3-yl)ethoxy]propyl nitrate

Example 42

Representative examples of compounds of formula (I-c) where R2 is amino (—NH$_2$) are:
(R,S)-2-[3-(nitroxy)propyl]-1-[1-phenyl-2-methyl-5-(4-methylsulphonylphenyl)-1H-pyrrol-3-yl]ethanamine

Example 43

(R,S)-2-[2-(nitroxy)ethyl]-1-[1-(4-fluorophenyl)-2-methyl-5-(4-methylsulphonylphenyl)-1H-pyrrol-3-yl]ethanamine

Example 44

(R,S)-2-[3-(nitroxy)propyl]-1-[1-(4-fluorophenyl)-2-methyl-5-(4-methylsulphonylphenyl)-1H-pyrrol-3-yl]ethanamine

Example 45

The structures relating to the representative examples of the compounds of formula (I-c) listed above are shown in Table 3.

TABLE 3

| Representative examples of Compounds of Formula (I-c): | | | |
|---|---|---|---|
| Example | Structure | Empirical formula | MW |
| Example 36 | | $C_{22}H_{24}N_2O_6S$ | 444.51 |
| Example 37 | | $C_{22}H_{23}FN_2O_6S$ | 462.50 |
| Example 38 | | $C_{22}H_{23}FN_2O_6S$ | 462.50 |

TABLE 3-continued

Representative examples of Compounds of Formula (I-c):

| Example | Structure | Empirical formula | MW |
|---|---|---|---|
| Example 39 | 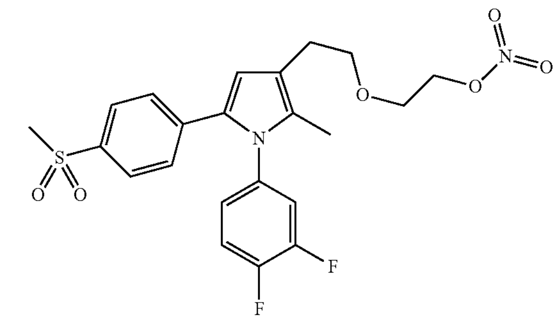 [SMILES: Cc1c(CCOCCO[N+](=O)[O-])cc(-c2ccc(S(C)(=O)=O)cc2)n1-c1ccc(F)c(F)c1] | $C_{22}H_{22}F_2N_2O_6S$ | 480.49 |
| Example 40 | 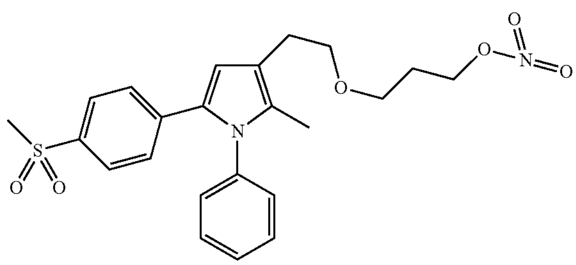 [SMILES: Cc1c(CCOCCCO[N+](=O)[O-])cc(-c2ccc(S(C)(=O)=O)cc2)n1-c1ccccc1] | $C_{23}H_{26}N_2O_6S$ | 458.54 |
| Example 41 | 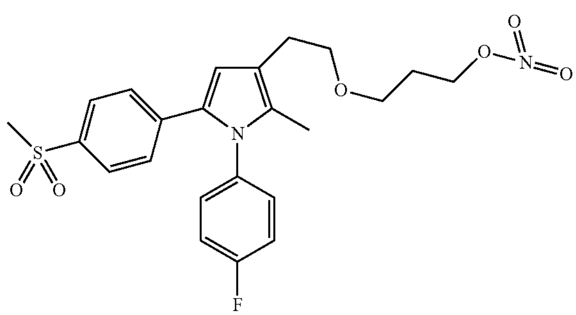 [SMILES: Cc1c(CCOCCCO[N+](=O)[O-])cc(-c2ccc(S(C)(=O)=O)cc2)n1-c1ccc(F)cc1] | $C_{23}H_{25}FN_2O_6S$ | 476.53 |
| Example 42 | 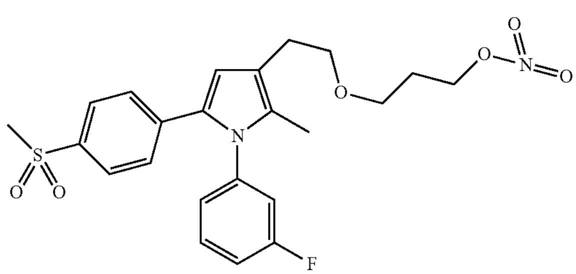 [SMILES: Cc1c(CCOCCCO[N+](=O)[O-])cc(-c2ccc(S(C)(=O)=O)cc2)n1-c1cccc(F)c1] | $C_{23}H_{25}FN_2O_6S$ | 476.53 |
| Example 43 | 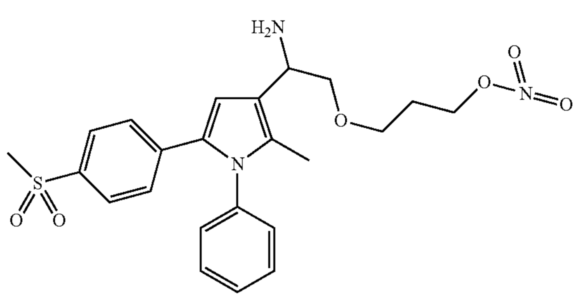 [SMILES: Cc1c(C(N)COCCCO[N+](=O)[O-])cc(-c2ccc(S(C)(=O)=O)cc2)n1-c1ccccc1] | $C_{23}H_{27}N_3O_6S$ | 473.55 |

TABLE 3-continued

Representative examples of Compounds of Formula (I-c):

| Example | Structure | Empirical formula | MW |
|---|---|---|---|
| Example 44 | 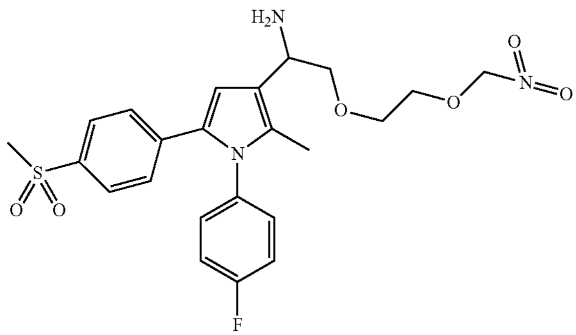 [SMILES: Cc1c(C(N)COCCOC[N+](=O)[O-])cc(-c2ccc(S(C)(=O)=O)cc2)n1-c1ccc(F)cc1] | C$_{22}$H$_{24}$FN$_3$O$_6$S | 477.52 |
| Example 45 | 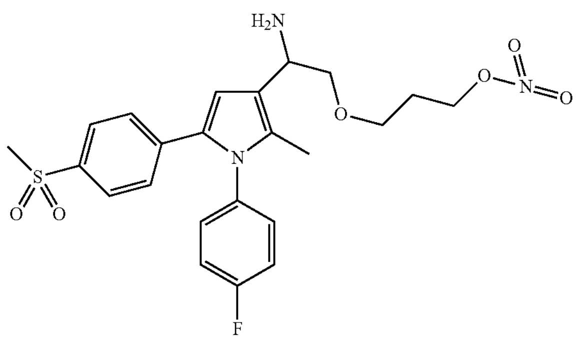 [SMILES: Cc1c(C(N)COCCCO[N+](=O)[O-])cc(-c2ccc(S(C)(=O)=O)cc2)n1-c1ccc(F)cc1] | C$_{23}$H$_{26}$FN$_3$O$_6$S | 491.54 |

Compounds of Formula (I-d):

when, in the compounds of Formula (I), X is a methylene/methine group —(CHR$_3$)—, group Y is an oxygen atom (—O—), and group Z is a carbonyl group —(C=O)—, the compounds of Formula (I) are esters of formula (I-d):

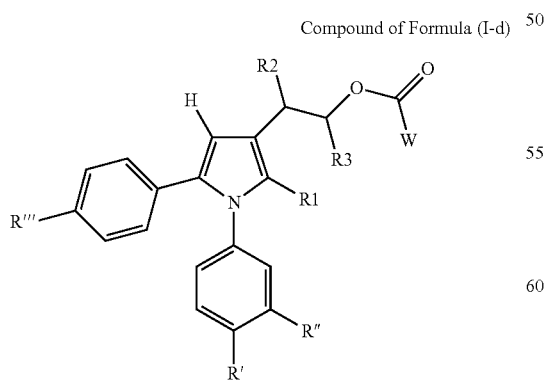

Compound of Formula (I-d)

where W and the other substituents have the same meanings as were assigned to the compounds of Formula (I).

Representative examples of compounds of formula (I-d) are:

2-(nitrooxy)-[2-[(1-(4-fluorophenyl)-2-methyl-5-(4-methylsulphonylphenyl)-1H-pyrrol-3-yl]ethoxy]acetate Example 46

4-(nitrooxy)-[2-[(1-phenyl-2-methyl-5-(4-methylsulphonylphenyl)-1H-pyrrol-3-yl]ethoxy]butanoate Example 47

The structures relating to the representative examples of the compounds of formula (I-d) listed above are shown in Table 4.

TABLE 4

Representative examples of Compounds of Formula (I-d):

| Example | Structure | Empirical formula | MW |
|---|---|---|---|
| Example 46 | 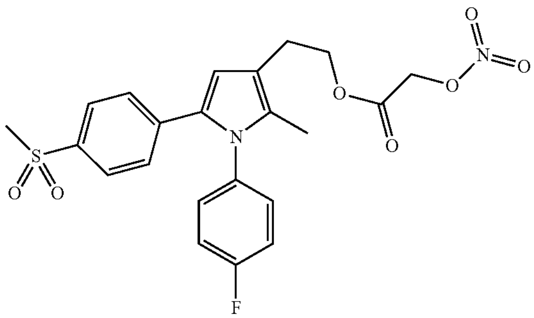 [SMILES: Cc1c(CCOC(=O)CO[N+](=O)[O-])cc(-c2ccc(S(C)(=O)=O)cc2)n1-c1ccc(F)cc1] | $C_{22}H_{21}FN_2O_7S$ | 476.48 |
| Example 47 | 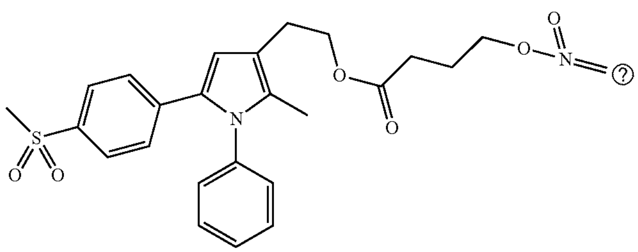 | $C_{24}H_{26}N_2O_7S$ | 486.55 |

Compounds of Formula (I-e):

when, in the compounds of Formula (I), group X is a methylene/methine group —(CHR$_3$)—, and group Y is an —NR$_3$— group and group Z is a carbonyl, the compounds of Formula (I) are amides of formula (I-e):

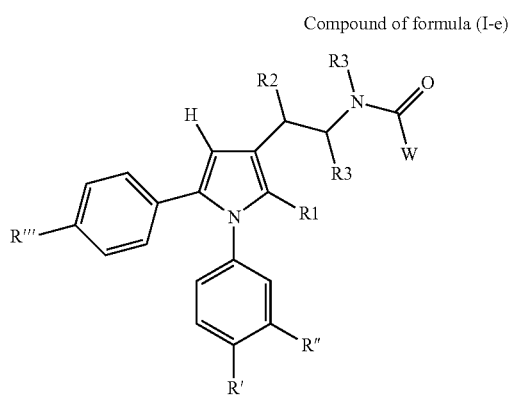

Compound of formula (I-e)

where R2, R3 and W and the other substituents are as defined for the compounds of Formula (I).

Representative examples of compounds of formula (I-e) are:

2-(nitroxy)-N-[2-(1-phenyl-2-methyl-5-(4-methylsulphonylphenyl)-1H-pyrrol-3-yl)-ethyl]acetamide Example 48

2-(nitroxy)-N-methyl-N-[2-(1-phenyl-2-methyl-5-(4-methylsulphonylphenyl)-1H-pyrrol-3-yl)-ethyl]acetamide Example 49

3-(nitroxy)-N-[2-(1-phenyl-2-methyl-5-(4-methylsulphonylphenyl)-1H-pyrrol-3-yl)-ethyl]propionamide Example 50

3-(nitroxy)-N-methyl-N-[2-(1-phenyl-2-methyl-5-(4-methylsulphonylphenyl)-1H-pyrrol-3-yl)-ethyl]propionamide Example 51

(R,S)-2-amino-3-(nitroxy)-N-[2-(1-phenyl)-2-methyl-5-(4-methylsulphonylphenyl)-1H-pyrrol-3-yl)-ethyl]propionamide Example 52

The structures relating to the representative examples of the compounds of formula (I-e) listed above are shown in Table 5.

TABLE 5

Representative examples of Compounds of Formula (I-e):

| Example | Structure | Empirical formula | MW |
|---------|-----------|-------------------|-----|
| Example 48 | 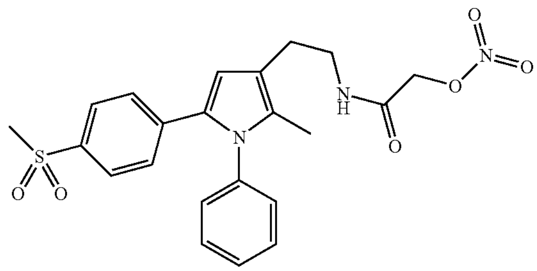 [SMILES: Cc1c(CCNC(=O)CO[N+](=O)[O-])cc(-c2ccc(S(C)(=O)=O)cc2)n1-c1ccccc1] | $C_{22}H_{23}N_3O_6S$ | 457.51 |
| Example 49 | 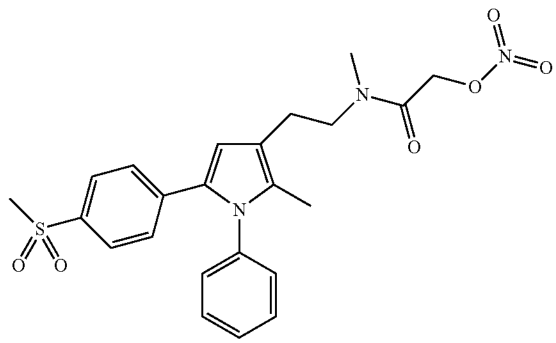 [SMILES: Cc1c(CCN(C)C(=O)CO[N+](=O)[O-])cc(-c2ccc(S(C)(=O)=O)cc2)n1-c1ccccc1] | $C_{23}H_{25}N_3O_6S$ | 471.54 |
| Example 50 | 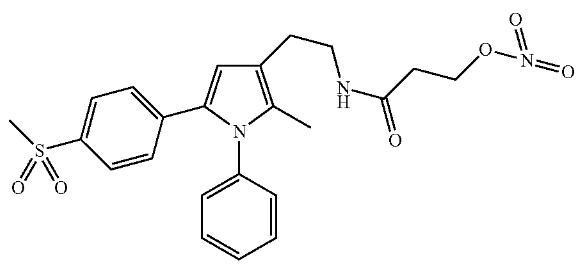 [SMILES: Cc1c(CCNC(=O)CCO[N+](=O)[O-])cc(-c2ccc(S(C)(=O)=O)cc2)n1-c1ccccc1] | $C_{23}H_{25}N_3O_6S$ | 471.54 |
| Example 51 | 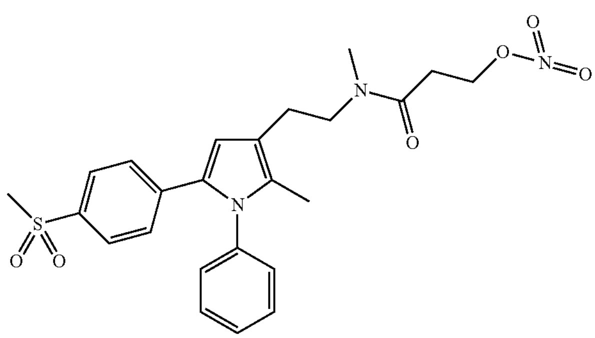 [SMILES: Cc1c(CCN(C)C(=O)CCO[N+](=O)[O-])cc(-c2ccc(S(C)(=O)=O)cc2)n1-c1ccccc1] | $C_{24}H_{27}N_3O_6S$ | 485.56 |
| Example 52 | 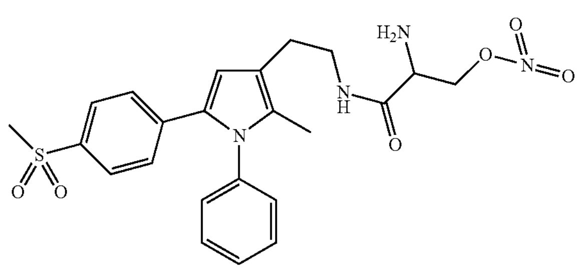 [SMILES: Cc1c(CCNC(=O)C(N)CO[N+](=O)[O-])cc(-c2ccc(S(C)(=O)=O)cc2)n1-c1ccccc1] | $C_{23}H_{26}N_4O_6S$ | 486.55 |

The nitro esters of organic compounds can be metabolized in vivo to the corresponding alcohols and NO, said metabolism can take place both in the blood, at vascular endothelial level, and in other tissues, by the action of specific enzymes. Consequently, the nitro esters of Formula (I) of the invention will be metabolized in the body to the corresponding alcohols of Formula (II):

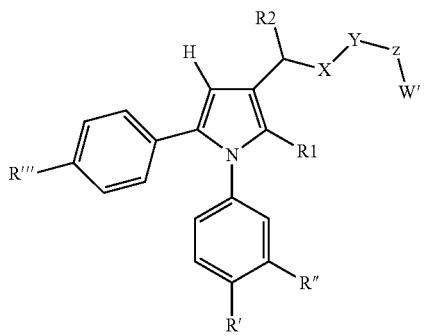

where the substituents R', R", R'", R1, R2, X, Y, Z have the meanings described above for the compounds of Formula (I) and W' is a saturated aliphatic chain with 1 to 3 carbon atoms, linear or branched, substituted with one or two OH groups. The alcohols of formula (II), metabolites of the nitro esters of formula (I), surprisingly have been found to be active in inhibition of COX-2, and therefore are pharmacologically active for the same therapeutic indications discussed above for the compounds of formula (I). Accordingly, the present invention also relates to the alcohols of formula (II), active metabolites of the compounds of formula (I).

Representative examples of compounds of formula (II) are:
2-(hydroxy)ethyl-[1-phenyl-2-methyl-5-(4-methylsulphonylphenyl)-1H-pyrrol-3-yl]-acetate Example 1-II 2-(hydroxy)ethyl-[1-(4-fluorophenyl)-2-methyl-5-(4-methylsulphonylphenyl)-1H-pyrrol-3-yl]-acetate Example 2-II 2-(hydroxy)ethyl-[1-(3-fluorophenyl)-2-methyl-5-(4-methylsulphonylphenyl)-1H-pyrrol-3-yl]-acetate Example 3-II 2-(hydroxy)ethyl-[1-(4-methoxyphenyl)-2-methyl-5-(4-methylsulphonylphenyl)-1H-pyrrol-3-yl]-acetate Example 4-II 2-(hydroxy)ethyl-[1-(4-methylthiophenyl)-2-methyl-5-(4-methylsulphonylphenyl)-1H-pyrrol-3-yl]-acetate Example 5-II 3-(hydroxy)propyl-[1-phenyl-2-methyl-5-(4-methylsulphonylphenyl)-1H-pyrrol-3-yl]-acetate Example 6-II 3-(hydroxy)propyl-[1-(4-fluorophenyl)-2-methyl-5-(4-methylsulphonylphenyl)-1H-pyrrol-3-yl]-acetate Example 7-II 3-(hydroxy)propyl-[1-(3-fluorophenyl)-2-methyl-5-(4-methylsulphonylphenyl)-1H-pyrrol-3-yl]-acetate Example 8-II 3-(hydroxy)propyl-[1-(4-methoxyphenyl)-2-methyl-5-(4-methylsulphonylphenyl)-1H-pyrrol-3-yl]-acetate Example 9-II 3-(hydroxy)propyl-[1-(4-methylthiophenyl)-2-methyl-5-(4-methylsulphonylphenyl)-1H-pyrrol-3-yl]-acetate Example 10-II 4-(hydroxy)butyl-[1-(4-fluorophenyl)-2-methyl-5-(4-methylsulphonylphenyl)-1H-pyrrol-3-yl]-acetate Example 11-II 4-(hydroxy)butyl-[1-(3-fluorophenyl)-2-methyl-5-(4-methylsulphonylphenyl)-1H-pyrrol-3-yl]-acetate Example 12-II 4-(hydroxy)butyl-[1-(4-methoxyphenyl)-2-methyl-5-(4-methylsulphonylphenyl)-1H-pyrrol-3-yl]-acetate Example 13-II 4-(hydroxy)butyl-[1-(4-thiomethylphenyl)-2-methyl-5-(4-methylsulphonylphenyl)-1H-pyrrol-3-yl]-acetate Example 14-II (R,S)-2,3-bis(hydroxy)propyl-2-[1-phenyl-2-methyl-5-(4-methylsulphonylphenyl)-1H-pyrrol-3-yl]-acetate Example 15-II (R,S)-2-(hydroxy)ethyl-[2-amino-[1-(4-fluorophenyl)-2-methyl-5-(4-methylsulphonylphenyl)-1H-pyrrol-3-yl]]-acetate Example 16-II (R,S)-2-(hydroxy)ethyl-[2-amino-[1-(3-fluorophenyl)-2-methyl-5-(4-methylsulphonylphenyl)-1H-pyrrol-3-yl]]-acetate Example 17-II (R,S)-3-(hydroxy)propyl-[2-amino-[1-(4-fluorophenyl)-2-methyl-5-(4-methylsulphonylphenyl)-1H-pyrrol-3-yl]]-acetate Example 18-II (R,S)-3-(hydroxy)propyl-[2-amino-[1-(3-fluorophenyl)-2-methyl-5-(4-methylsulphonylphenyl)-1H-pyrrol-3-yl]]-acetate

Example 19-II (R,S)-4-(hydroxy)butyl-[2-amino-[1-(4-fluorophenyl)-2-methyl-5-(4-methylsulphonylphenyl)-1H-pyrrol-3-yl]]-acetate

Example 20-II (R,S)-4-(hydroxy)butyl-[2-amino-[1-(3-fluorophenyl)-2-methyl-5-(4-methylsulphonylphenyl)-1H-pyrrol-3-yl]]-acetate

Example 21-II

N-[(2-hydroxy)ethyl]-2-[1-phenyl-2-methyl-5-(4-methylsulphonylphenyl)-1H-pyrrol-3-yl]acetamide

Example 22-II

N-[(2-hydroxy)ethyl]-2-[1-(4-fluorophenyl)-2-methyl-5-(4-methylsulphonylphenyl)-1H-pyrrol-3-yl]acetamide

Example 23-II

N-[(2-hydroxy)ethyl]-2-[1-(3-fluorophenyl)-2-methyl-5-(4-methylsulphonylphenyl)-1H-pyrrol-3-yl]acetamide

Example 24-II

N-[(3-hydroxy)propyl]-2-[1-phenyl-2-methyl-5-(4-methylsulphonylphenyl)-1H-pyrrol-3-yl]acetamide

Example 25-II

N-[(3-hydroxy)propyl]-2-[1-(4-fluorophenyl)-2-methyl-5-(4-methylsulphonylphenyl)-1H-pyrrol-3-yl]acetamide

Example 26-II

N-[(3-nitroxy)propyl]-2-[1-(3-fluorophenyl)-2-methyl-5-(4-methylsulphonylphenyl)-1H-pyrrol-3-yl]acetamide

Example 27-II

MAB146

(S)-3-(hydroxy)-2-[[1-phenyl-2-methyl-5-(4-methylsulphonylphenyl)-1H-pyrrol-3-yl]acetamido]propanoic acid

Example 28-II (S)-3-(hydroxy)-2-[[1-(4-fluorophenyl)-2-methyl-5-(4-methylsulphonylphenyl)-1H-pyrrol-3-yl]acetamido]propanoic acid

Example 29-II (S)-3-(hydroxy)-2-[[1-(3-fluorophenyl)-2-methyl-5-(4-methylsulphonylphenyl)-1H-pyrrol-3-yl]acetamido]propanoic acid

Example 30-II (R,S)-4-(hydroxy)-2-[[1-phenyl-2-methyl-5-(4-methylsulphonylphenyl)-1H-pyrrol-3-yl]acetamido]butanoic acid

Example 31-II (R,S)-4-(hydroxy)-2-[[1-(4-fluorophenyl)-2-methyl-5-(4-methylsulphonylphenyl)-1H-pyrrol-3-yl]acetamido]butanoic acid

Example 32-II (R,S)-4-(hydroxy)-2-[[1-(3-fluorophenyl)-2-methyl-5-(4-methylsulphonylphenyl)-1H-pyrrol-3-yl]acetamido]butanoic acid

Example 33-II (R,S)-2-amino-N-(2-hydroxy)ethyl-2-[1-phenyl-2-methyl-5-(4-methylsulphonylphenyl)-1H-pyrrol-3-yl]acetamide

Example 34-II (R,S)-2-amino-N-(3-hydroxy)propyl-2-[1-phenyl-2-methyl-5-(4-methylsulphonylphenyl)-1H-pyrrol-3-yl]acetamide

Example 35-II

2-[2-[2-(1-phenyl-2-methyl-5-(4-methylsulphonylphenyl)-1H-pyrrol-3-yl)]ethoxy]ethanol

Example 36-II

2-[2-[2-(1-(4-fluorophenyl)-2-methyl-5-(4-methylsulphonylphenyl)-1H-pyrrol-3-yl]ethoxy]ethanol

Example 37-II

2-[2-[2-(1-(3-fluorophenyl)-2-methyl-5-(4-methylsulphonylphenyl)-1H-pyrrol-3-yl]ethoxy]ethanol

Example 38-II

2-[2-[2-(1-(3,4-difluorophenyl)-2-methyl-5-(4-methylsulphonylphenyl)-1H-pyrrol-3-yl]ethoxy]ethanol

Example 39-II

3-[2-[2-(1-phenyl-2-methyl-5-(4-methylsulphonylphenyl)-1H-pyrrol-3-yl]ethoxy]propanol

Example 40-II

3-[2-[2-(1-(4-fluorophenyl)-2-methyl-5-(4-methylsulphonylphenyl)-1H-pyrrol-3-yl)]ethoxy]propanol

Example 41-II

3-[2-(1-(3-fluorophenyl)-2-methyl-5-(4-methylsulphonylphenyl)-1H-pyrrol-3-yl)ethoxy]propanol

Example 42-II (R,S)-2-[3-(hydroxy)propyl]-1-[1-phenyl-2-methyl-5-(4-methylsulphonylphenyl)-1H-pyrrol-3-yl]ethanamine

Example 43-II (R,S)-2-[2-(hydroxy)ethyl]-1-[1-(4-fluorophenyl)-2-methyl-5-(4-methylsulphonylphenyl)-1H-pyrrol-3-yl]ethanamine

Example 44-II (R,S)-2-[3-(hydroxy)propyl]-1-[1-(4-fluorophenyl)-2-methyl-5-(4-methylsulphonylphenyl)-1H-pyrrol-3-yl]ethanamine

Example 45-II 2-(hydroxy)-N-[2-(1-phenyl-2-methyl-5-(4-methylsulphonylphenyl)-1H-pyrrol-3-yl)-ethyl]acetamide 3-(hydroxy)-N-[2-(1-phenyl-2-methyl-5-(4-methylsulphonylphenyl)-1H-pyrrol-3-yl)-ethyl]propionamide

Example 44-II (R,S)-2-amino-3-hydroxy-N-[2-(1-phenyl)-2-methyl-5-(4-methylsulphonylphenyl)-1H-pyrrol-3-yl)-ethyl]propionamide

Example 45-II 2-amino-2-hydroxy-N-[1-phenyl-2-methyl-5-(4-methylsulphonylphenyl)-1H-pyrrol-3-yl)-ethyl]acetamide

Example 48-II 2-amino-2-hydroxy-N-methyl-N-[1-phenyl-2-methyl-5-(4-methylsulphonylphenyl)-1H-pyrrol-3-yl)-ethyl]acetamide

Example 49-II 2-amino-3-hydroxy-N-[1-phenyl-2-methyl-5-(4-methylsulphonylphenyl)-1H-pyrrol-3-yl)-ethyl]propionamide

Example 50-II 2-amino-3-hydroxy-N-methyl-N-[1-phenyl-2-methyl-5-(4-methylsulphonylphenyl)-1H-pyrrol-3-yl)-ethyl]propionamide

Example 51-II (R,S)-2-amino-3-hydroxy-N-2[1-phenyl-2-methyl-5-(4-methylsulphonylphenyl)-1H-pyrrol-3-yl)-ethyl]propionamide

Example 52-II

The structures relating to the representative examples of the compounds of formula (II) listed above are shown in Table 6.

TABLE 6

Representative examples of Compounds of Formula (II):

| Example | Structure | Empirical formula | MW |
|---|---|---|---|
| Example 1-II | 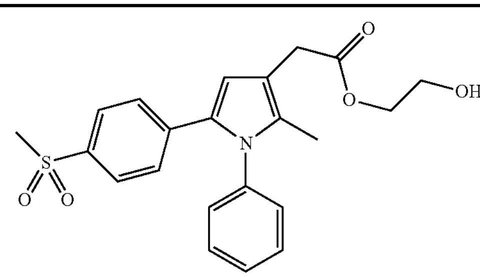 | $C_{22}H_{23}NO_5S$ | 413.50 |
| Example 2-II | 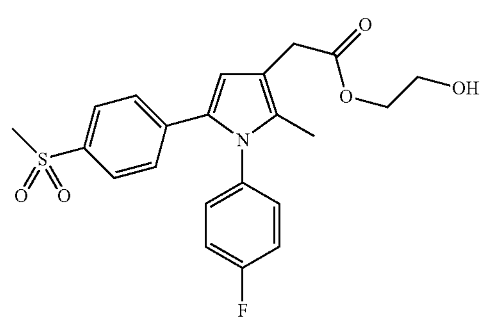 [SMILES: Cc1c(CC(=O)OCCO)cc(-c2ccc(S(C)(=O)=O)cc2)n1-c1ccc(F)cc1] | $C_{22}H_{22}FNO_5S$ | 431.49 |
| Example 3-II | 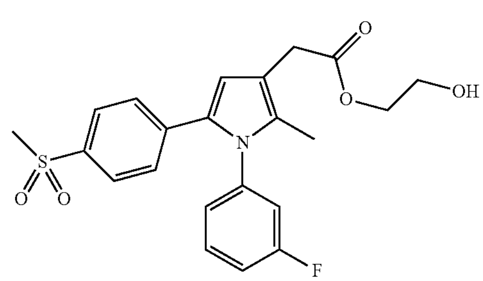 [SMILES: Cc1c(CC(=O)OCCO)cc(-c2ccc(S(C)(=O)=O)cc2)n1-c1cccc(F)c1] | $C_{22}H_{22}FNO_5S$ | 431.49 |

TABLE 6-continued

Representative examples of Compounds of Formula (II):

| Example | Structure | Empirical formula | MW |
| --- | --- | --- | --- |
| Example 4-II | 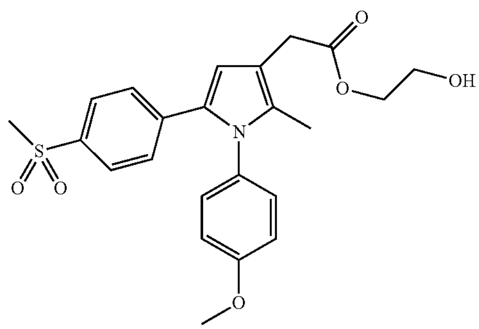 [SMILES: COc1ccc(-n2c(-c3ccc(S(C)(=O)=O)cc3)cc(CC(=O)OCCO)c2C)cc1] | $C_{23}H_{25}NO_6S$ | 443.52 |
| Example 5-II | 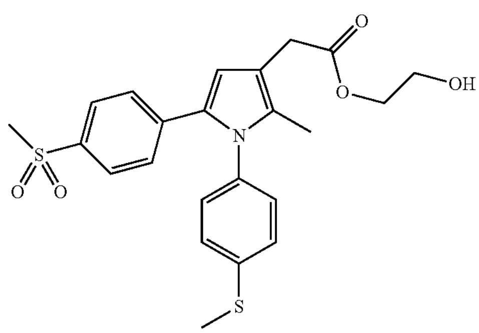 [SMILES: CSc1ccc(-n2c(-c3ccc(S(C)(=O)=O)cc3)cc(CC(=O)OCCO)c2C)cc1] | $C_{23}H_{25}NO_5S_2$ | 459.59 |
| Example 6-II | 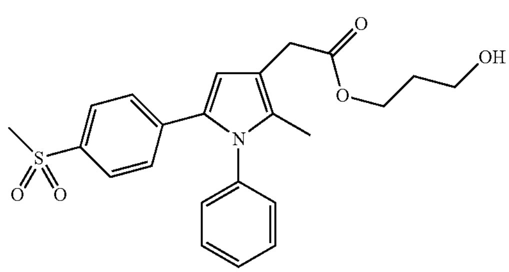 [SMILES: Cc1c(CC(=O)OCCCO)cc(-c2ccc(S(C)(=O)=O)cc2)n1-c1ccccc1] | $C_{23}H_{25}NO_5S$ | 427.52 |
| Example 7-II | 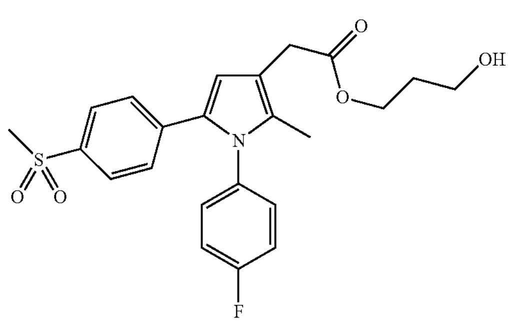 [SMILES: Cc1c(CC(=O)OCCCO)cc(-c2ccc(S(C)(=O)=O)cc2)n1-c1ccc(F)cc1] | $C_{23}H_{24}FNO_5S$ | 445.51 |
| Example 8-II | 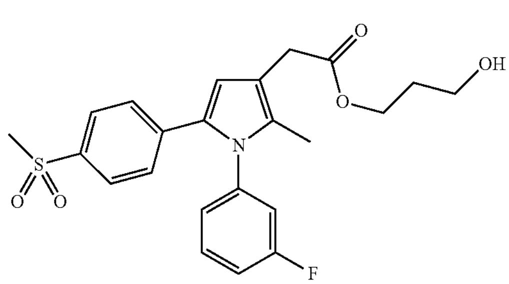 [SMILES: Cc1c(CC(=O)OCCCO)cc(-c2ccc(S(C)(=O)=O)cc2)n1-c1cccc(F)c1] | $C_{23}H_{24}FNO_5S$ | 445.51 |

TABLE 6-continued

Representative examples of Compounds of Formula (II):

| Example | Structure | Empirical formula | MW |
|---|---|---|---|
| Example 9-II | 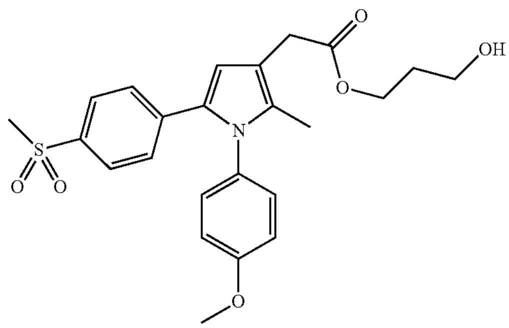 [SMILES: COc1ccc(-n2c(-c3ccc(S(C)(=O)=O)cc3)cc(CC(=O)OCCCO)c2C)cc1] | $C_{24}H_{27}NO_6S$ | 457.55 |
| Example 10-II | 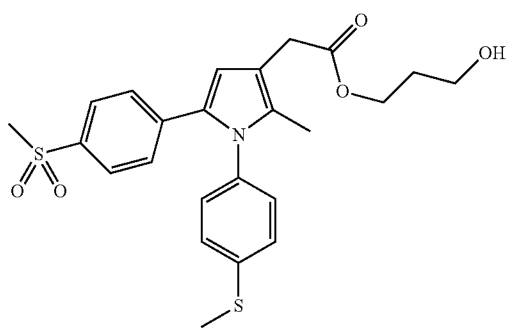 | $C_{24}H_{27}NO_5S_2$ | 473.61 |
| Example 11-II | 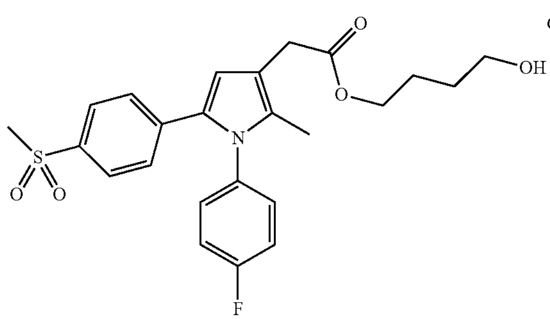 [SMILES: Cc1c(CC(=O)OCCCCO)cc(-c2ccc(S(C)(=O)=O)cc2)n1-c1ccc(F)cc1] | $C_{24}H_{26}FNO_5S$ | 459.54 |
| Example 12-II | 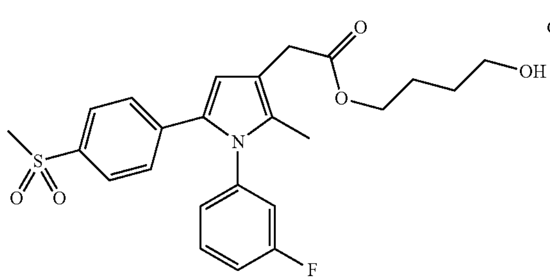 [SMILES: Cc1c(CC(=O)OCCCCO)cc(-c2ccc(S(C)(=O)=O)cc2)n1-c1cccc(F)c1] | $C_{24}H_{26}FNO_5S$ | 459.54 |

TABLE 6-continued

Representative examples of Compounds of Formula (II):

| Example | Structure | Empirical formula | MW |
|---|---|---|---|
| Example 13-II | 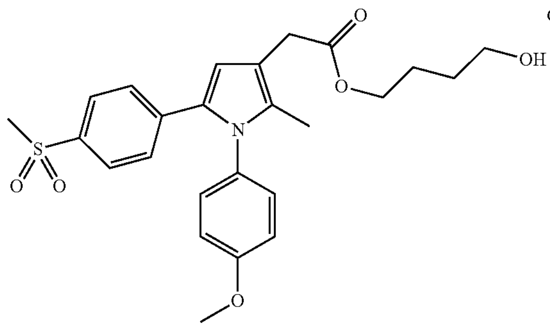 [SMILES: CSc1ccc(-n2c(-c3ccc(S(C)(=O)=O)cc3)cc(CC(=O)OCCCCO)c2C)cc1] | $C_{25}H_{29}NO_6S$ | 471.58 |
| Example 14-II | 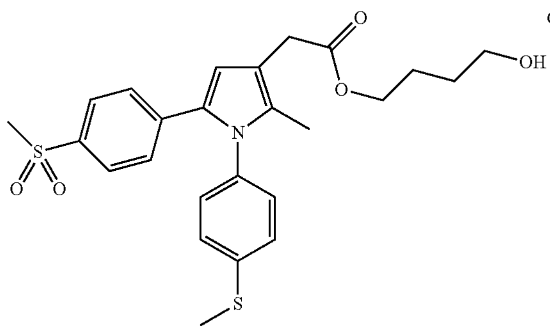 | $C_{25}H_{29}NO_5S_2$ | 487.64 |
| Example 15-II | 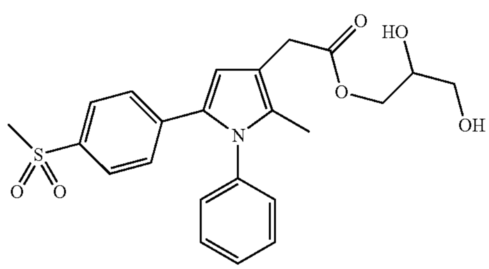 [SMILES: Cc1c(CC(=O)OCC(O)CO)cc(-c2ccc(S(C)(=O)=O)cc2)n1-c1ccccc1] | $C_{23}H_{25}NO_6S$ | 443.52 |
| Example 16-II | 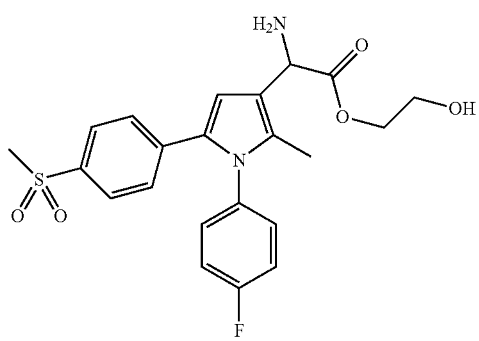 [SMILES: Cc1c(C(N)C(=O)OCCO)cc(-c2ccc(S(C)(=O)=O)cc2)n1-c1ccc(F)cc1] | $C_{22}H_{23}FN_2O_5S$ | 446.50 |
| Example 17-II | 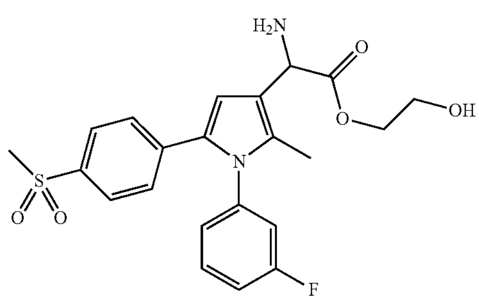 [SMILES: Cc1c(C(N)C(=O)OCCO)cc(-c2ccc(S(C)(=O)=O)cc2)n1-c1cccc(F)c1] | $C_{22}H_{23}FN_2O_5S$ | 446.50 |

TABLE 6-continued

Representative examples of Compounds of Formula (II):

| Example | Structure | Empirical formula | MW |
|---|---|---|---|
| Example 18-II | 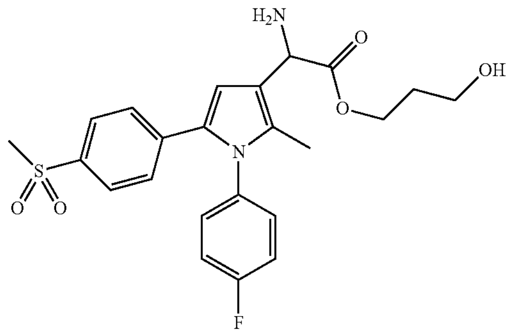 [SMILES: Cc1c(C(N)C(=O)OCCCO)cc(-c2ccc(S(C)(=O)=O)cc2)n1-c1ccc(F)cc1] | $C_{23}H_{25}FN_2O_5S$ | 460.53 |
| Example 19-II | 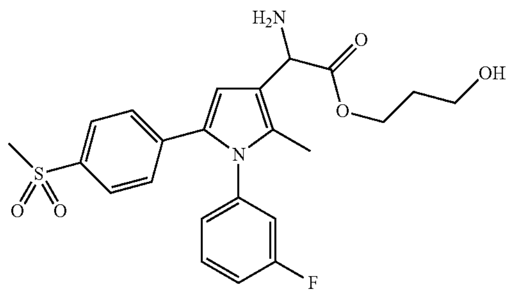 [SMILES: Cc1c(C(N)C(=O)OCCCO)cc(-c2ccc(S(C)(=O)=O)cc2)n1-c1cccc(F)c1] | $C_{23}H_{25}FN_2O_5S$ | 460.53 |
| Example 20-II | 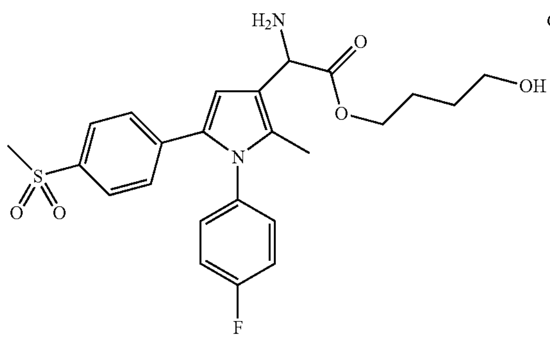 [SMILES: Cc1c(C(N)C(=O)OCCCCO)cc(-c2ccc(S(C)(=O)=O)cc2)n1-c1ccc(F)cc1] | $C_{24}H_{27}FN_2O_5S$ | 474.56 |
| Example 21-II | 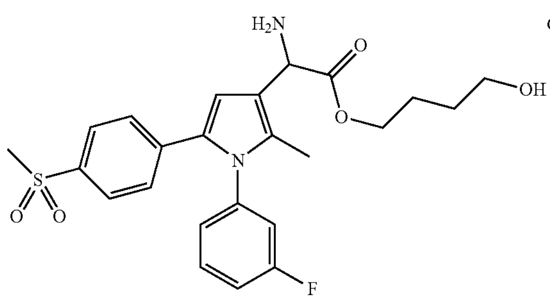 [SMILES: Cc1c(C(N)C(=O)OCCCCO)cc(-c2ccc(S(C)(=O)=O)cc2)n1-c1cccc(F)c1] | $C_{24}H_{27}FN_2O_5S$ | 474.56 |
| Example 22-II | 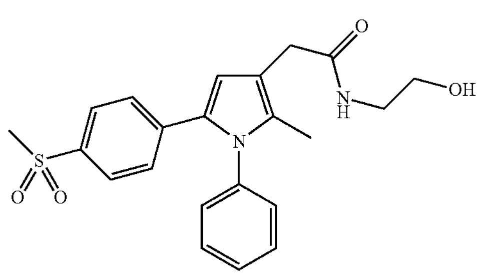 [SMILES: Cc1c(CC(=O)NCCO)cc(-c2ccc(S(C)(=O)=O)cc2)n1-c1ccccc1] | $C_{22}H_{24}N_2O_4S$ | 412.51 |

TABLE 6-continued

Representative examples of Compounds of Formula (II):

| Example | Structure | Empirical formula | MW |
|---|---|---|---|
| Example 23-II | 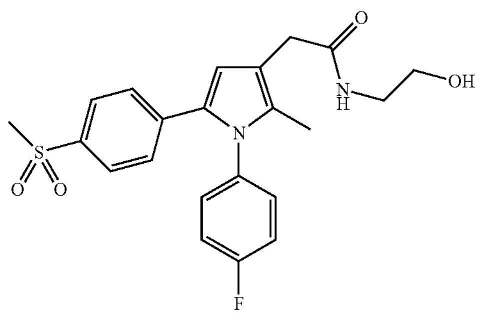 [SMILES: Cc1c(CC(=O)NCCO)cc(-c2ccc(S(C)(=O)=O)cc2)n1-c1ccc(F)cc1] | $C_{22}H_{23}FN_2O_4S$ | 430.50 |
| Example 24-II | 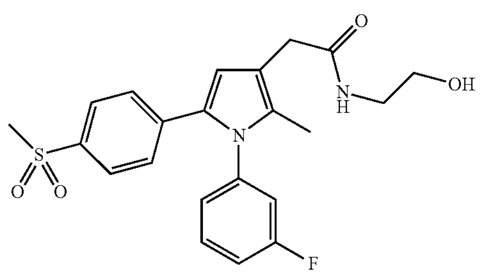 [SMILES: Cc1c(CC(=O)NCCO)cc(-c2ccc(S(C)(=O)=O)cc2)n1-c1cccc(F)c1] | $C_{22}H_{23}FN_2O_4S$ | 430.50 |
| Example 25-II | 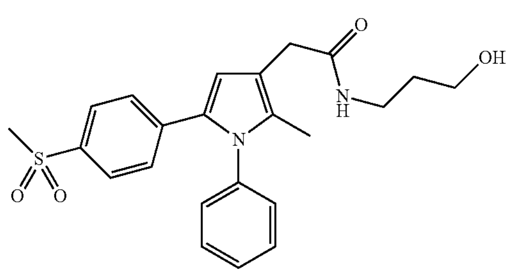 [SMILES: Cc1c(CC(=O)NCCCO)cc(-c2ccc(S(C)(=O)=O)cc2)n1-c1ccccc1] | $C_{23}H_{26}N_2O_4S$ | 426.54 |
| Example 26-II | 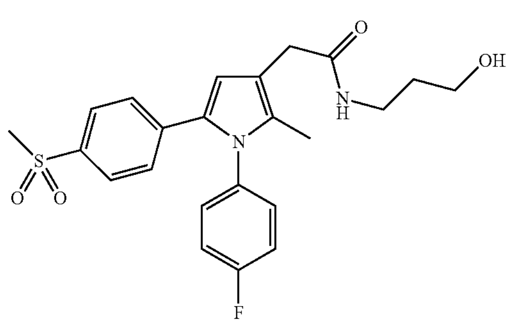 [SMILES: Cc1c(CC(=O)NCCCO)cc(-c2ccc(S(C)(=O)=O)cc2)n1-c1ccc(F)cc1] | $C_{23}H_{25}FN_2O_4S$ | 444.53 |
| Example 27-II | 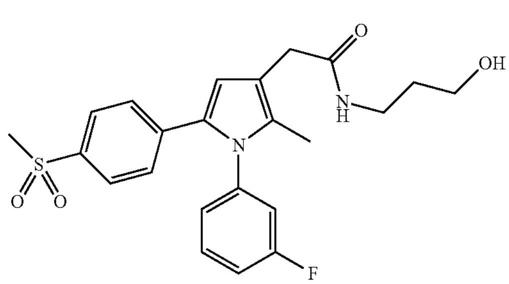 [SMILES: Cc1c(CC(=O)NCCCO)cc(-c2ccc(S(C)(=O)=O)cc2)n1-c1cccc(F)c1] | $C_{23}H_{25}FN_2O_4S$ | 444.53 |

TABLE 6-continued

Representative examples of Compounds of Formula (II):

| Example | Structure | Empirical formula | MW |
|---|---|---|---|
| Example 28-II | 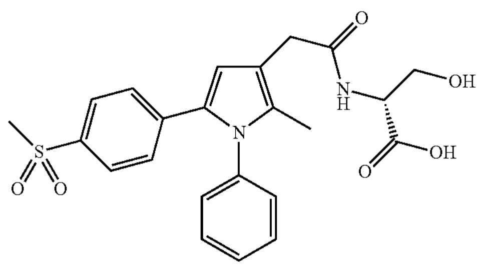 [SMILES: Cc1c(CC(=O)N[C@H](CO)C(=O)O)cc(-c2ccc(S(C)(=O)=O)cc2)n1-c1ccccc1] | $C_{23}H_{24}N_2O_6S$ | 456.52 |
| Example 29-II | 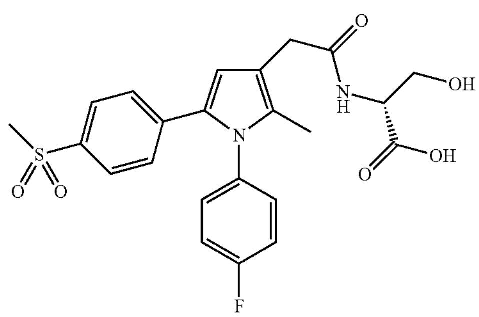 [SMILES: Cc1c(CC(=O)N[C@H](CO)C(=O)O)cc(-c2ccc(S(C)(=O)=O)cc2)n1-c1ccc(F)cc1] | $C_{23}H_{23}FN_2O_6S$ | 474.51 |
| Example 30-II | 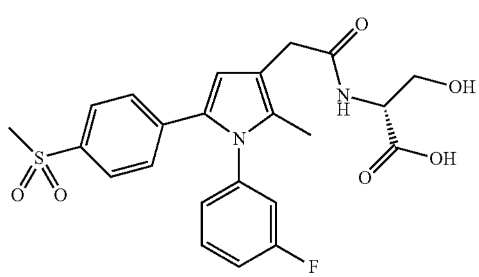 [SMILES: Cc1c(CC(=O)N[C@H](CO)C(=O)O)cc(-c2ccc(S(C)(=O)=O)cc2)n1-c1cccc(F)c1] | $C_{23}H_{23}FN_2O_6S$ | 474.51 |
| Example 31-II | 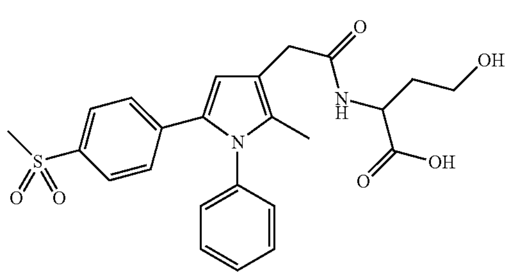 [SMILES: Cc1c(CC(=O)NC(CCO)C(=O)O)cc(-c2ccc(S(C)(=O)=O)cc2)n1-c1ccccc1] | $C_{24}H_{26}N_2O_6S$ | 470.55 |
| Example 32-II | 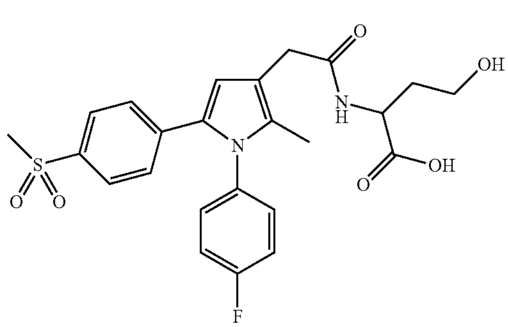 [SMILES: Cc1c(CC(=O)NC(CCO)C(=O)O)cc(-c2ccc(S(C)(=O)=O)cc2)n1-c1ccc(F)cc1] | $C_{24}H_{25}FN_2O_6S$ | 488.54 |

TABLE 6-continued
Representative examples of Compounds of Formula (II):
| Example | Structure | Empirical formula | MW |
|---|---|---|---|
| Example 33-II | 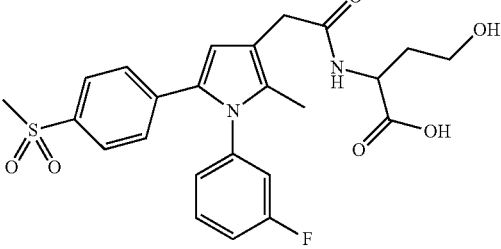 | $C_{24}H_{25}FN_2O_6S$ | 488.54 |
| Example 34-II | 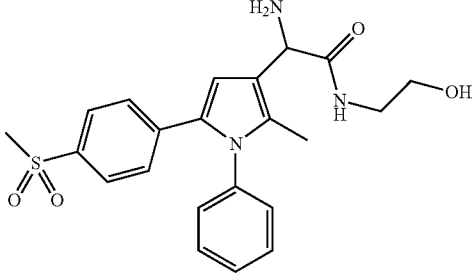 [SMILES: Cc1c(C(N)C(=O)NCCO)cc(-c2ccc(S(C)(=O)=O)cc2)n1-c1ccccc1] | $C_{22}H_{25}N_3O_4S$ | 427.53 |
| Example 35-II | 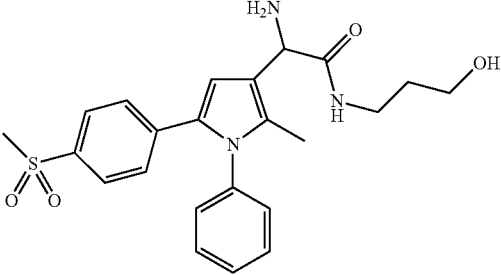 [SMILES: Cc1c(C(N)C(=O)NCCCO)cc(-c2ccc(S(C)(=O)=O)cc2)n1-c1ccccc1] | $C_{23}H_{27}N_3O_4S$ | 441.55 |
| Example 36-II | 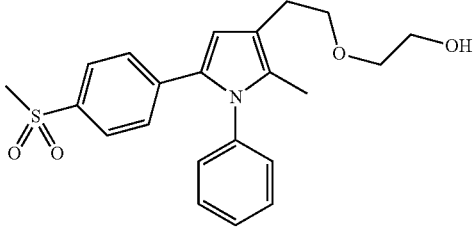 [SMILES: Cc1c(CCOCCO)cc(-c2ccc(S(C)(=O)=O)cc2)n1-c1ccccc1] | $C_{22}H_{25}NO_4S$ | 399.51 |
| Example 37-II | 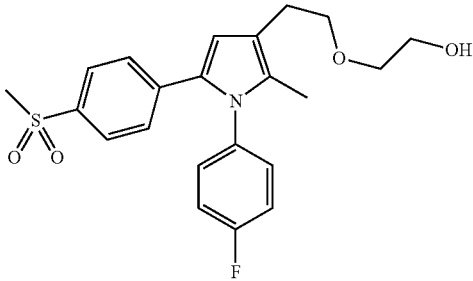 [SMILES: Cc1c(CCOCCO)cc(-c2ccc(S(C)(=O)=O)cc2)n1-c1ccc(F)cc1] | $C_{22}H_{24}FNO_4S$ | 417.50 |

TABLE 6-continued
Representative examples of Compounds of Formula (II):
| Example | Structure | Empirical formula | MW |
|---|---|---|---|
| Example 38-II | 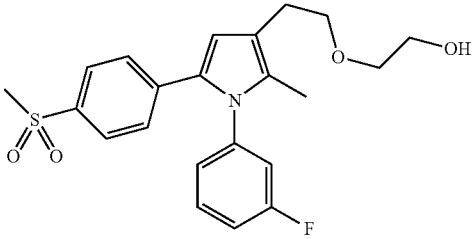 [SMILES: Cc1c(CCOCCO)cc(-c2ccc(S(C)(=O)=O)cc2)n1-c1cccc(F)c1] | C$_{22}$H$_{24}$FNO$_4$S | 417.50 |
| Example 39-II | 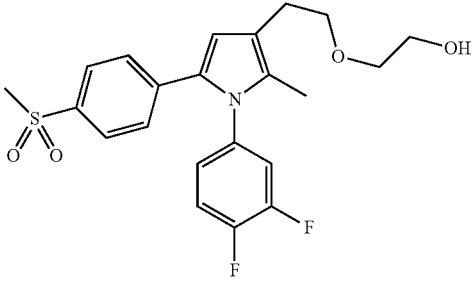 [SMILES: Cc1c(CCOCCO)cc(-c2ccc(S(C)(=O)=O)cc2)n1-c1ccc(F)c(F)c1] | C$_{22}$H$_{23}$F$_2$NO$_4$S | 435.49 |
| Example 40-II | 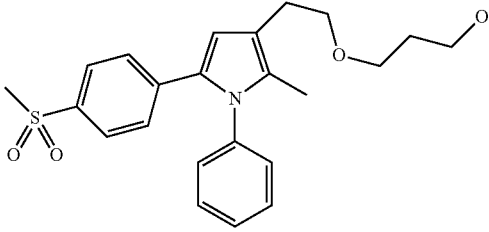 | C$_{23}$H$_{27}$NO$_4$S | 413.54 |
| Example 41-II | 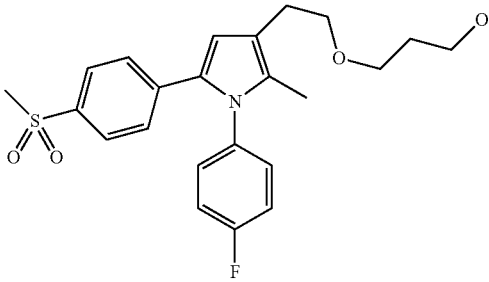 | C$_{23}$H$_{26}$FNO$_4$S | 431.53 |
| Example 42-II | 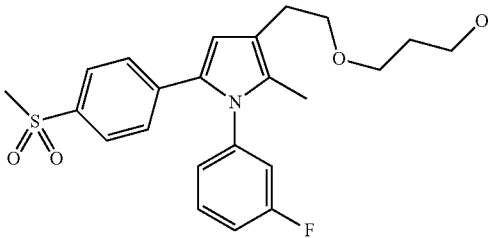 | C$_{23}$H$_{26}$FNO$_4$S | 431.53 |

TABLE 6-continued

Representative examples of Compounds of Formula (II):

| Example | Structure | Empirical formula | MW |
| --- | --- | --- | --- |
| Example 43-II | 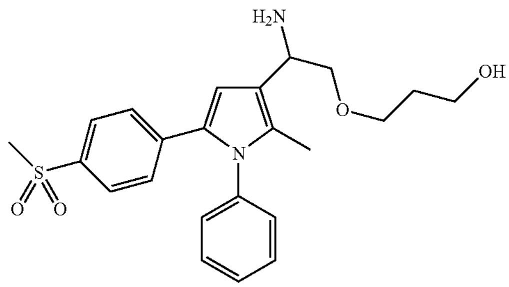 [SMILES: Cc1c(C(N)COCCCO)cc(-c2ccc(S(C)(=O)=O)cc2)n1-c1ccccc1] | $C_{23}H_{28}N_2O_4S$ | 428.55 |
| Example 44-II | 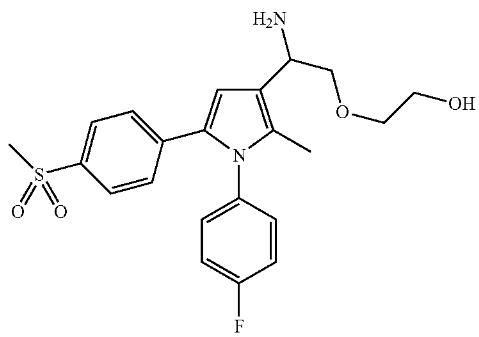 [SMILES: Cc1c(C(N)COCCO)cc(-c2ccc(S(C)(=O)=O)cc2)n1-c1ccc(F)cc1] | $C_{22}H_{25}FN_2O_4S$ | 432.52 |
| Example 45-II | 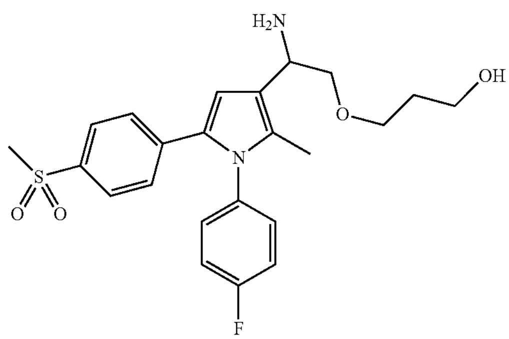 [SMILES: Cc1c(C(N)COCCCO)cc(-c2ccc(S(C)(=O)=O)cc2)n1-c1ccc(F)cc1] | $C_{23}H_{27}FN_2O_4S$ | 446.55 |
| Example 48-II | 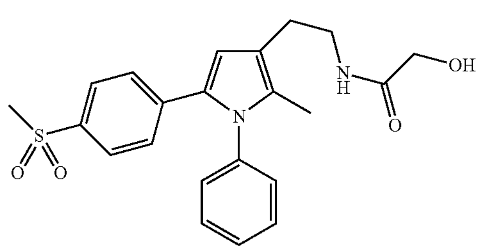 [SMILES: Cc1c(CCNC(=O)CO)cc(-c2ccc(S(C)(=O)=O)cc2)n1-c1ccccc1] | $C_{22}H_{24}N_2O_4S$ | 412.51 |
| Example 49-II | 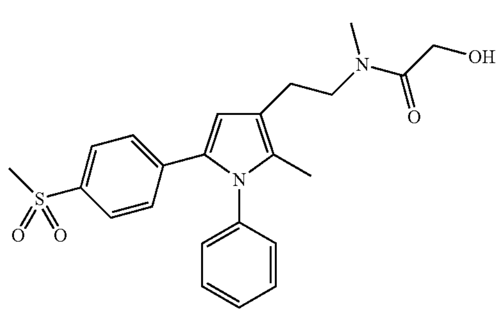 [SMILES: Cc1c(CCN(C)C(=O)CO)cc(-c2ccc(S(C)(=O)=O)cc2)n1-c1ccccc1] | $C_{23}H_{26}N_2O_4S$ | 426.54 |

TABLE 6-continued

Representative examples of Compounds of Formula (II):

| Example | Structure | Empirical formula | MW |
|---|---|---|---|
| Example 50-II | 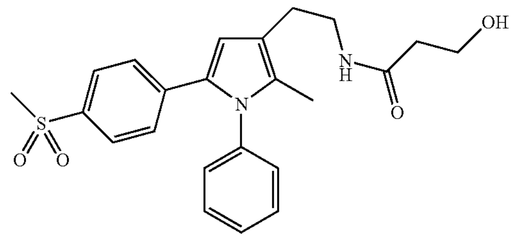 [SMILES: Cc1c(CCNC(=O)CCO)cc(-c2ccc(S(C)(=O)=O)cc2)n1-c1ccccc1] | $C_{23}H_{26}N_2O_4S$ | 426.54 |
| Example 51-II | 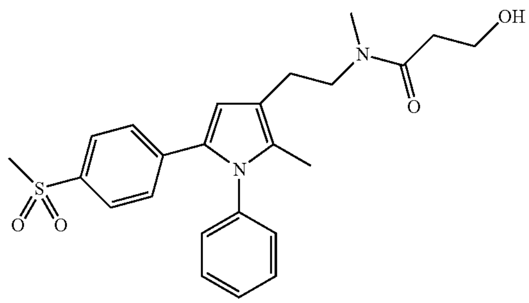 [SMILES: Cc1c(CCN(C)C(=O)CCO)cc(-c2ccc(S(C)(=O)=O)cc2)n1-c1ccccc1] | $C_{24}H_{28}N_2O_4S$ | 440.57 |
| Example 52-II | 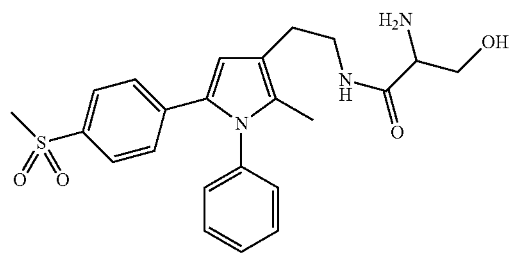 [SMILES: Cc1c(CCNC(=O)C(N)CO)cc(-c2ccc(S(C)(=O)=O)cc2)n1-c1ccccc1] | $C_{23}H_{27}N_3O_4S$ | 441.55 |

Naproxcinod and NO-flurbiprofen are the representatives of the CINOD class at the most advanced stage of clinical development; both have shown efficacy in studies of OA of the hip and of the knee, and gastric tolerability. The cardiovascular effects of naproxcinod have been analysed in phase II and phase III clinical studies, where a good effect in control of pressure was demonstrated (absence of increase in pressure compared with the group treated with naproxen). It is known that naproxcinod, when incubated with sections of rat aorta, is metabolized, giving rise to NO. It is known, moreover, that naproxen (3; FIG. 1), in order to inhibit cyclooxygenase, must be released from naproxcinod by hydrolytic action of esterase, as shown in FIG. 1.

Therefore naproxcinod (1) can release NO according to two independent mechanisms, the first by direct metabolism of the nitro ester (1) giving rise to the alcohol (2) and NO, the second by metabolism of the chain (4) giving rise to the diol (5) and to NO. In both cases naproxen must be released by naproxcinod to exert its analgesic and anti-inflammatory action. A similar mechanism has been reported for NO-flurbiprofen. Clinical studies conducted with naproxcinod have shown that, of the two routes given in FIG. 1, the hydrolytic route that releases naproxen (3) and the corresponding chain (4) is already very pronounced for this compound in the gastrointestinal (GI) tract. In the case of COX-2 inhibitors that are at the same time NO donors, in order to ensure good cardiovascular protection, it is important that slow release of NO occurs in association with inhibition of COX-2, so as to guarantee the necessary cardiovascular protection without giving rise to harmful hypotensive effects connected with massive release of NO—a situation that cannot occur if nitro ester, alcohol and acid resulting from hydrolysis/metabolism of the compound have very different pharmacokinetic profiles. This indicates that the fact of having both the NO donor (nitro ester) and its metabolite (alcohol), which are active in inhibiting COX-2, can represent an advantage over the previous CINODs. Therefore nitro esters that have suitably slow kinetics of release of NO and are effective in inhibiting COX-2 both as nitro esters and as alcohols will be characterized by a safer cardiovascular profile, and better efficacy. Moreover, compounds that in contrast to naproxcinod are less susceptible to extensive hydrolysis in the GI system and are characterized by COX-2 inhibitory activity both at the level of nitro ester and of the resultant metabolite (alcohol) represent a further advantage, as in this case the same molecule is both the COX-2 inhibitor and the source of slow release of NO.

The compounds of Formula (I) already as nitro esters surprisingly proved to be selective COX-2 inhibitors, with excellent properties as NO donors and in that they are characterized by a better profile of cardiovascular safety compared with the classical COX-2 inhibitors. Moreover, the compounds of the present invention proved to be effective COX-2 inhibitors both as nitro esters and as alcohols of Formula (II), resulting from metabolism of the corresponding nitro esters of Formula (I). Thus, whereas the compounds of Formula (I-a) and (I-d) are potentially hydrolysable similarly to as described above for naproxcinod, the compounds of Formula (I-c) are not hydrolysable and the amides (I-d) and (I-e) proved to be metabolically more stable than the corresponding esters. Therefore the compounds of the present invention can be used in the treatment of disorders mediated by COX-2, in particular arthritides (OA, RA), inflammatory gastrointestinal and urogenital disorders, fibromyalgia, lupus erythematosus and psoriasis. Moreover, the compounds of the present invention can be used in the treatment of pain, such as dental pain, postoperative pain, neuropathic pain, and pain induced by cancer. Finally, both for their COX-2 activity and for their capacity for releasing NO, the compounds of the present invention can be used in the treatment of pre-cancerous and cancerous forms such as gastric, hepatic, pancreatic, oesophageal, colon, breast, bladder, and lung tumours.

The invention also relates to methods for preparing the compounds of Formula (I).

The invention further relates to the pharmaceutical formulations of the compounds of formula (I). Said pharmaceutical formulations comprise oral or parenteral formulations of at least one compound of formula (I), a pharmaceutically acceptable salt or solvate thereof, with suitable excipients or solvents. For treating the disorders discussed above the daily dosage of a compound of formula (I) will be between 0.1 and 40 mg/kg, depending on the type and severity of the disorder to be treated. The oral formulations include tablets and capsules with immediate release, where suitable dispersing agents and disintegrants are added to the active ingredient, such as magnesium carbonate, magnesium stearate, magnesium oxide, talc, lactose, hydroxymethylcellulose and/or carboxymethylcellulose. The tablets and capsules are prepared by conventional techniques such as mixing, granulation and compression or filling of capsules. The parenteral formulations comprise ampoules or pre-filled syringes. In the parenteral formulations the compound of formula (I) is dissolved in aqueous saline or dextrose solution, in the formulations for intramuscular administration the product of formula (I) is administered as oily emulsion.

Preparation of the Compounds of the Invention

The compounds of formula (I) are prepared starting from the corresponding acids of formula (III) (scheme 1). The compounds of formula (III) are prepared similarly to as described previously (J. Med. Chem., 2005, 48, 3428; WO2008/014821), as shown in Scheme 1.

Compound of Formula (III)

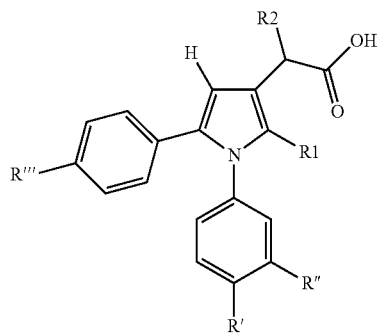

where the substituents R', R", R''', R1 and R2 have the same meanings as were assigned to the compounds of Formula (I).

Scheme 1:

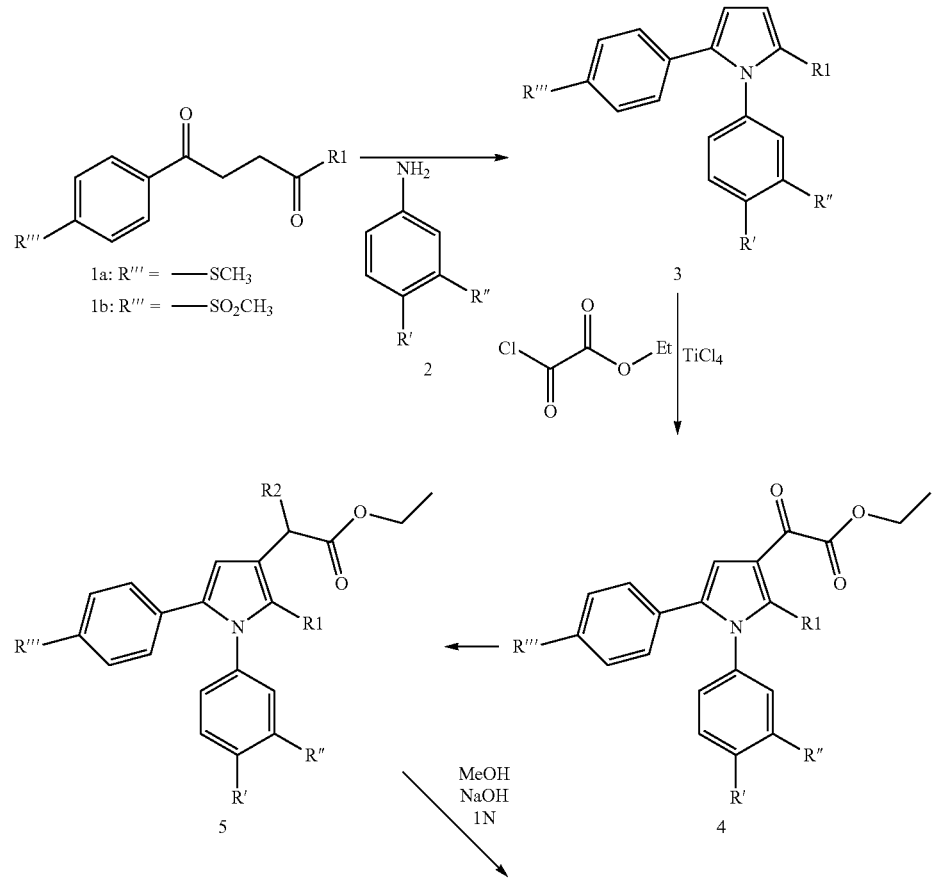

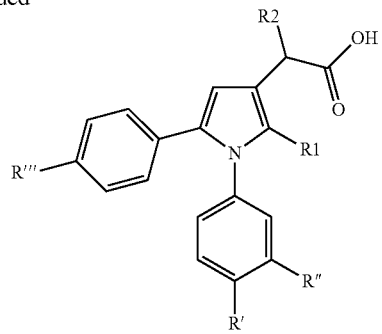

6
Compound of formula (III)

1-[4-(Methylthio)phenyl]-1,4-pentanediones (1a), obtained according to Stetter's reaction as reported previously (in particular: 1-[4-(methylthio)phenyl]-5-methyl-1,4-pentanedione, RN: 189501-33-5; 1-[4-(methylthio)phenyl]-5-trifluoromethyl-1,4-pentanedione, 1a, R1=—CF$_3$, is obtained as described in J. Med. Chem. 33(1), 21, 1990; 1-[4-(methylthio)phenyl]-5-methyloxymethyl-1,4-pentanedione, (1a), R1=—CH$_2$OCH$_3$, is obtained as described in Chemische Berichte, 1981, 114(2), 581-96; 1-[4-(methylthio)phenyl]-5-benzyloxymethyl-1,4-pentanedione, 1a where R1=—CH$_2$OCH$_2$Ph is obtained similarly) are oxidized to 1-[4-(methylsulphonyl)phenyl]-1,4-pentanediones (1b) by treatment with oxone (potassium peroxymonosulphate) in aqueous-alcoholic solution. The resultant 1-[4-methylsulphonylphenyl]-1,4-pentanediones (1b) are cyclized with the appropriate anilines (2) to diarylpyrroles (3), that are reacted with ethoxalyl chloride in the presence of TiCl$_4$ to give the glyoxylates (4). These can be reduced by triethylsilane/trifluoroacetic acid to the corresponding acetates (5) (R2=H), by NaCNBH$_3$/ZnX$_2$ to the α-oxyacetates (5) (R2=—OH or —OCH$_3$) (Biorg. & Med. Chem., 2008, 16, 8072) or to form the corresponding α-aminoacetic derivatives (5) [(R2=—NHR$_3$] by reductive amination or by reduction of the corresponding oxime as described below. The α-aminoacetic derivatives can optionally be protected at the nitrogen with groups such as: trifluoroacetyl, tert-butoxycarbonyl (BOC) or benzyloxycarbonyl (Cbz). The esters (5) (scheme 1) where R''' is a sulphonamide group are prepared from the esters (5) where R''' is a methanesulphonic group, by treatment with LDA/CH$_2$ISiMe$_3$, followed by rearrangement with sulphinic acid and transformation to sulphonamide derivative by reaction with O-hydroxylaminosulphonic acid, similarly to what was described (J. Med. Chem. 2000, 43, 3168-3185). The acids (6), compounds of formula (III), are obtained by hydrolysis of the esters (5). The following [1-aryl-2-methyl-5-(4-methylsulphonylphenyl)-1H-pyrrol-3-yl]acetic acids (6) (R2=—H) are known: 6a, aryl=phenyl, RN:853055-09-1; 6b, aryl=4-methylphenyl RN:853055-10-4; 6c, aryl=4-methoxylphenyl, RN:1201902-75-1; 6d, aryl=3-fluorophenyl, RN:1201902-73-9; 6e, aryl=3,4-difluorophenyl, RN:1201902-74-0; 6f, aryl=4-trifluoromethylphenyl, RN:853055-11-5. The following ethyl esters (5), ethyl 2-hydroxy-3-[1-aryl-2-methyl-5-(4-methylsulphonylphenyl)-1H-pyrrole]acetates (R2=—OH) are known: (5q), aryl=phenyl, S enantiomer RN:1005451-82-0, R enantiomer RN:1005451-83-1; (5r), aryl=3-fluorophenyl, S enantiomer RN:1005451-86-4, R enantiomer RN:1005451-87-5; (5s), aryl=4-methoxyphenyl, S enantiomer RN:1005451-90-0, R enantiomer RN:1005451-85-3.

When in a compound of formula (III) R2=—OH this hydroxyl is optionally protected as benzyl ether or silyl ether, compatibly with the other protecting groups present in the compound of formula (II) as discussed hereunder. A compound of formula (I-a) is obtained by reacting a compound of formula (II) (Scheme 2) with methanesulphonyl chloride (MsCl) in the presence of 4-dimethylaminopyridine (DMAP) and diisopropylethylamine (DIPEA), in dichloromethane (DCM), the mesylate thus obtained is treated with tetrabutylammonium nitrate or with silver nitrate to give the corresponding nitro ester of formula (I-a). The compound of formula (II) is obtained by reacting a compound of formula (III) with the appropriate diol of formula (IV) (Scheme 2), in the presence of a condensing agent such as 1-(3-dimethylaminopropyl)-3-ethylcarbodiimide (EDC). The diol of formula (IV) is optionally protected at one of the hydroxyl groups, suitable protecting groups are: trimethylsilyl ether (TMS), tert-butyldimethylsilyl ether (TBDMS) and benzyl ether. In the case when a compound of formula (III) is condensed with a protected diol, a deprotection step will give the compound of formula (II) as in the following example.

Scheme 2

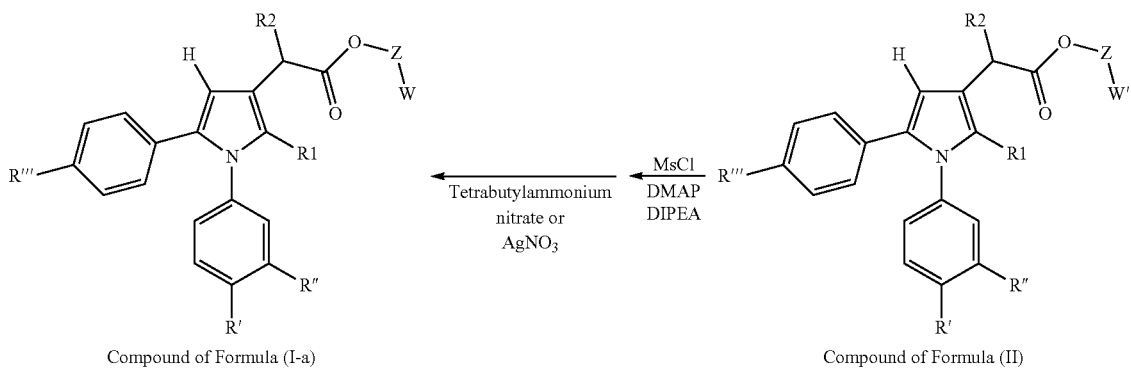

Compound of Formula (I-a)    Compound of Formula (II)

-continued

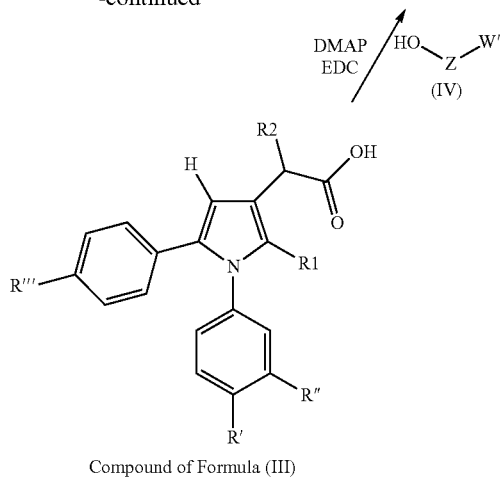

Compound of Formula (III)

Where the substituents have the same meanings previously assigned to the compounds of Formula (I), Z has the meanings assigned to the compounds (I-a) and W' is a saturated aliphatic chain, with 1 to 3 carbon atoms, linear or branched, substituted with one or two hydroxyl groups (—OH), free or protected as described above. Alternatively, a compound of formula (I-a) is obtained by reacting a compound of formula (III) (Scheme 4) with a nitro-alcohol of Formula (V), in the presence of a condensing agent such as EDC and DMAP, in a solvent such as for example DCM.

Scheme 4

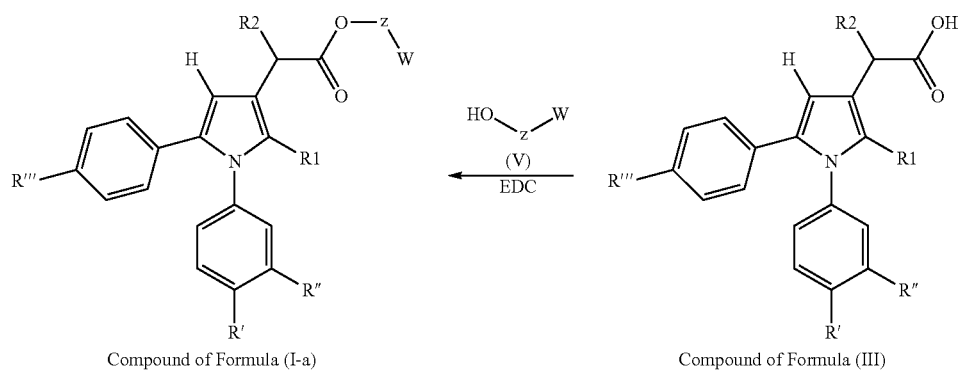

Compound of Formula (I-a)   Compound of Formula (III)

Where the substituents have the same meanings previously assigned to the compounds of formula (I-a). A compound of formula (V) is prepared by reacting the appropriate diol with a mixture of nitric and sulphuric acids, or by reaction of the appropriate hydroxyalkyl halide with tetrabutylammonium or silver nitrate as in the following example. A compound of formula (I-b) is prepared by reacting an acid of formula (III) with an amine of formula (VI) (scheme 5) in the presence of EDC, hydroxybenzotriazole (HOBt) and triethylamine (TEA) or diisopropylethylamine (DIPEA), in a solvent such as for example DCM or THF. Alternatively a compound of formula (I-b) is prepared by activation of a compound of formula (III) via a mixed anhydride, for example by reaction with isobutyl chloro-formate in the presence of N-methylmorpholine and then reaction with an amine of formula (VI).

Scheme 5

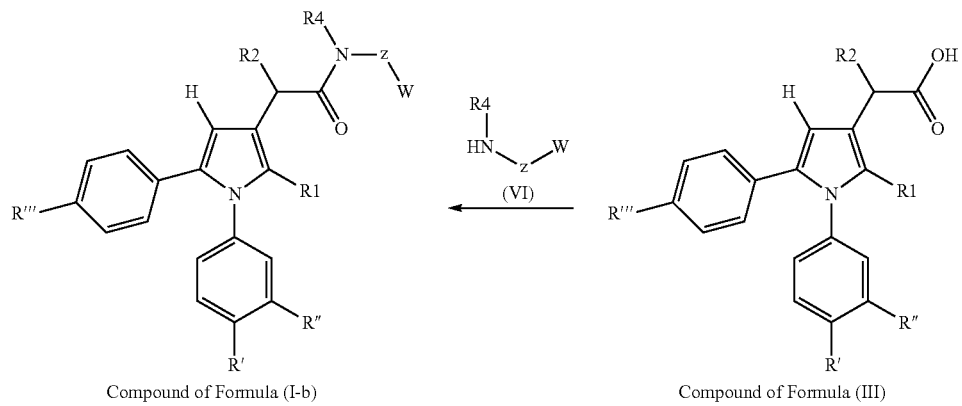

Where the substituents have the same meanings previously assigned to the compounds of formula (I-b), and $R_4$ is hydrogen (—H) or $R_3$, where $R_3$ has the same meanings as were assigned to the compounds of formula (I). The compounds of formula (VI) are prepared as described (Chemistry of Natural Compounds, 44(1), 67, 2008). The following compounds of formula (VI) are known: 2-nitroxyethylamine nitrate, RN: 4665-58-1; 3-(nitroxypropyl)amine nitrate, RN: 65141-52-8; 4-(nitroxy)butylamine, RN: 2153-95-9. A compound of formula (I-b) where Z is a —[CH(COOH)]— group is prepared by condensation of an acid of Formula (III) with the appropriate α-amino-nitroxy acid of formula (VI), where Z is a —[CH(COOH)]— group, in the presence of benzotriazol-1-yl-oxy-tris-(dimethylamino)-phosphonium hexafluorophosphate (BOP) or EDC and triethylamine in THF or DCM.

Alternatively a compound of formula (I-b) is prepared by activation of a compound of formula (III) via a mixed anhydride, for example by reaction with isobutyl chloro-formate in the presence of N-methylmorpholine, and then reaction with the α-amino-nitroxy acid of formula (VI). The carboxylate present in the compound of formula (VI) is optionally protected as: benzyl ester, trimethylsilyl ester or trimethylsilylethoxymethyl ester (SEM), the latter can be removed selectively with $MgBr_2$ (Tetrahedron Lett., 1997, 38 (23), 4025).

2-Amino-3-nitroxypropanoic acid is known: RN 927834-22-8. A compound of formula (I-c), when R3=—H, is prepared from a compound of formula (II) by reaction with mesyl chloride and tetrabutylammonium or silver nitrate as described above. The compound of formula (II) is in this case prepared by deprotection of a compound of formula (VII) (Scheme 6); where W' represents a saturated aliphatic chain, linear or branched, substituted with one or two hydroxyls, W" has the same meanings as W' except that the hydroxyl groups present are protected as discussed above and the other substituents have the same meanings previously assigned to the compounds of Formula (I-c). The substituent T in the compounds of formula (IX) is chlorine, bromine, iodine or mesylate. In a compound of formula (VII) the protecting group is selected from the protecting groups previously described for the compounds of formula (IV) and the 2-tetrahydropyranyl group. The compound of formula (VII) is obtained by alkylation of a compound of formula (VIII), with an appropriate alkyl halide of formula (IX). The compounds of formula (VIII) are prepared by reduction of the esters 5 (scheme 2) as described previously (J. Med. Chem. 2008, 51, 4476). Alkylation of a compound of formula (VII) is carried out according to known methods. A compound of formula (I-c) where R3 is alkyl is prepared from a compound of formula (II) as described above. The compound of formula (II) is obtained by deprotection of a compound of formula (X) (Scheme 7), obtained by alkylation of a compound of formula (XI) with a compound of formula (IX). The compounds of formula (XI) are prepared by addition of an organometallic compound ($R_3M$) to an aldehyde of formula (XII) obtained by reduction of an ester 5 with diisobutyl aluminium hydride (scheme 2).

Scheme 6

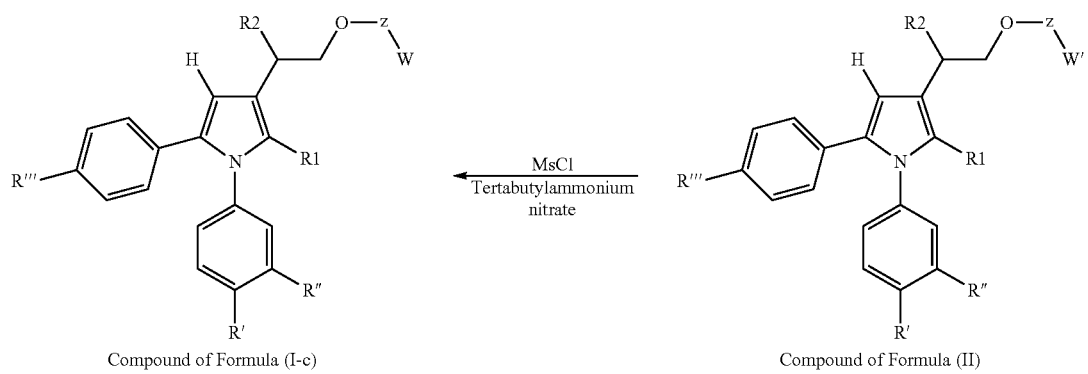

-continued

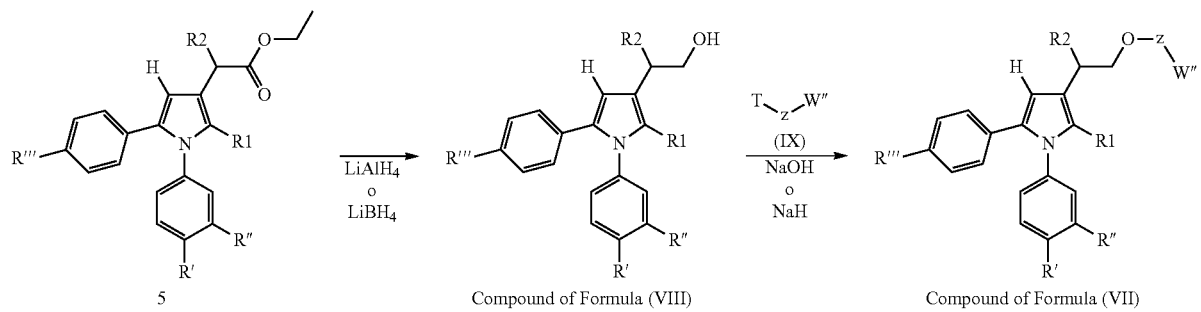

Scheme 7

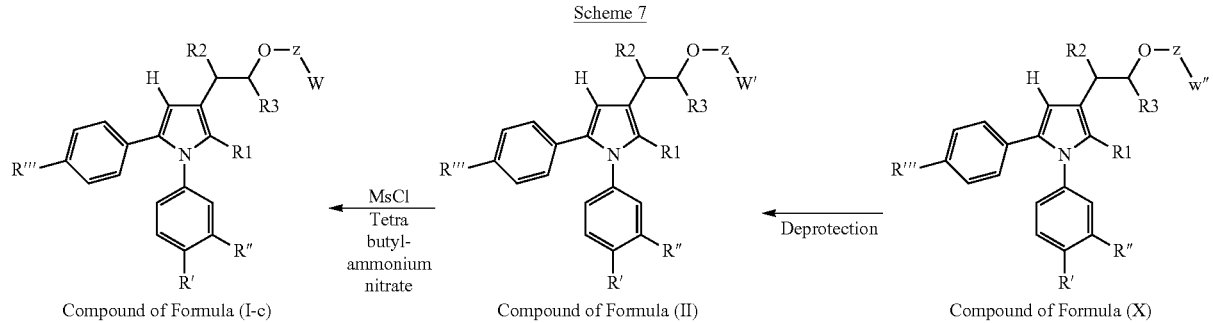

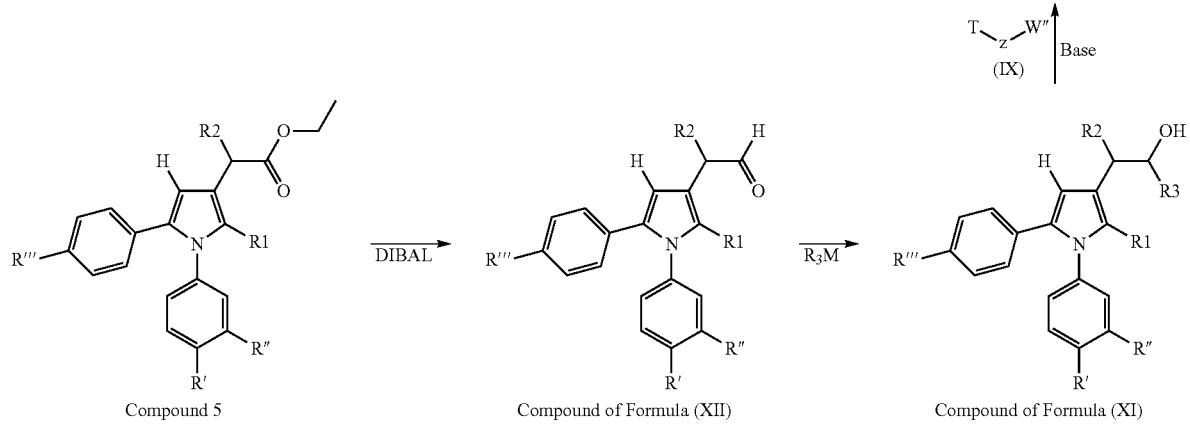

Where the meanings of the substituents are as described for scheme 6. A compound of formula (I-d) is prepared from a compound of formula (II) (Scheme 8), similarly to what was described for preparation of the compounds of formula (I-a). The compound of formula (II) is prepared by deprotection of a compound of formula (XIII), obtained by reacting a compound of formula (XIV) with a compound of formula (VIII) (scheme 6) or of formula (XI) (scheme 7) depending on the meaning of $R_3$ in the compound of formula (I-d).

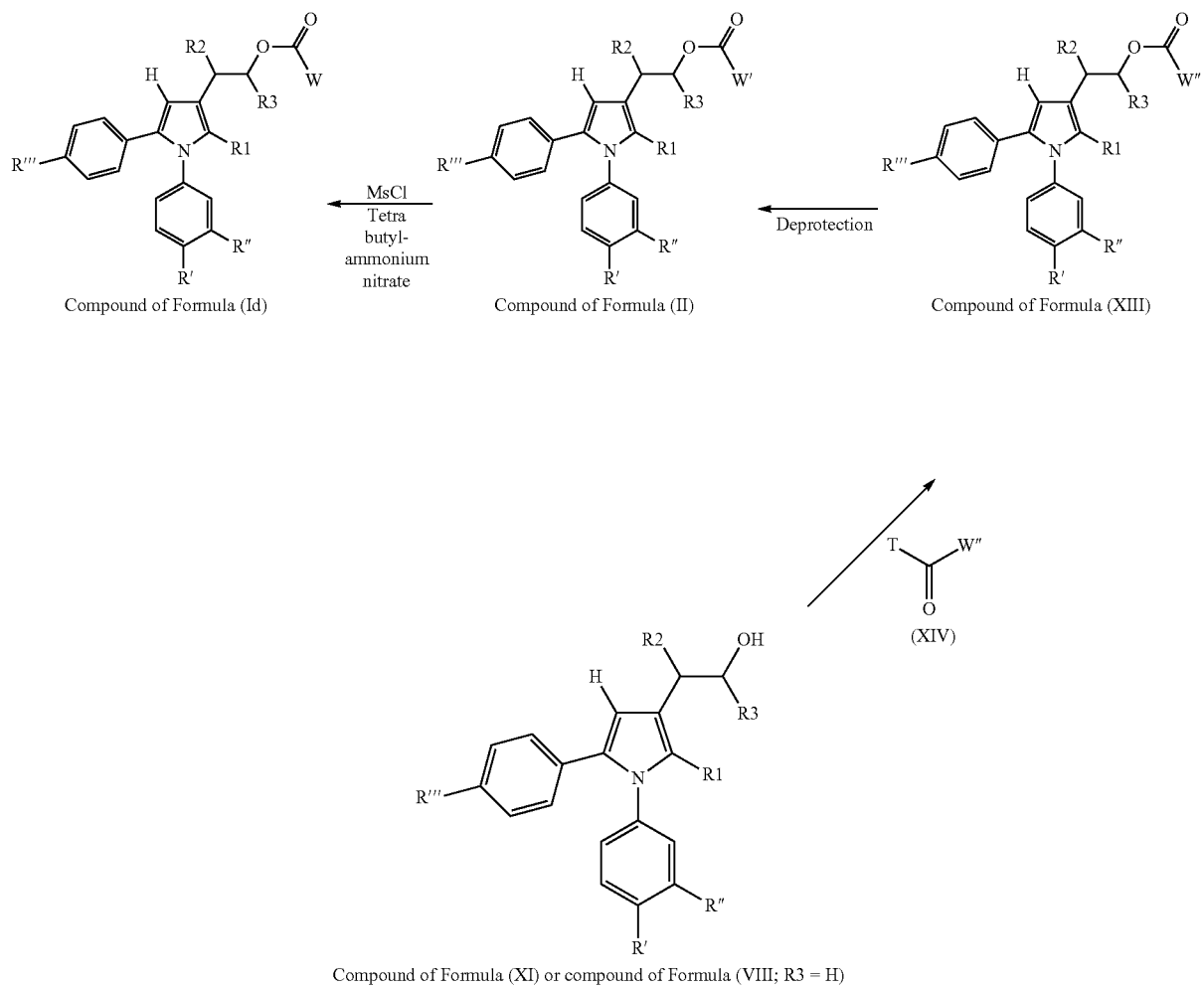

Where the substituents have the meanings discussed previously and T can be —OH, —Cl, —Br. The compounds of formula (XIV) are hydroxy acids optionally protected at the hydroxyl(s) or acyl halides (T=—Cl, —Br) of said protected hydroxy acids. The reaction of a compound of formula (XIV) with a compound of formula (XI) or (VIII), when T=—OH, is carried out in the presence of a condensing agent such as EDC or carbonyldiimidazole. When T is a halogen, the reaction is carried out in the presence of a base (e.g.: pyridine, triethylamine, n-methylmorpholine). Alternatively, a compound of formula (I-d) is prepared by reacting a compound of formula (XI) or (VIII) with the appropriate nitroxy acid (XV) in the presence of a condensing agent such as EDC or carbonyldiimidazole. The following nitroxy acids are known: 2-(nitroxyacetic) acid, 3-(nitrooxy) propanoic acid and are prepared as described (J. Org. Chem., 1956, 21, 367). A compound of formula (I-e) is prepared by reacting a nitroxy acid (XV) with a compound of formula (XVI) (Scheme 9), said reaction being carried out in the presence of a condensing agent such as for example EDC. Depending on the meaning of $R_3$, the compound of formula (XVI) can be obtained: if $R_3$=—H, from a compound of formula (VIII) as described in WO2008014821, if $R_3$ is an alkyl the compound of formula (XVI) is obtained by reductive amination of the compound of formula (XVII) or by transformation of this ketone to the corresponding oxime and subsequent reduction. The compound of formula (XVII) is obtained by oxidation of a compound of formula (XI) (scheme 8). The oxidation reaction is carried out according to known techniques, such as Swern or Moffat oxidation, or using pyridinium chloro-chromate.

Scheme 9

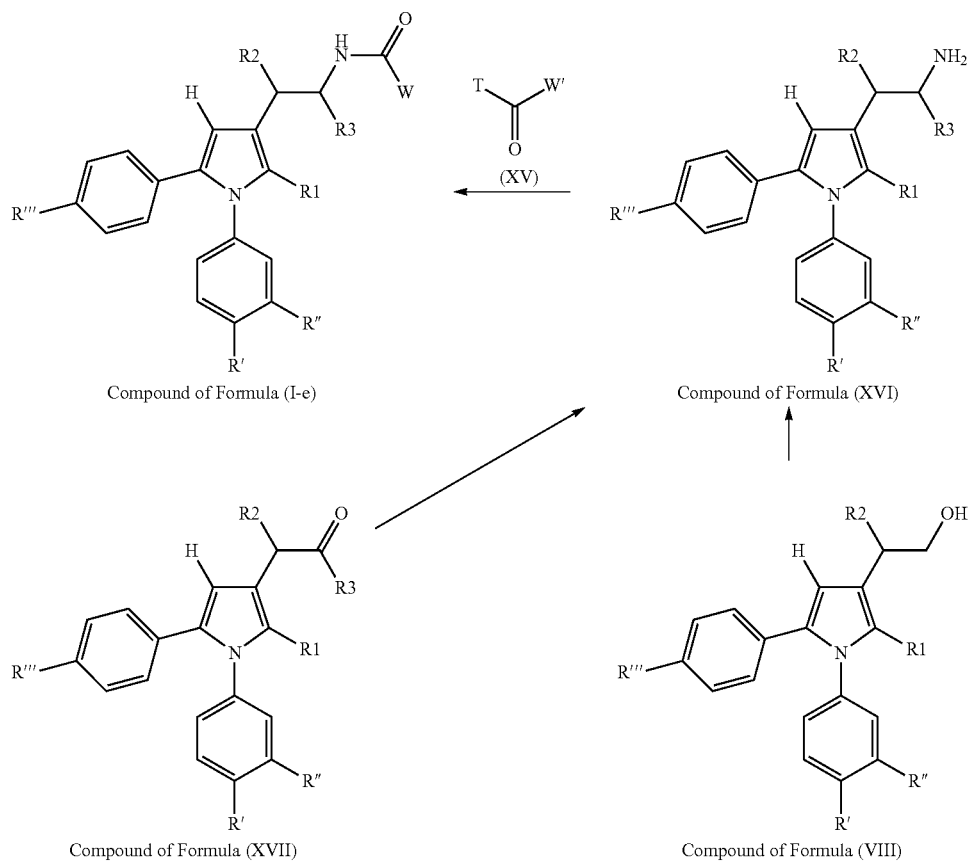

Examples of Preparation of the Compounds of the Invention

Representative examples of preparations of compounds of formula (III) are presented below:

2-[1-(4-Fluorophenyl)-2-methyl-5-(4-methylsulphonylphenyl)-1H-pyrrol-3-yl]acetic Acid (6g)

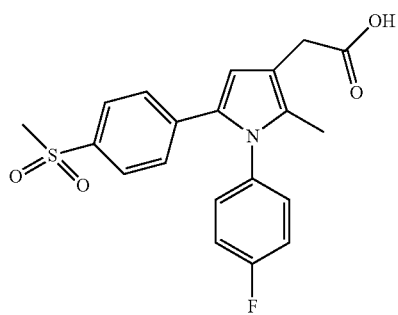 [SMILES: Cc1c(CC(=O)O)cc(-c2ccc(S(C)(=O)=O)cc2)n1-c1ccc(F)cc1]

Obtained by hydrolysis (NaOH aq. 10%, EtOH, 40° C., 3 h, yield 98%) of the corresponding ethyl ester. $^1$H NMR 300 MHz, DMSO-$d_6$: δ 2.07 (s, 3H), 3.01 (s, 3H), 3.56 (s, 2H), 6.50 (s, 1H), 7.08-7.17 (m, 6H), 7.68 (d, J=9.00 Hz, 2H), 11.20 (s, 1H). MS (ES): 388.3 (M+1); m.p.: 195-197° C. The ethyl ester is obtained by reduction of the corresponding glyoxylate (4, scheme 2), by reaction with triethylsilane in trifluoroacetic acid (yield 89%) $^1$H NMR 300 MHz, DMSO-$d_6$: δ 1.30 (t, J=15.00 Hz, 3H), 2.07 (s, 3H), 3.03 (s, 3H), 3.50 (s, 2H), 4.20 (q, J=15.00 Hz, 2H), 6.50 (s, 1H), 7.09-7.27 (m, 6H), 7.68 (t, J=6.00 Hz, 2H). MS (ES): 416.9 (M+1). The glyoxylate ($^1$H NMR, DMSO-$d_6$: δ 1.31 (t, J=12.00 Hz, 3H), 2.42 (s, 3H), 3.17 (s, 3H), 4.36 (q, J=21.00 Hz, 2H), 7.00 (s, 1H), 7.28-7.47 (m, 6H), 7.75 (d, J=9.00 Hz, 2H); MS (ES): 430.9 (M+1) is obtained by acylation with 1-(4-fluorophenyl)-2-methyl-5-(4-methylsulphonylphenyl)-1H-pyrrole ethoxalyl chloride, in DCM, at 0° C., in the presence of TiCl$_4$ (yield 92%), similarly to what was described in WO2008014821.

2-[1-(4-Thiomethylphenyl)-2-methyl-5-(4-methylsulphonylphenyl)-1H-pyrrol-3-yl]acetic Acid (6h)

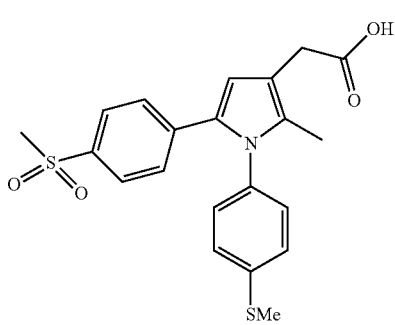 [SMILES: CSc1ccc(-n2c(-c3ccc(S(C)(=O)=O)cc3)cc(CC(=O)O)c2C)cc1]

Obtained by hydrolysis (NaOH aq. 10%, EtOH, 40° C., 3 h, yield 98%) of the corresponding ethyl ester. $^1$H NMR 400

MHz, CDCl₃: δ 2.09 (s, 3H), 3.08 (s, 3H), 3.40 (s, 3H), 3.50 (s, 2H), 6.52 (s, 1H), 7.08-7.20 (m, 6H), 7.71 (d, J=9.00 Hz, 2H), 11.40 (s, 1H). m.p.: 180° C. The ethyl ester is obtained by reduction of the corresponding glyoxylate (4, scheme 2), by reaction with triethylsilane in trifluoroacetic acid (yield 89%); $^1$H NMR 400 MHz, CDCl₃: δ 1.32 (t, J=15.00 Hz, 3H), 2.10 (s, 3H), 3.03 (s, 3H), 3.41 (s, 3H), 3.51 (s, 2H), 4.21 (q, J=15.00 Hz, 2H), 6.47 (s, 1H), 7.09-7.29 (m, 6H), 7.70 (t, J=6.00 Hz, 2H). The glyoxylate is obtained by acylation with 1-(4-fluorophenyl)-2-methyl-5-(4-methylsulphonylphenyl)-1H-pyrrole ethoxalyl chloride, in DCM, at 0° C., in the presence of TiCl₄ (yield 91%), similarly to what was described in WO2008014821. ($^1$H NMR, CDCl₃: δ 1.31 (t, J=12.00 Hz, 3H), 2.45 (s, 3H), 3.22 (s, 3H), 3.40 (s, 3H), 4.36 (q, J=21.00 Hz, 2H), 7.02 (s, 1H), 7.28-7.47 (m, 6H), 7.75 (d, J=9.00 Hz, 2H))

2-[1-(4-Fluorophenyl)-2-trifluoromethyl-5-(4-methylsulphonylphenyl)-1H-pyrrol-3-yl]acetic Acid (6i)

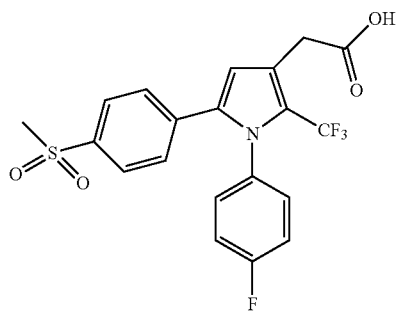 [SMILES: CS(=O)(=O)c1ccc(-c2cc(CC(=O)O)c(C(F)(F)F)n2-c2ccc(F)cc2)cc1]

Obtained by hydrolysis of the corresponding ethyl ester, at yield of 68%. $^1$H NMR (400 MHz, DMSO-d₆): δ 3.21 (s, 3H), 3.40 (s, 2H), 6.93 (s, 1H), 7.21-7.23 (m, 2H), 7.38-7.39 (m, 2H), 7.43 (d, J=8.32 Hz, 2H), 7.82 (d, J=8.24 Hz, 2H), 12.39 (s, 1H). LCMS: 442 (M+1). The ethyl ester is obtained from the corresponding glyoxylate by reduction with triethylsilane in trifluoroacetic acid (yield 47%). The glyoxylate is obtained by acylation with 1-(4-fluorophenyl)-2-trifluoromethyl-5-(4-methylsulphonylphenyl)-1H-pyrrole ethoxalyl chloride, at a yield of 32%. $^1$H NMR (400 MHz, CDCl₃): δ 1.34 (t, J=7.16 Hz, 3H), 3.05 (s, 3H), 4.25 (q, J=7.08 Hz, 2H), 7.02-7.04 (m, 4H), 7.38 (d, J=8.16 Hz, 2H), 7.50 (s, 1H), 7.84 (d, J=8.12 Hz, 2H), LCMS: 484 (M+1). The pyrrole 3 (scheme 2) is obtained by cyclization of 1-(4-methylsulphonylphenyl)-5-trifluoromethyl-1,4-pentanedione with 4-fluoroaniline, in toluene under reflux (6h) with catalysis of p-toluenesulphonic acid (yield 60%). $^1$H NMR (400 MHz, DMSO-d₆): δ 3.21 (s, 3H), 6.73 (d, J=4.00 Hz, 1H), 6.99 (d, J=3.96 Hz, 1H), 7.31-7.31 (m, 2H), 7.40 (d, J=8.44 Hz, 2H), 7.46-7.47 (m, 2H), 7.80 (d, J=8.48 Hz, 2H). LCMS: 384 (M+1). The 1-(4-methylsulphonylphenyl)-5-trifluoromethyl-1,4-pentanedione is obtained by oxidation of the corresponding methylthio ether with oxone ($^1$H NMR (400 MHz, CDCl₃): δ 2.54 (s, 3H), 3.15 (t, J=5.92 Hz, 2H), 3.39 (t, J=6.28 Hz, 2H), 7.29 (d, J=8.52 Hz, 2H), 7.89 (d, J=8.72 Hz, 2H)), obtained by reaction (NaH, DMF, 0° C., 2 h then 12 h RT, yield 70%) of ethyl trifluoroacetoacetate with 4'-methylthio-2-bromoacetophenone followed by decarboxylation (LiCl, DMF, 140° C., 1 h, yield 40%).

(R,S)-2-Methoxy-2-[1-(3-fluorophenyl)-2-methyl-5-(4-methylsulphonylphenyl)-1H-pyrrol-3-yl]acetic Acid (6l)

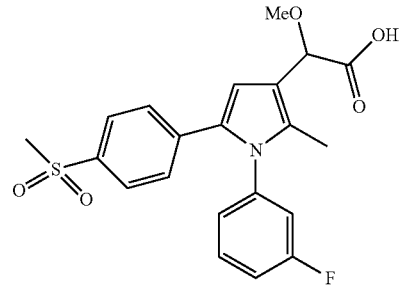 [SMILES: COC(C(=O)O)c1cc(-c2ccc(S(C)(=O)=O)cc2)n(-c2cccc(F)c2)c1C]

Obtained by hydrolysis of the corresponding ethyl ester. The ethyl ester is obtained from the corresponding glyoxyl ester (4, scheme 1). The glyoxyl ester (0.46 mmol) in CH₂Cl₂ is treated with ZnI₂ (0.217 mmol), and after 5 min NaBH₃CN (0.108 mmol) is added. Then it is stirred at RT for 2 h, then methanol is added, it is stirred for a further 30 min, and filtered on Celite. 10% NH₄Cl in 25 ml of 6N HCl is added to the filtrate. It is extracted with CH₂Cl₂, the combined organic fractions are washed with H₂O and then dried and concentrated. The residue is purified by chromatography (silica, hexane/EtOAc 1:1), m.p. 130° C., yield 54%. $^1$H NMR (CDCl₃): 7.72-7.66 (m, 2H), 7.38-7.35 (m, 1H), 7.00-7.25 (m, 3H), 6.88-6.91 (m, 2H), 6.55-6.57 (s, 1H), 4.79-4.82 (m, 1H), 4.23-4.27 (m, 2H), 3.43-3.45 (s, 3H) 3.00-2.96 (s, 3H), 2.12-2.16 (s, 3H), 1.28-1.58 (m, 3H).

(R,S)—N-Benzyloxycarbonyl-[2-amino-2-[1-(4-fluorophenyl)-2-methyl-5-(4-methylsulphonylphenyl)-1H-pyrrol-3-yl]]-acetic Acid (6m)

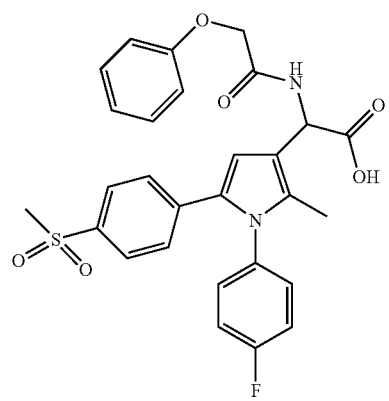 [SMILES: Cc1c(C(NC(=O)COc2ccccc2)C(=O)O)cc(-c2ccc(S(C)(=O)=O)cc2)n1-c1ccc(F)cc1]

A solution of (R,S)-ethyl-[2-amino-2-[1-(4-fluorophenyl)-2-methyl-5-(4-methanesulphonylphenyl)-1H-pyrrol-3-yl]]-acetate (5 g, 11.6 mmol) in DCM (75 mL) is treated with benzylchloroformate (1.98 g, 11.6 mmol) at 0° C. and stirred for 15-20 min. It is allowed to return to RT and it is stirred for 5 h, washed with H₂O, dried and concentrated, obtaining the ester, which is purified by chromatography (silica, EtOAc/hexane (1:20)). 2 g of oil is obtained (31%). $^1$H NMR 400 MHz, DMSO-d₆, δ 1.17 (t, J=4.00 Hz, 3H), 2.04 (s, 3H), 3.15

(s, 3H), 4.16 (q, J=4.00 Hz, 2H), 5.10 (s, 2H), 5.18 (d, J=8.00 Hz, 2H), 7.16 (d, J=8.00 Hz, 2H), 7.30-7.37 (m, 9H), 7.70 (d, J=8.40 Hz, 2H), 8.06 (d, J=8.00 Hz, 1H), MS: 565 (M+H).

The ester (2 g, 0.35 mmol) in EtOH (20 mL) is treated with NaOH (0.24 g, 0.6 mmol) in 3 mL of $H_2O$. It is stirred at RT for 16 h, diluted with $H_2O$, the pH is adjusted to 1-2 with 1N HCl, and it is extracted with acetate. The extracts are washed with $H_2O$, dried and concentrated, and the residue is purified by chromatography (silica, EtOAc/hexane (1:20)), obtaining 1.8 g (95%). $^1$H NMR 400 MHz, DMSO-$d_6$, ppm: 2.07 (s, 3H), 3.16 (s, 3H), 5.07 (s, 2H), 5.11 (d, J=8.00 Hz, 1H), 6.65 (s, 1H), 7.18 (d, J=8.40 Hz, 2H), 7.30-7.38 (m, 9H), 7.71 (d, J=8.00 Hz, 2H), 7.87 (d, J=8.00 Hz, 1H), 12.88 (s, 1H), LCMS: 537 (M+H).

Ethyl (R,S)-[2-amino-2-[1-(4-fluorophenyl)-2-methyl-5-(4-methylsulphonylphenyl)-1H-pyrrol-3-yl]]-acetate Ethyl-2-hydroxy-imino-2-[1-(4-fluorophenyl)-2-methyl-5-(4-methylsulphonylphenyl)-1H-pyrrol-3-yl]]-acetate, 20 g, is dissolved in ethanol (100 mL) and formic acid (100 mL), at 0° C., Zn powder (16.4 g) is added in 1 h. It is allowed to return to RT and it is stirred for 20 h. The salts are filtered and the filtrate is concentrated, the residue is dissolved in $H_2O$, it is made basic with soda to pH 10, and is extracted with DCM. It is dried and concentrated and the residue is purified by chromatography (silica, MeOH/DCM (1:20) to give the desired compound (10 g). $^1$H NMR 400 MHz, DMSO-$d_6$, ppm: 1.18 (t, J=4.00 Hz, 3H), 2.05 (s, 3H), 3.16 (s, 3H), 4.04-4.15 (m, 2H), 4.46 (s, 1H), 6.59 (s, 1H), 7.19 (d, J=8.00 Hz, 2H), 7.30-0.00 (m, 4H), 7.73 (d, J=40.00 Hz, 2H).

Ethyl-2-hydroxy-imino-2-[1-(4-fluorophenyl)-2-methyl-5-(4-methylsulphonylphenyl)-1H-pyrrol-3-yl]]-acetate

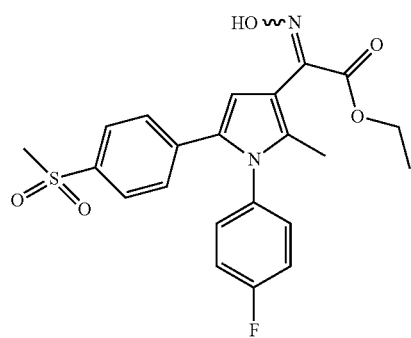 [SMILES: CCOC(=O)C(=NO)c1cc(-c2ccc(S(C)(=O)=O)cc2)n(-c2ccc(F)cc2)c1C]

Hydroxylamine hydrochloride (6.1 g, 8.74 mmol) and NaOAc (12 g, 0.15 mol) are added to ethyl-[1-(4-fluorophenyl)-2-methyl-5-(4-methylsulphonylphenyl)-1H-pyrrol-3-yl]]-glyoxylate (25 g, 5.8 mmol) in EtOH (200 mL) and dioxane (100 mL), it is heated at 90° C. for 40 h, it is concentrated and the residue is distributed between acetate (500 mL) and $H_2O$ (300 mL), the organic phase is washed with $H_2O$, dried and concentrated to give the oxime (20 g, 77.5%). $^1$H NMR 300 MHz, DMSO-$d_6$, ppm: 1.18 (t, J=9.00 Hz, 3H), 2.05 (s, 3H), 3.14 (s, 3H), 4.04-4.18 (m, 2H), 5.09 (d, J=6.00 Hz, 1H), 5.67 (d, J=6.00 Hz, 1H), 6.55 (s, 1H), 7.18 (d, J=6.00 Hz, 2H), 7.30-0.00 (m, 4H), 7.73 (d, J=21.00 Hz, 2H) MS: 445 (M+H).

(+)-N-Benzyloxycarbonyl-[2-amino-2-[1-(4-fluorophenyl)-2-methyl-5-(4-methylsulphonylphenyl)-1H-pyrrol-3-yl]]-acetic Acid [(+)6m]

The enantiomers of the amino acids are separated by preparative HPLC on a chiral stationary phase, column: Chiralcel OJ-H 9250×4.6 mm, mobile phase: 0.1% $CF_3COOH$ in hexane/ethanol (70:30), flow: 1.0 ml/min. The (+) isomer is eluted first, Rt: approx. 24 min, $[\alpha]_D^{25°}$: +78.74° (c=1.0 in $CHCl_3$, enantiomeric excess: >99.2% (HPLC)); Purity (HPLC): >97.9%; column: YMC Pack pro C18 (250×4.6; 5 μm), eluent 10 mM $NH_4OAc$ in $H_2O$ (A)/acetonitrile (B), t=0, B=30%, t=15 min B=100%, t=20 min B=100%.

(−)-N-Benzyloxycarbonyl-[2-amino-2-[1-(4-fluorophenyl)-2-methyl-5-(4-methylsulphonylphenyl)-1H-pyrrol-3-yl]]-acetic Acid [(−)6m]

Obtained as described above, eluted second, Rt: approx. 30 min. $[\alpha]_D^{25}$: −81.35° (C=1.0 in $CHCl_3$, enantiomeric excess >99.3%), HPLC purity: >93%.

(R,S)—N-(Benzyloxycarbonyl)-2-amino-2-[1-(3-fluorophenyl)-2-methyl-5-(4-methylsulphonyl phenyl)-1H-pyrrol-3-yl-acetic Acid (6n)

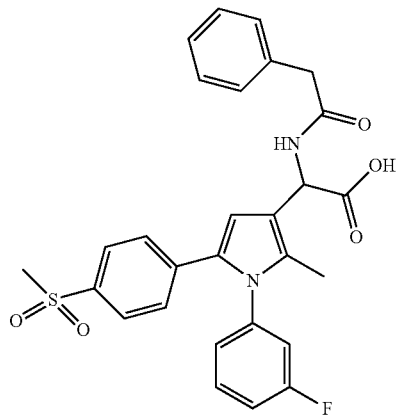 [SMILES: Cc1c(C(NC(=O)Cc2ccccc2)C(=O)O)cc(-c2ccc(S(C)(=O)=O)cc2)n1-c1cccc(F)c1]

Obtained similarly to as described for 6m, yield 95%, m.p. 127° C. $^1$H NMR (400 MHz, DMSO-$d_6$) ppm: 12.88 (s, 1H) 7.87 (d, 1H), 7.71 (d, 2H), 7.35 (m, 9H), 7.18 (d, 2H), 6.65 (s, 1H), 5.11 (d, 1H), 5.07 (s, 2H), 3.16 (s, 3H), 2.07 (s, 3H).

(R,S)-Ethyl-N-(benzyloxycarbonyl)-2-amino-2-[1-(3-fluorophenyl)-2-methyl-5-(4-methylsulphonylphenyl)-1H-pyrrol-3-yl]-acetate Obtained similarly to 6m, yield 31%, m.p. 95° C. $^1$H NMR (400 MHz, DMSO-$d_6$) ppm: 8.06 (d, 1H), 7.70 (d, 2H), 7.36 (m, 9H), 7.16 (d, 2H), 5.18 (d, 2H), 5.10 (s, 2H), 4.16 (q, 2H), 3.15 (s, 3H), 2.04 (s, 3H), 1.17 (t, 3H).

(R,S)-Ethyl-2-amino-2-[1-(3-fluorophenyl)-2-methyl-5-(4-methylsulphonylphenyl)-1H-pyrrol-3-yl]-acetate Obtained similarly to 6m, yield 47%, m.p. 110° C. $^1$H NMR (400 MHz, DMSO-$d_6$) ppm: 7.73 (d, 2H) 7.32 (m, 4H), 7.19 (d, 2H), 6.59 (s, 1H), 4.46 (s, 1H), 4.09 (m, 2H), 3.16 (s, 3H), 2.05 (s, 3H), 1.18 (t, 3H).

(R,S)-Ethyl-2-[1-(3-fluorophenyl)-2-methyl-5-(4-methylsulphonylphenyl)-1H-pyrrol-3-yl]-2-(hydroxylamino)ylidene-acetate

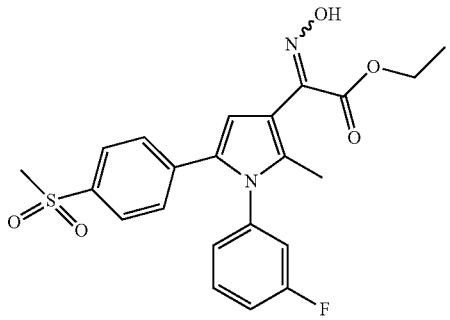 [SMILES: CCOC(=O)C(=NO)c1cc(-c2ccc(S(C)(=O)=O)cc2)n(-c2cccc(F)c2)c1C]

Obtained similarly to 6m, yield 77.5%, m.p. 101° C. $^1$H NMR (400 MHz, DMSO-d6) ppm: 7.73 (d, 2H). 7.33 (m, 4H), 7.18 (d, 2H), 6.55 (s, 1H), 5.67 (d, 1H), 5.09 (d, 1H), 4.18 (m, 2H), 3.14 (s, 3H), 2.05 (s, 3H), 1.18 (t, 3H).

(R,S)—N-Methyl-2-amino-2-[1-(4-fluorophenyl)-2-methyl-5-(4-methylsulphonylphenyl)-1H-pyrrol-3-yl-acetic Acid (6o)

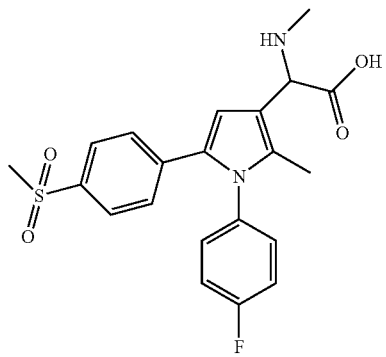 [SMILES: CNC(C(=O)O)c1cc(-c2ccc(S(C)(=O)=O)cc2)n(-c2ccc(F)cc2)c1C]

The BOC-protected derivative described hereunder (800 mg, 0.15 mmol) in EtOH (10 ml) is stirred at RT with 6N HCl (10 ml). It is concentrated, the residue is taken up in EtOAc, obtaining the desired product, at a yield of 75%. $^1$H NMR 400 MHz, DMSO-d6: δ 1.75 (s, 3H), 2.34 (d, J=4.00 Hz, 3H), 3.20 (s, 3H), 4.97 (s, 1H), 6.64 (s, 1H), 7.20 (d, J=8.00 Hz, 2H), 7.34-7.36 (m, 4H), 7.74 (d, J=11.20 Hz, 2H).
MS: 415.2 (M+H).

(R,S)—N-Methyl-N-tert-butoxycarbonyl-2-amino-2-[1-(4-fluorophenyl)-2-methyl-5-(4-methylsulphonylphenyl)-1H-pyrrol-3-yl]-acetic Acid (6p)

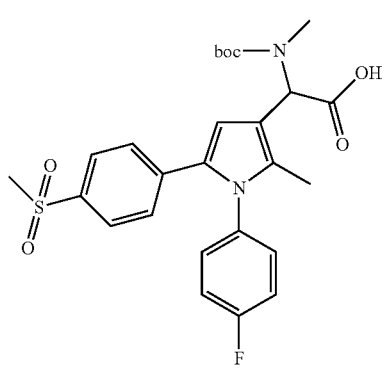

Obtained from the corresponding N-methylamino acid by treatment with BOC-anhydride in MeOH at RT for 20 h. The amino acid is obtained by hydrolysis with NaOH/EtOH of ethyl (R,S)—N-methyl-N-trifluoroacetyl-2-amino-2-[1-(4-fluorophenyl)-2-methyl-5-(4-methylsulphonylphenyl)-1H-pyrrol-3-yl]-acetate obtained by treatment of ethyl (R,S)—N-trifluoroacetyl-2-amino-2-[1-(4-fluorophenyl)-2-methyl-5-(4-methylsulphonylphenyl)-1H-pyrrol-3-yl]-acetate with NaH/CH$_3$I in THF (0° C., 2 h), yield 65%. $^1$H NMR 400 MHz, DMSO-d$_6$: δ 1.22 (t, J=8.00 Hz, 3H), 1.96 (s, 3H), 2.91 (s, 3H), 3.16 (s, 3H), 4.24 (q, J=8.00 Hz, 2H), 5.99 (s, 1H), 6.57 (s, 1H), 7.23 (d, J=8.00 Hz, 2H), 7.33-7.35 (m, 4H), 7.70 (d, J=8.00 Hz, 2H).

Representative examples of preparations of the compounds of formula (I) and (II) are presented below:

Example 1

2-(Nitrooxy)ethyl-2-[1-phenyl-2-methyl-5-(4-methylsulphonylphenyl)-1H-pyrrol-3-yl]acetate Tetrabutylammonium nitrate (0.9 mmol) is added to a solution of the mesylate described below (0.3 mmol) in toluene (5 ml), the resultant solution is heated under reflux for 1 h. Then H$_2$O and ethyl ether are added, the phases are separated, the organic phase is washed with NaCl s.s. and then with H$_2$O. The organic phase is dried and concentrated. The raw product is purified by chromatography (silica, hexane/EtOAc), m.p. 124-126° C., yield 69%. $^1$H NMR 200 MHz (CDCl$_3$) δ (ppm): 2.04 (s, 3H), 2.96 (s, 3H), 3.53 (s, 2H), 4.37-4.42 (m, 2H), 4.67-4.70 (m, 2H), 6.48 (s, 1H), 7.11-7.15 (m, 4H), 7.36-7.40 (m, 3H), 7.63 (d, 2H, J=8.6). MS-ESI: m/z 481 (M+Na$^+$).

2-(Methylsulphonyloxy)ethyl-2-[1-phenyl-2-methyl-5-(4-methylsulphonylphenyl)-1H-pyrrol-3-yl)acetate DMAP (0.03 mmol) and diisopropylethylamine (DPEA) (0.5 mmol) are added to a solution of 2-hydroxyethyl-2-[1-phenyl-2-methyl-5-(4-methylsulphonylphenyl)-1H-pyrrol-3-yl)acetate in DCM (10 ml), at 0° C., MsCl (0.6 mmol) is added and it is stirred for 3 h, at RT. Then H$_2$O is added (5 ml) and it is stirred for 1 h, the phases are separated and the organic phase is washed with NaHCO$_3$ and then with H$_2$O. It is dried and concentrated. The raw product is purified by chromatography (silica; hexane/EtOAc). Oil, yield 76%. $^1$H NMR 200 MHz (CDCl$_3$) δ (ppm): 2.05 (s, 3H), 2.96 (s, 6H), 3.50 (s, 2H), 4.13-4.33 (m, 4H), 6.51 (s, 1H), 7.08-7.14 (m, 4H), 7.37-7.41 (m, 3H), 7.62 (d, 2H, J=8.6). MS-ESI: m/z 515 (M+Na$^+$).

Example 1-II

2-Hydroxyethyl-2-[1-phenyl-2-methyl-5-(4-methylsulphonylphenyl)-1H-pyrrol-3-yl)]acetate Ethanediol (0.9 mmol) and DMAP (0.3 mmol) are added to a solution of acid 6a (0.3 mmol) in DCM (15 ml). After 5 minutes, a solution of EDC (0.6 mmol) in DCM (5 ml) is added. It is stirred for 3 hours at RT, then washed with NaCl s.s. and with H$_2$O. The organic phase is dried and concentrated. The raw product is purified by chromatography (silica, hexane/EtOAc), yield 60%, m.p. 121-123° C., $^1$H NMR 200 MHz (CDCl$_3$) δ (ppm): 2.05 (s, 3H), 2.96 (s, 3H), 3.54 (s, 2H), 3.82 (br s, 1H), 4.11-4.27 (m, 4H), 6.50 (s, 1H), 7.09-7.14 (m, 4H), 7.35-7.40 (m, 3H), 7.62 (d, 2H, J=8.6). MS-ESI: m/z 436 (M+Na$^+$).

Example 2

2-(Nitrooxy)ethyl-2-[(1-(4-fluorophenyl)-2-methyl-5-(4-(methylsulphonyl)phenyl)-1H-pyrrol-3-yl)]acetate Prepared from the mesylate described below similarly to example 1, yield 61%, m.p. 110-112° C., $^1$H NMR 200 MHz (CDCl$_3$) δ (ppm): 2.03 (s, 3H), 2.98 (s, 3H), 3.52 (s, 2H), 4.38-4.40 (m, 2H), 4.67-4.69 (m, 2H), 6.47 (s, 1H), 7.06-7.15 (m, 6H), 7.64 (d, 2H, J=8.6). MS-ESI: m/z 499 (M+Na$^+$).

2-(Methylsulphonyloxy)ethyl-2-[1-(4-fluorophenyl)-2-methyl-5-(4-(methylsulphonyl)phenyl)-1H-pyrrol-3-yl]acetate Prepared similarly to example 1, oil, (yield 80%). $^1$H NMR 200 MHz (CDCl$_3$) δ (ppm): 2.04 (s, 3H), 2.95 (s, 6H), 3.53 (s, 2H), 4.08-4.25 (m, 4H), 6.54 (s, 1H), 7.09-7.18 (m, 6H), 7.61 (d, 2H, J=8.2). MS-ESI: m/z 533 (M+Na$^+$).

Example 2-II

2-Hydroxyethyl-[2-(1-(4-fluorophenyl)-2-methyl-5-(4-methylsulphonylphenyl)-1H-pyrrol-3-yl)]acetate Prepared from acid 6g similarly to example 1-II, yield 64%, m.p. 129-131° C., $^1$H NMR 200 MHz (CDCl$_3$) δ (ppm): 2.01 (s, 3H), 2.99 (s, 3H), 3.50 (s, 2H), 3.80 (br s, 1H), 4.10-4.28 (m, 4H), 6.52 (s, 1H), 7.08-7.17 (m, 6H), 7.68 (d, 2H, J=8.3). MS-ESI: m/z 454 (M+Na$^+$).

Example 3

2-(Nitrooxy)ethyl-2-[(1-(3-fluorophenyl)-2-methyl-5-(4-methylsulphonylphenyl)-1H-pyrrol-3-yl)]acetate Obtained from acid 6d and 2-nitroxy ethanol similarly to example 8, yield 90%, m.p. 130° C. FT-IR cm$^{-1}$: 1738 (ν C—O), 1280 (ν$_{as}$C—O—C), 1144 (ν$_s$C—O—C), 1625 (ν$_{as}$O—NO$_2$), 843 (ν$_s$O—NO$_2$). $^1$H NMR (400 MHz, CDCl$_3$): δ 7.68 (d, 2H), 7.37 (m, 1H), 7.15 (m, 3H), 6.90 (m, 2H), 6.50 (s, 1H), 4.78 (m, 2H), 4.40 (m, 2H), 3.50 (s, 2H), 3.00 (s, 3H), 2.10 (s, 3H).

Example 3-II

2-(Hydroxy)ethyl-2-[(1-(3-fluorophenyl)-2-methyl-5-(4-(methylsulphonyl)phenyl)-1H-pyrrol-3-yl)acetate Obtained from 6d and ethanediol similarly to example 8-II, yield 66%, m.p. 115° C. $^1$H NMR (400 MHz, CDCl$_3$): δ 7.68 (d, 2H), 7.37 (m, 1H), 7.15 (m, 3H), 6.90 (m, 2H), 6.50 (s, 1H), 4.58 (m, 2H), 4.40 (m, 2H), 3.50 (s, 2H), 3.00 (s, 3H), 2.10 (s, 3H), 2.08 (s broad, 1H).

Example 4

2-(Nitrooxy)ethyl-[1-(4-methoxy-phenyl)-2-methyl-5-(4-methylsulphonylphenyl)-1H-pyrrol-3-yl]-acetate Obtained from 6c and 2-nitroxy ethanol similarly to example 8, yield 40%, m.p. 122° C. FT-IR cm$^{-1}$: 1738 (ν C—O), 1280 (ν$_{as}$C—O—C), 1144 (ν$_s$C—O—C), 1625 (ν$_{as}$O—NO$_2$), 843 (ν$_s$O—NO$_2$). $^1$H NMR (400 MHz, CDCl$_3$): δ 7.70 (d, 2H), 7.19 (d, 2H), 7.10 (d, 2H), 6.89 (d, 2H), 6.50 (s, 1H), 4.73 (t, 2H), 4.47 (t, 2H), 3.60 (s, 3H), 3.50 (s, 2H), 3.00 (s, 3H), 2.10 (s, 3H).

Example 4-II

2-(Hydroxy)ethyl-[1-(4-methoxyphenyl)-2-methyl-5-(4-methylsulphonylphenyl)-1H-pyrrol-3-yl]-acetate Obtained from 6c similarly to example 8-II, yield 53%, m.p. 105° C. $^1$H NMR (400 MHz, CDCl$_3$): δ 7.60 (d, 2H), 7.18 (d, 2H), 7.00 (d, 2H), 6.96 (d, 2H), 6.43 (s, 1H), 4.65 (t, 2H), 4.32 (t, 2H), 3.58 (s, 3H), 3.47 (s, 2H), 2.40 (s broad, 1H), 2.37 (s, 3H), 2.01 (s, 3H).

Example 5

2-(Nitroxy)ethyl-[1-(4-methylthiophenyl)-2-methyl-5-(4-methylsulphonylphenyl)-1H-pyrrol-3-yl]-acetate Obtained from the corresponding mesylate similarly to example 1, yield 70%, m.p. 123° C., FT-IR cm$^{-1}$: 1738 (ν C—O), 1280 (ν$_{as}$C—O—C), 1144 (ν$_s$C—O—C), 1625 (ν$_{as}$O—NO$_2$), 843 (ν$_s$O—NO$_2$). $^1$H NMR (400 MHz, CDCl$_3$): δ 7.80 (d, 2H), 7.40 (d, 2H), 7.00 (d, 2H), 6.98 (d, 2H), 6.50 (s, 1H), 4.73 (t, 2H), 4.47 (t, 2H), 3.88 (s, 3H), 3.50 (s, 2H), 3.00 (s, 3H), 2.10 (s, 3H).

Example 5-II

2-Hydroxyethyl-[1-(4-methylthiophenyl)-2-methyl-5-(4-methylsulphonylphenyl)-1H-pyrrol-3-yl]-acetate Prepared from acid 6h and ethanediol, similarly to example 1-II, yield 65%, m.p. 116-118° C. $^1$H NMR (400 MHz, CDCl$_3$): δ 2.06-2.15 (m, 5H), 2.97 (s, 3H), 3.51 (s, 2H), 4.23 (t, 2H, J=6.0), 4.52 (t, 2H, J=6.4), 6.49 (s, 1H), 7.12-7.16 (m, 4H), 7.38-7.40 (m, 3H), 7.62 (d, 2H, J=8.5). MS-ESI: m/z 495 (M+Na$^+$).

Example 6

3-(Nitrooxy)-propyl-[2-[1-phenyl-2-methyl-5-(4-methylsulphonylphenyl)-1H-pyrrol-3-yl)]]acetate Prepared similarly to example 1, yield 65%, m.p. 116-118° C., $^1$H NMR 200 MHz (CDCl$_3$) δ: 2.06-2.15 (m, 5H), 2.97 (s, 3H), 3.51 (s, 2H), 4.23 (t, 2H, J=6.0), 4.52 (t, 2H, J=6.4), 6.49 (s, 1H), 7.12-7.16 (m, 4H), 7.38-7.40 (m, 3H), 7.62 (d, 2H, J=8.5). MS-ESI: m/z 495 (M+Na$^+$).

Example 6-II

3-Hydroxypropyl-2-[1-phenyl-2-methyl-5-(4-methylsulphonylphenyl)-1H-pyrrol-3-yl]acetate Prepared from 6a and 1,3-propanediol similarly to example 1-II, yield 55%, m.p. 108-110° C. $^1$H NMR 200 MHz (CDCl$_3$) δ: 1.83 (br s, 1H), 1.86-1.95 (m, 2H), 2.06 (s, 3H), 2.97 (s, 3H), 3.52 (s, 2H), 3.65-3.73 (m, 2H), 4.28 (t, 2H, J=6.2), 6.50 (s, 1H), 7.12-7.16 (m, 4H), 7.37-7.40 (m, 3H), 7.62 (d, 2H, J=8.4). MS-ESI: m/z 450 (M+Na$^+$).

Example 7

3-(Nitrooxy)propyl 2-[1-(4-fluorophenyl)-2-methyl-5-(4-methylsulphonylphenyl)-1H-pyrrol-3-yl]acetate

Prepared similarly to example 1, yield 69%, m.p. 126-128° C., $^1$H NMR 200 MHz (CDCl$_3$) δ: 2.00-2.13 (m, 5H), 2.96 (s, 3H), 3.49 (s, 2H), 4.21 (t, 2H, J=6.0), 4.51 (t, 2H, J=6.4), 6.47 (s, 1H), 7.06-7.15 (m, 6H), 7.64 (d, 2H, J=8.6). MS-ESI: m/z 491 (M+H$^+$).

3-(Methylsulphonyloxy)propyl-2-[1-(4-fluorophenyl)-2-methyl-5-(4-methylsulphonylphenyl)-1H-pyrrol-3-yl]acetate

Oil, yield 75%. $^1$H NMR 200 MHz (CDCl$_3$) δ (ppm): 1.82-1.92 (m, 2H), 2.03 (s, 3H), 2.95 (s, 6H), 3.54 (s, 2H), 3.63-3.75 (m, 2H), 4.28 (t, 2H, J=6.2), 6.53 (s, 1H), 7.15-7.21 (m, 6H), 7.62 (d, 2H, J=8.4). MS-ESI: m/z 547 (M+Na$^+$).

Example 7-II

3-Hydroxypropyl-2-[(1-(4-fluorophenyl)-2-methyl-5-(4-methylsulphonylphenyl)-1H-pyrrol-3-yl]acetate

Prepared from 6g and 1,3-propanediol similarly to example 1-II, yield 65%, m.p. 112-115° C., $^1$H NMR 200 MHz (CDCl$_3$) δ: 1.80 (br s, 1H), 1.84-1.94 (m, 2H), 2.05 (s, 3H), 2.98 (s, 3H), 3.50 (s, 2H), 3.64-3.71 (m, 2H), 4.25 (t, 2H, J=6.2), 6.50 (s, 1H), 7.12-7.16 (m, 6H), 7.62 (d, 2H, J=8.0). MS-ESI: m/z 468 (M+Na$^+$).

Example 8

3-(Nitroxy)propyl-[1-(3-fluorophenyl)-2-methyl-5-(4-methylsulphonylphenyl)-1H-pyrrol-3-yl]-acetate

3-Nitrooxy-propan-1-ol (0.0012 mol), DMAP (0.0048 mol) are added to acid 6d (0.0012 mol) in DCM (3 ml) and stirred for 5 minutes. Then EDC is added (0.0024 mol) and it is stirred at RT for 3.5 h. It is poured into H$_2$O and extracted with DCM. The organic phase is washed with 2N HCl to pH 2, neutralized with NaHCO$_3$ s.s., and finally washed with H$_2$O. It is dried and concentrated. The residue is purified by chromatography (silica, chloroform/hexane/EtOAc (3:4:1), yield 92%, m.p. 125° C., FT-IR cm$^{-1}$: 1742 (vC—O), 1281 (v$_{as}$C—O—C), 1150 (v$_s$C—O—C), 1630 (v$_{as}$O—NO$_2$), 870 (v$_s$O—NO$_2$). $^1$H NMR (400 MHz, CDCl$_3$): δ 7.69 (d, 2H), 7.40 (m, 1H), 7.18 (d, 2H), 7.12 (m, 1H), 6.95 (m, 2H), 6.50 (s, 1H), 4.55 (t, 2H), 4.25 (t, 2H), 3.52 (s, 2H), 3.02 (s, 3H), 2.10 (m, 5H). 3-Nitrooxy-propan-1-ol: 3-bromopropanol (1.4 mmol) is added to AgNO$_3$ (5.7 mmol) in CH$_3$CN (8 ml), it is stirred for 24 h at RT, the solvent is concentrated, DCM (20 ml) is added, it is filtered on celite, the filtrate is dried and concentrated. The oil obtained is used as it is. $^1$H NMR (400 MHz CDCl$_3$): δ 4.59 (t, 2H), 3.75 (t, 2H), 1.96 (m, 2H), 1.64 (broad s, 1H). 3-Nitrooxy-propan-1-ol can also be prepared from 1,3-propanediol (0.022 mol) dissolved in ethyl acetate (50 ml), adding, at 0° C., HNO$_3$ at 65% (w/v) (0.016 mol, 1.55 ml), (CH$_3$CO)$_2$O (0.059 mol, 5.56 ml), glacial AcOH (0.097 mol, 5.56 ml). It is left to react at RT for 20 h. Then it is neutralized with 20% aqueous KOH and it is extracted with DCM, it is washed with H$_2$O and dried, the solvent is concentrated and the residue is purified by silica chromatography, EtOAc/hexane (1:3).

Example 8-II

3-Hydroxypropyl-[1-(3-fluorophenyl)-2-methyl-5-(4-methylsulphonylphenyl)-1H-pyrrol-3-yl]-acetate

Obtained from acid 6d and 1,3-propanediol similarly to example 1-II, yield 60%, m.p. 110° C., $^1$H NMR (400 MHz, CDCl$_3$): δ 7.68 (d, 2H), 7.37 (m, 1H), 7.15 (m, 3H), 6.90 (m, 2H), 6.50 (s, 1H), 4.24 (t, 2H), 4.12 (t, 2H), 3.50 (s, 2H), 3.00 (s, 3H), 2.50 (s, 3H), 2.10 (m, 2H), 1.50 (s broad, 1H).[1]

Example 9

3-(Nitroxy)propyl-[1-(4-methoxyphenyl)-2-methyl-5-(4-methylsulphonylphenyl)-1H-pyrrol-3-yl]-acetate

Obtained from acid 6c similarly to example 8, yield 52%, m.p. 115° C. FT-IR cm$^{-1}$: 1742 (vC—O), 1281 (v$_{as}$C—O—C), 1150 (v$_s$C—O—C), 1630 (v$_{as}$O—NO$_2$), 870 (v$_s$O—NO$_2$). $^1$H NMR (400 MHz, CDCl$_3$): δ 7.67 (d, 2H), 7.18 (d, 2H), 7.07 (d, 2H), 6.92 (d, 2H), 6.49 (s, 1H), 4.53 (t, 2H), 4.24 (t, 2H), 3.50 (s, 2H), 3.01 (s, 3H), 2.50 (s, 3H), 2.47 (s, 3H), 2.08 (m, 2H).

Example 9-II

3-Hydroxypropyl-[1-(4-methoxyphenyl)-2-methyl-5-(4-methylsulphonylphenyl)-1H-pyrrol-3-yl]-acetate

Obtained from acid 6c and 1,3-propanediol similarly to example 8, yield 37%, m.p. 103° C. $^1$H NMR (400 MHz, CDCl$_3$): δ 7.67 (d, 2H), 7.18 (d, 2H), 7.07 (d, 2H), 6.92 (d, 2H), 6.49 (s, 1H), 4.25 (t, 2H), 4.12 (t, 2H), 3.85 (s, 3H), 3.52 (s, 2H), 3.00 (s, 3H), 2.12 (m, 5H), 1.70 (s broad, 1H).

Example 10

3-(Nitroxy)propyl-[1-(4-methylthiophenyl)-2-methyl-5-(4-methylsulphonylphenyl)-1H-pyrrol-3-yl]-acetate

Obtained from acid 6h and 3-nitrooxy-propan-1-ol similarly to example 8, yield 55%, m.p. 118° C. FT-IR cm$^{-1}$: 1737 (v C—O), 1281 (v$_{as}$C—O—C), 1142 (v$_s$C—O—C), 1620 (v$_{as}$O—NO$_2$), 844 (v$_s$O—NO$_2$). $^1$H NMR (400 MHz, CDCl$_3$): δ 7.79 (d, 2H), 7.44 (d, 2H), 7.12 (d, 2H), 6.96 (d, 2H), 6.56 (s, 1H), 4.46 (t, 2H), 4.18 (t, 2H), 3.59 (s, 2H), 3.09 (s, 3H), 2.53 (s, 3H), 2.50 (s, 3H), 2.10 (m, 2H).

Example 10-II

3-(Hydroxy)propyl-[1-(4-methylthiophenyl)-2-methyl-5-(4-methylsulphonylphenyl)-1H-pyrrol-3-yl]-acetate

Obtained from 6h and 1,3-butanediol similarly to as described in example 1-II, yield 55%, m.p. 108° C., $^1$H NMR (400 MHz, CDCl$_3$): δ 7.79 (d, 2H), 7.44 (d, 2H), 7.12 (d, 2H), 6.96 (d, 2H), 6.46 (s, 1H), 4.26 (t, 2H), 4.08 (t, 2H), 3.39 (m, 2H), 3.09 (s, 3H), 2.50 (s, 3H), 2.19 (s, 3H), 2.09 (m, 2H), 2.02 (s broad, 1H).

Example 11

4-(Nitroxy)butyl-2-[1-(4-fluorophenyl)-2-methyl-5-(4-methylsulphonylphenyl)-1H-pyrrol-3-yl]acetate

Prepared similarly to example 1, yield 61%, m.p. 102-104° C., $^1$H NMR 200 MHz (CDCl$_3$) δ (ppm): 1.71-1.87 (m, 4H), 2.05 (s, 3H), 2.99 (s, 3H), 3.50 (s, 2H), 4.16 (t, 2H, J=5.7), 4.46 (t, 2H, J=6.0), 6.49 (s, 1H), 7.09-7.17 (m, 6H), 7.66 (d, 2H, J=8.6). MS-ESI: m/z 527 (M+Na$^+$).

4-(Methanesulphonyloxy)butyl-2-[1-(4-fluorophenyl)-2-methyl-5-(4-methylsulphonylphenyl)-1H-pyrrol-3-yl]acetate Oil, yield 80%. $^1$H NMR 200 MHz (CDCl$_3$) δ (ppm): 1.79-1.82 (m, 4H), 2.04 (s, 3H), 2.98 (s, 6H), 3.49 (s, 2H), 4.11-4.26 (m, 4H), 6.49 (s, 1H), 7.08-7.17 (m, 6H), 7.63 (d, 2H, J=8.3). MS-ESI: m/z 560 (M+Na$^+$).

Example 11-II 4-(Hydroxy)butyl-2-[1-(4-fluorophenyl)-2-methyl-5-(4-methylsulphonylphenyl)-1H-pyrrol-3-yl]acetate Prepared from 6g and 1,4-butanediol similarly to example 1-II, yield 66%, m.p. 149-151° C., $^1$H NMR 200 MHz (CDCl$_3$) δ (ppm): 1.57-1.65 (m, 2H), 1.68-1.75 (m, 2H), 2.02 (s, 3H), 2.97 (s, 3H), 3.46 (s, 2H), 3.62 (t, 2H, J=6.0), 4.15 (t, 2H, J=6.3), 6.45 (s, 1H), 7.11-7.15 (m, 6H), 7.60 (d, 2H, J=8.6). MS-ESI: m/z 482 (M+Na$^+$).

Example 12

4-(Nitrooxy)butyl-2-[1-(3-fluorophenyl)-2-methyl-5-(4-methylsulphonylphenyl)-1H-pyrrol-3-yl]acetate Obtained from 6d and 4-nitroxy butanol similarly to example 8, yield 72%, m.p. 114° C. FT-IR cm$^{-1}$: 1739 (ν C—O), 1279 (ν$_{as}$C—O—C), 1141 (ν$_s$C—O—C), 1619 (ν$_{as}$O—NO$_2$), 840 (ν$_s$O—NO$_2$). $^1$H NMR (400 MHz, CDCl$_3$) δ: 7.68 (d, 2H), 7.37 (m, 1H), 7.15 (m, 3H), 6.90 (m, 2H), 6.50 (s, 1H), 4.47 (t, 2H), 4.16 (t, 2H), 3.57 (s, 2H), 3.09 (s, 3H), 2.20 (s, 3H), 2.09 (m, 4H).

Example 12-II 4-(Nitrooxy)butyl-2-[1-(3-fluorophenyl)-2-methyl-5-(4-methylsulphonylphenyl)-1H-pyrrol-3-yl)acetate Obtained from 6d and 1,4-butanediol similarly to example 8-II, yield 55%, m.p. 103° C. $^1$H NMR (400 MHz, CDCl$_3$) δ: 7.67 (d, 2H), 7.18 (d, 2H), 7.07 (m, 1H), 6.92 (m, 3H), 6.49 (s, 1H), 4.40 (t, 2H), 4.16 (t, 2H), 3.57 (s, 2H), 3.09 (s, 3H), 2.20 (s, 3H), 2.10 (m, 4H), 2.02 (s broad, 1H).

Example 13

4-(Nitrooxy)butyl-2-[1-(4-methoxyphenyl)-2-methyl-5-(4-methylsulphonylphenyl)-1H-pyrrol-3-yl]acetate Obtained from 6c and 4-nitroxy butanol similarly to example 8, yield 30%, m.p. 109° C. FT-IR cm$^{-1}$: 1739 (ν C—O), 1279 (ν$_{as}$C—O—C), 1141 (ν$_s$C—O—C), 1619 (ν$_{as}$O—NO$_2$), 840 (ν$_s$O—NO$_2$). $^1$H NMR (400 MHz, CDCl$_3$): δ 7.70 (d, 2H), 7.22 (d, 2H), 7.10 (d, 2H), 7.00 (d, 2H), 6.52 (s, 1H), 4.50 (t, 2H), 4.16 (t, 2H), 3.57 (s, 2H), 3.09 (s, 3H), 2.50 (s, 3H), 2.53 (s, 3H), 2.09 (m, 4H).

Example 13-II 4-(Hydroxy)butyl-2-[1-(4-methoxyphenyl)-2-methyl-5-(4-methylsulphonylphenyl)-1H-pyrrol-3-yl]acetate Obtained from 6c and 1,4-butanediol, similarly to example 8-II, yield 42%, m.p. 105° C. $^1$H NMR (400 MHz, CDCl$_3$): δ 7.60 (d, 2H), 7.18 (d, 2H), 7.00 (d, 2H), 6.96 (d, 2H), 6.43 (s, 1H), 4.37 (t, 2H), 4.06 (t, 2H), 3.58 (s, 2H), 3.05 (s, 3H), 2.46 (s, 3H), 2.20 (s, 3H), 2.06 (m, 4H), 2.00 (s broad, 1H).

Example 14

4-(Nitrooxy)butyl-2-[1-(4-thiomethylphenyl)-2-methyl-5-(4-methylsulphonylphenyl)-1H-pyrrol-3-yl]acetate Obtained from 6h and 4-nitroxy butanol, similarly to example 8, yield 50%, m.p. 115° C. FT-IR cm$^{-1}$: 1739 (ν C—O), 1279 (ν$_{as}$C—O—C), 1141 (ν$_s$C—O—C), 1619 (ν$_{as}$O—NO$_2$), 840 (ν$_s$O—NO$_2$). $^1$H NMR (400 MHz, CDCl$_3$): δ 7.81 (d, 2H), 7.40 (d, 2H), 7.20 (d, 2H), 6.99 (d, 2H), 6.52 (s, 1H), 4.47 (t, 2H), 4.16 (t, 2H), 3.57 (s, 2H), 3.09 (s, 3H), 2.50 (s, 3H), 2.53 (s, 3H), 2.09 (m, 4H).

Example 14-II 4-(Hydroxy)butyl-2-[1-(4-thiomethylphenyl)-2-methyl-5-(4-methylsulphonylphenyl)-1H-pyrrol-3-yl]acetate Obtained from 6h and 1,4-butanediol, similarly to example 8-II, yield 40%, m.p. 115. $^1$H NMR (400 MHz, CDCl$_3$) δ: 7.82 (d, 2H), 7.40 (d, 2H), 7.18 (d, 2H), 6.90 (d, 2H), 6.42 (s, 1H), 4.37 (t, 2H), 4.06 (t, 2H), 3.47 (s, 2H), 3.05 (s, 3H), 2.44 (s, 3H), 2.20 (s, 3H), 2.09 (m, 4H), 2.08 (s broad, 1H).

Example 15

(R,S)-2,3-bis(Nitrooxy)propyl-2-[1-phenyl-2-methyl-5-(4-methylsulphonylphenyl)-1H-pyrrol-3-yl]acetate 3-Hydroxypropane-1,2-dinitrate (0.8 mmol), DMAP (0.3 mmol), are added to acid 6a (0.3 mmol) in DCM (10 ml) and then EDC (0.5 mmol) in DCM (3 ml) is added dropwise. It is stirred at RT for 2 hours, washed with NaCl s.s. and with H$_2$O, dried and concentrated. The residue is purified by chromatography (silica, hexane/EtOAc 1:1). Oil, yield 54%. $^1$H NMR 200 MHz, (CDCl$_3$) ppm: 2.05 (s, 3H), 2.98 (s, 3H), 3.55 (s, 2H), 4.29-4.34 (m, 1H), 4.48-4.62 (m, 2H), 4.71-4.75 (m, 1H), 5.47-5.49 (m, 1H), 6.47 (s, 1H), 7.12-7.15 (m, 4H), 7.38-7.41 (m, 3H), 7.63 (d, 2H, J=8.3). MS-ESI: m/z 556 (M+Na$^+$). 3-Hydroxypropane-1,2-dinitrate: NaOH (6.5 mmol) is added dropwise, at 0° C., to 2,3-bis(nitroxy)propyl acetate (6.5 mmol) in 20 ml of ethanol, it is stirred at 0° C. for 30 min, it is poured into ice, extracted with ether, dried and concentrated. The oil obtained is used as it is. $^1$H NMR 200 MHz (CD$_3$Cl): 3.90-3.98 (m, 2H), 4.50 (br s, 1H), 4.85-5.04 (m, 2H), 5.52-5.59 (m, 1H). 2,3-bis(Nitroxy)propyl acetate: 4 ml of conc. H$_2$SO$_4$ is added at −78° C. to 2.5 ml of HNO$_3$ (90%), and is allowed to return to 0° C. At −78° C., (2,2-dimethyl-1,3-dioxolan-4-yl)methyl acetate (9.0 mmol) in DCM is added. It is stirred for 1 h at 0° C., and is poured into ice. The organic phase is washed with NaHCO$_3$ s.s., dried and concentrated. The oil obtained is used as it is. $^1$H NMR 200

MHz. CD$_3$Cl): 2.21 (s, 3H), 4.10-4.30 (m, 2H), 4.82-5.01 (m, 2), 5.72 (m, 1H). (2,2-Dimethyl-1,3-dioxolan-4-yl)methyl acetate. $^1$H NMR 200 MHz, CD$_3$Cl): 1.25 (s, 6H), 2.18 (s, 3H), 3.70-3.98 (m, 2H), 4.10-4.30 (m, 2H), 4.54 (m, 1H).

Example 15-II (R,S)-2,3-bis(hydroxy)propyl-2-[1-phenyl-2-methyl-5-(4-methylsulphonylphenyl)-1H-pyrrol-3-yl]-acetate (VA483)

Boric acid (1.5 mmol) is added to a solution of (2,2-dimethyl-1,3-dioxolan-4-yl)methyl-2-(1-phenyl-2-methyl-5-(4-methylsulphonylphenyl)-1H-pyrrol-3-yl)acetate (0.3 mmol) in 6 ml of trimethyl borate, it is stirred for 1 h at 90° C., it is concentrated and the residue is dissolved in CH$_2$Cl$_2$. The organic phase is washed first with NaCl s.s. and then with H$_2$O, dried over anhydrous Na$_2$SO$_4$, filtered and the solvent is concentrated. The raw product is purified by chromatography (silica, EtOAc). Oil, yield 60%, $^1$H NMR 200 MHz (CD3Cl) δ (ppm): 2.04 (s, 3H). 2.58 (br s, 2H), 2.96 (s, 3H), 3.47-3.98 (m, 5H), 4.17-4.21 (m, 2H), 6.49 (s, 1H), 7.10-7.14 (m, 4H), 7.35-7.38 (m, 3H), 7.60 (d, 2H, J=8.3). MS-ESI: m/z 466 (M+Na$^+$).

2,2-Dimethyl-1,3-dioxolan-4-yl)methyl-2-(1-phenyl-2-methyl-5-(4-(methylsulphonyl)phenyl)-1H-pyrrol-3-yl)acetate (2,2-Dimethyl-1,3-dioxolan-4-yl)methanol (0.9 mmol) and DMAP (0.3 mmol) are added to acid 6a (0.3 mmol), in 15 ml of CH$_2$Cl$_2$. Then EDC (0.6 mmol) in 5 ml of CH$_2$Cl$_2$ is added. It is stirred for 1.5 h at RT and then it is washed with NaCl s.s. and then with H$_2$O. The organic phase is dried, filtered and the solvent is concentrated. The raw product is purified by chromatography (silica, hexane/EtOAc 7:3). Oil, yield 78%. $^1$H NMR 200 MHz (CDCl$_3$) δ (ppm): 1.34 (s, 3H), 1.39 (s, 3H), 2.05 (s, 3H), 2.96 (s, 3H), 3.54 (s, 2H), 3.70-3.77 (m, 1H), 4.01-4.36 (m, 4H), 6.51 (s, 1H), 7.11-7.15 (m, 4H), 7.36-7.39 (m, 3H), 7.62 (d, 2H, J=8.3). MS-ESI: m/z 506 (M+Na$^+$).

Example 16

(R,S)-2-(Nitrooxy)ethyl-[2-amino-2-[1-(4-fluorophenyl)-2-methyl-5-(4-methylsulphonyl phenyl)-1H-pyrrol-3-yl]]-acetate Pd/C (0.1.98 g, 11.6 mmol) is added to a solution of N-(benzyloxycarbonyl)-2-nitroxyethyl-[2-amino-2-[1-(4-fluorophenyl)-2-methyl-5-(4-methylsulphonylphenyl)-1H-pyrrol-3-yl]]acetate (1 mmol) in THF (20 ml), prepared from 6m similarly to example 8, and it is hydrogenated for 1.5 h. Then it is filtered on Celite and the solution is concentrated. The residue is purified by chromatography (aluminium oxide, hexane/EtOAc 1:1), yield 65%, m.p. 122° C. FT-IR cm$^{-1}$: 3322 (ν N—H), 1621 (δ N—H), 1740 (ν C—O), 1279 ($v_{as}$C—O—C), 1141 ($v_s$C—O—C), 1594 ($v_{as}$O—NO$_2$), 846 ($v_s$O—NO$_2$). $^1$H NMR (400 MHz, CDCl$_3$) ppm: 7.71 (d, 2H), 7.37 (d, 2H), 7.17 (d, 2H), 7.12 (m, 2H), 6.44 (s, 1H), 5.58 (d, 2H), 5.40 (d, 1H), 4.70 (m, 2H), 4.50 (m, 1H), 4.44 (m, 1H), 3.01 (s, 3H), 2.13 (s, 3H).

Example 16-II (R,S)-2-(Hydroxy)ethyl-[2-amino-2-[1-(4-fluorophenyl)-2-methyl-5-(4-methylsulphonylphenyl)-pyrrol-3-yl]]-acetate Obtained from 6l and ethylene glycol similarly to example 16, m.p. 102° C. $^1$H NMR (400 MHz, CDCl$_3$) ppm: 7.69 (d, 2H), 7.35 (m, 6H) 7.17 (d, 2H), 7.12 (m, 1H), 6.95 (m, 2H), 6.40 (s, 1H), 5.55 (d, 1H), 5.41 (d, 1H), 5.10 (s, 2H), 4.30 (m, 2H), 4.00 (m, 2H), 3.01 (s, 3H), 2.10 (s, 3H).

Example 17

(R,S)-2-(Nitrooxy)ethyl-[2-amino-2-[1-(3-fluorophenyl)-2-methyl-5-(4-methylsulphonyl phenyl)-1H-pyrrol-3-yl]]-acetate Prepared from (R,S)—N-(benzyloxycarbonyl)-2-nitroxyethyl-2-amino-2-[1-(3-fluorophenyl)-2-methyl-5-(4-methylsulphonylphenyl)-1H-pyrrol-3-yl]-acetate similarly to example 16, yield 70%, m.p. 120° C. FT-IR cm$^{-1}$: 3350 (ν N—H), 1626 (δ N—H), 1744 (ν C—O), 1279 ($v_{as}$C—O—C), 1141 ($v_s$C—O—C), 1594 ($v_{as}$O—NO$_2$), 846 ($v_s$O—NO$_2$). $^1$H NMR (400 MHz, CDCl$_3$) ppm: 7.71 (d, 2H), 7.37 (m, 1H), 7.17 (d, 2H), 7.12 (m, 1H), 6.92 (m, 2H), 6.42 (s, 1H), 5.58 (d, 2H), 5.40 (d, 1H), 4.70 (m, 2H), 4.50 (m, 1H), 4.44 (m, 1H), 3.01 (s, 3H), 2.18 (s, 3H).

(R,S)—N-(Benzyloxycarbonyl)-2-(nitroxy)ethyl-2-amino-2-[1-(3-fluorophenyl)-2-methyl-5-(4-methylsulphonylphenyl)-1H-pyrrol-3-yl]-acetate

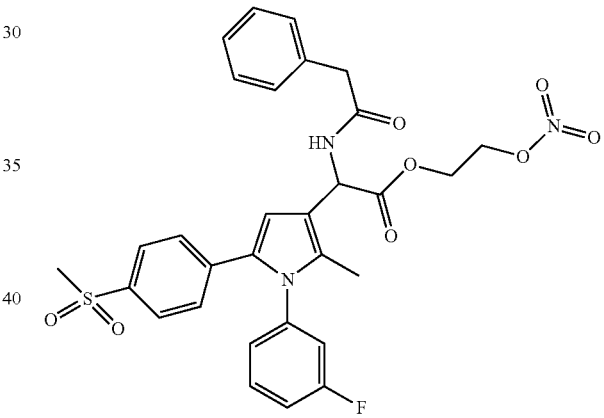

Obtained from 6n and 2-nitroxyethanol similarly to as described in example 8, yield 80%, m.p. 85° C. FT-IR cm$^{-1}$: 1713 (ν C—O), 1279 ($v_{as}$C—O—C), 1141 ($v_s$C—O—C), 1633 (δ N—H), 1594 ($v_{as}$O—NO$_2$), 846 ($v_s$O—NO$_2$). $^1$H NMR (400 MHz, CDCl$_3$) ppm: 7.71 (d, 2H), 7.37 (m, 6H), 7.17 (d, 2H), 7.12 (m, 1H), 6.92 (m, 2H), 6.42 (s, 1H), 5.58 (d, 1H), 5.40 (d, 1H), 5.14 (s, 2H), 4.70 (m, 2H), 4.50 (m, 1H), 4.44 (m, 1H), 3.01 (s, 3H), 2.18 (s, 3H).

Example 17-II (R,S)-2-(Hydroxy)ethyl-[2-amino-2-[1-(3-fluorophenyl)-2-methyl-5-(4-methylsulphonylphenyl)-1H-pyrrol-3-yl]]-acetate Obtained from 6m and ethylene glycol similarly to example 16, m.p. 102° C. $^1$H NMR (400 MHz, CDCl$_3$) ppm: 7.66 (d, 2H), 7.30 (m, 6H), 7.15 (d, 2H), 7.10 (m, 1H), 6.90 (m, 2H), 6.41 (s, 1H), 5.53 (d, 1H), 5.40 (d, 1H), 5.11 (s, 2H), 4.33 (m, 2H), 4.01 (m, 2H), 3.01 (s, 3H), 2.09 (s, 3H).

Example 18

(R,S)-3-(Nitrooxy)propyl-[2-amino-2-[1-(4-fluorophenyl)-2-methyl-5-(4-methylsulphonylphenyl)-1H-pyrrol-3-yl]]-acetate Obtained from 6m and 3-nitroxypropanol similarly to example 16, yield 75%, m.p. 115° C. FT-IR cm$^{-1}$: 3350 ($\nu$ N—H), 1626 ($\delta$ N—H), 1744 ($\nu$ C—O), 1279 ($\nu_{as}$C—O—C), 1141 ($\nu_s$C—O—C), 1594 ($\nu_{as}$O—NO$_2$), 846 ($\nu_s$O—NO$_2$). $^1$H NMR (400 MHz, CDCl$_3$) ppm: 7.70 (d, 2H), 7.29 (d, 2H), 7.18 (d, 2H), 7.08 (m, 2H), 6.41 (s, 1H), 5.56 (d, 2H), 5.39 (d, 1H), 4.71 (m, 2H), 4.39 (m, 1H), 4.35 (m, 1H), 3.01 (s, 3H), 2.18 (s, 3H), 1.90 (m, 2H).

Example 18-II (R,S)-3-(Hydroxy)propyl-[2-amino-2-[1-(4-fluorophenyl)-2-methyl-5-(4-methylsulphonyl phenyl)-1H-pyrrol-3-yl]]-acetate Obtained from 6m and 1,3-propanediol similarly to example 16-II, yield 45%, m.p. 107° C. $^1$H NMR (400 MHz, CDCl$_3$) ppm: 7.70 (d, 2H), 7.29 (d, 2H), 7.18 (d, 2H), 7.08 (m, 2H), 6.36 (s, 1H), 5.56 (d, 2H), 5.32 (d, 1H), 4.31 (m, 1H), 4.23 (m, 1H), 3.89 (m, 2H), 3.01 (s, 3H), 2.44 (s broad, 1H), 2.18 (s, 3H), 1.80 (m, 2H).

Example 19

(R,S)-3-(Nitrooxy)propyl-[2-amino-2-[1-(3-fluorophenyl)-2-methyl-5-(4-methylsulphonyl phenyl)-1H-pyrrol-3-yl]]-acetate Obtained from 6n and 3-nitroxyethanol similarly to example 16, yield 70%, m.p. 117° C. FT-IR cm$^{-1}$: 3340 ($\nu$ N—H), 1623 ($\delta$ N—H), 1740 ($\nu$ C—O), 1259 ($\nu_{as}$C—O—C), 1140 ($\nu_s$C—O—C), 1594 ($\nu_{as}$O—NO$_2$), 855 ($\nu_s$O—NO$_2$). $^1$H NMR (400 MHz, CDCl$_3$) ppm: 7.70 (d, 2H), 7.39 (m, 1H), 7.18 (d, 2H), 7.09 (m, 1H), 6.93 (m, 2H), 6.41 (s, 1H), 5.56 (d, 2H), 5.37 (d, 1H), 4.66 (m, 2H), 4.42 (m, 1H), 4.39 (m, 1H), 3.01 (s, 3H), 2.18 (s, 3H), 1.93 (m, 2H).

Example 19-II (R,S)-3-(Hydroxy)propyl-[2-amino-2-[1-(3-fluorophenyl)-2-methyl-5-(4-methylsulphonyl phenyl)-1H-pyrrol-3-yl]]-acetate Obtained from 6n and 1,3-propanediol similarly to example 16, yield 40%, m.p. 110° C. $^1$H NMR (400 MHz, CDCl$_3$) ppm: 7.71 (d, 2H), 7.41 (m, 1H), 7.15 (d, 2H), 7.05 (m, 1H), 6.97 (m, 2H), 6.40 (s, 1H), 5.59 (d, 2H), 5.36 (d, 1H), 4.41 (m, 2H), 4.02 (m, 1H), 3.93 (m, 1H), 3.01 (s, 3H), 2.50 (s broad, 1H), 2.18 (s, 3H), 1.89 (m, 2H).

Example 20

(R,S)-4-(Nitrooxy)butyl-[2-amino-2-[1-(4-fluorophenyl)-2-methyl-5-(4-methylsulphonyl phenyl)-1H-pyrrol-3-yl]]-acetate Obtained from 6m and 4-nitroxybutanol similarly to example 16, yield 66%, m.p. 108° C. FT-IR cm$^{-1}$: 3310 ($\nu$ N—H), 1633 ($\delta$ N—H), 1722 ($\nu$ C—O), 1280 ($\nu_{as}$C—O—C), 1160 ($\nu_s$C—O—C), 1601 ($\nu_{as}$O—NO$_2$), 861 ($\nu_s$O—NO$_2$). $^1$H NMR (400 MHz, CDCl$_3$) ppm: 7.71 (d, 2H), 7.25 (d, 1H), 7.15 (d, 2H), 7.07 (d, 2H), 6.41 (s, 1H), 5.56 (d, 2H), 5.37 (d, 1H), 4.65 (m, 2H), 4.40 (m, 1H), 4.32 (m, 1H), 3.01 (s, 3H), 2.18 (s, 3H), 1.90 (m, 4H).

Example 20-II (R,S)-4-(Hydroxy)butyl-[2-amino-2-[1-(4-fluorophenyl)-2-methyl-5-(4-methylsulphonyl phenyl)-1H-pyrrol-3-yl]]-acetate Obtained from 6m and 1,4-butanediol similarly to example 16, yield 40%, m.p. 101° C. $^1$H NMR (400 MHz, CDCl$_3$) ppm: 7.70 (d, 2H), 7.37 (d, 2H), 7.15 (d, 2H), 7.09 (d, 2H), 6.45 (s, 1H), 5.80 (d, 2H), 5.35 (d, 1H), 4.25 (m, 2H), 3.78 (m, 2H), 3.00 (s, 3H), 2.60 (s broad, 1H), 2.05 (s, 3H), 1.68 (m, 4H).

Example 21

(R,S)-4-(Nitrooxy)butyl-[2-amino-2-[1-(3-fluorophenyl)-2-methyl-5-(4-methylsulphonyl phenyl)-1H-pyrrol-3-yl]]-acetate Obtained from 6n and 4-nitroxybutanol similarly to example 16, yield 57%, m.p. 110° C. FT-IR cm$^{-1}$: 3350 ($\nu$ N—H), 1626 ($\delta$ N—H), 1744 ($\nu$ C—O), 1279 ($\nu_{as}$C—O—C), 1141 ($\nu_s$C—O—C), 1594 ($\nu_{as}$O—NO$_2$), 846 ($\nu_s$O—NO$_2$). $^1$H NMR (400 MHz, CDCl$_3$) ppm: 7.71 (d, 2H), 7.23 (m, 1H), 7.10 (d, 2H), 7.07 (m, 1H), 6.91 (m, 2H), 6.40 (s, 1H), 5.56 (d, 2H), 5.37 (d, 1H), 4.65 (m, 2H), 4.40 (m, 1H), 4.32 (m, 1H), 3.01 (s, 3H), 2.18 (s, 3H), 1.90 (m, 4H).

Example 21-II (R,S)-4-(Hydroxy)butyl-[2-amino-2-[1-(3-fluorophenyl)-2-methyl-5-(4-methylsulphonyl phenyl)-1H-pyrrol-3-yl]]-acetate Obtained from 6n and 1,4-butanediol similarly to example 16, yield 40%, m.p. 98° C. $^1$H NMR (400 MHz, CDCl$_3$) ppm: 7.70 (d, 2H), 7.43 (m, 1H), 7.15 (d, 2H), 7.05 (m, 1H), 6.97 (m, 2H), 6.40 (s, 1H), 5.59 (d, 2H), 5.35 (d, 1H), 4.43 (m, 2H), 4.00 (m, 1H), 3.93 (m, 1H), 3.01 (s, 3H), 2.50 (s broad, 1H), 2.18 (s, 3H), 1.87 (m, 4H).

Example 22

N-[(2-Nitroxy)ethyl]-2-[1-phenyl-2-methyl-5-(4-methylsulphonylphenyl)-1H-pyrrol-3-yl]acetamide The following are added to acid 6a (0.54 mmol) in DCM (10 ml), at 0° C.: DIPEA (2.17 mmol), EDC (1.08 mmol), HOBt (0.17 mmol) and 2-nitroxyethylamine nitrate (0.54 mmol). It is stirred for 1 h at 0° C., and for 2 h at RT. It is quenched in H$_2$O, extracted with DCM, dried and concentrated. The residue is purified by chromatography (silica, EtOAc), yield 87%. $^1$H NMR (CDCl$_3$) ppm: 1.97 (s, 3H); 2.91 (s, 3H); 3.40 (s, 2H); 3.51-3.55 (m, 2H); 4.48-4.51 (m, 2H); 6.39 (s, 1H); 6.43-6.46 (s broad, 1H); 7.06-7.09 (m, 4H); 7.33-7.34 (m, 3H); 7.55-7.57 (m, 2H). 2-nitroxyethylamine nitrate: HNO$_3$ (100%, 3 ml) is added at 0° C. to 20 ml of DCM, the solution is stirred for 10 min, then 2-ethanolamine (16 mmol) is added. After 50 minutes, acetic anhydride (2.0 ml) is added dropwise. The solution obtained is stirred for 40 min at RT. The precipitate obtained is filtered, m.p. 89° C., yield 90%. FT-IR cm$^{-1}$: 1636 ($v_{as}$O—NO$_2$), 880 ($v_s$O—NO$_2$). $^1$H NMR (400 MHz, MeOH-d$_4$) ppm: 4.80 (t, 2H), 3.40 (t, 2H).

Example 22-II

N-[(2-Hydroxy)ethyl]-2-[1-phenyl-2-methyl-5-(4-methylsulphonylphenyl)-1H-pyrrol-3-yl]acetamide Prepared from acid 6a and 2-aminoethanol similarly to example 22, yield 98%. $^1$H NMR (CDCl$_3$) ppm: 2.05 (s, 3H); 2.65-2.70 (s broad, 1H); 2.98 (s, 3H); 3.39-3.47 (m, 2H); 6.23 (s broad, 1H); 6.45 (s, 1H); 7.12-7.16 (m, 4H); 7.37-7.42 (m, 2H); 7.61-7.69 (m, 2H). MS ESI: m/z 413 (M+H$^+$).

Example 23

N-[(2-Nitroxy)ethyl]-2-[1-(4-fluorophenyl)-2-methyl-5-(4-methylsulphonylphenyl)-1H-pyrrol-3-yl]acetamide Prepared from 6g similarly to example 22, yield 90%, m.p. 135° C. FT-IR cm$^{-1}$: 3300 (v N—H), 1640 (v C—O), 1520 cm$^{-1}$ (δ N—H), 1278 (v C—N), 1595 ($v_{as}$O—NO$_2$), 865 ($v_s$O—NO$_2$). $^1$H NMR (400 MHz, CDCl$_3$) ppm: 7.70 (d, 2H), 7.23 (m, 6H), 6.43 (s, 1H), 6.12 (s broad, 1H), 4.59 (t, 2H), 3.63 (t, 2H), 3.49 (s, 2H), 3.02 (s, 3H), 2.09 (s, 3H).

Example 23-II

N-[(2-Hydroxy)ethyl]-2-[1-(4-fluorophenyl)-2-methyl-5-(4-methylsulphonylphenyl)-1H-pyrrol-3-yl]acetamide Obtained from 6g similarly to example 22-II, yield 80%, m.p. 99° C. $^1$H NMR (400 MHz, CDCl$_3$) ppm: 7.67 (d, 2H), 7.16 (d, 2H), 6.99 (m, 4H), 6.46 (s, 1H), 6.40 (s broad, 1H), 3.70 (t, 2H), 3.48 (s, 2H), 3.40 (m, 2H), 3.00 (s, 3H), 2.70 (s broad, 1H), 2.04 (s, 3H).

Example 24

N-[(2-Nitroxy)ethyl]-2-[1-(3-fluorophenyl)-2-methyl-5-(4-methylsulphonylphenyl)-1H-pyrrol-3-yl]acetamide Obtained from 6d similarly to example 22, yield 90%, m.p. 133° C. FT-IR cm$^{-1}$: 3300 (v N—H), 1640 (v C—O), 1520 (δ N—H), 1278 (v C—N), 1595 ($v_{as}$O—NO$_2$), 865 ($v_s$O—NO$_2$). $^1$H NMR (400 MHz, CDCl$_3$) ppm: 7.71 (d, 2H), 7.18 (m, 6H), 6.40 (s, 1H), 6.12 (s broad, 1H), 4.59 (t, 2H), 3.63 (t, 2H), 3.49 (s, 2H), 3.02 (s, 3H), 2.04 (s, 3H).

Example 24-II

N-[(2-Amino-2-[1-(3-fluorophenyl)-2-methyl-5-(4-methylsulphonylphenyl)-1H-pyrrol-3-yl]acetamide Obtained from 6d similarly to example 22-II, yield 85%, m.p. 97° C. $^1$H NMR (400 MHz, CDCl$_3$) ppm: 7.70 (d, 2H), 7.40 (m, 1H), 7.19 (d, 2H), 7.13 (m, 1H), 6.96 (m, 1H), 6.87 (m, 1H), 6.47 (s, 1H), 6.40 (s broad, 1H), 3.70 (t, 2H), 3.48 (s, 2H), 3.40 (m, 2H), 3.00 (s, 3H), 2.70 (s broad, 1H), 2.04 (s, 3H).

Example 25

N-[(3-Nitroxy)propyl]-2-[1-phenyl-2-methyl-5-(4-methylsulphonylphenyl)-1H-pyrrol-3-yl]acetamide Prepared from 6a and 3-(nitroxypropyl)amine nitrate, similarly to example 22, oil. $^1$H NMR (CDCl$_3$): 1.82-1.90 (m, 2H); 2.01 (s, 3H); 2.95 (s, 3H); 3.35 (d, 2H); 3.40 (s, 2H); 4.45 (t, 2H, J=5.7); 6.25 (s broad, 1H); 6.40 (s, 1H); 7.05-7.18 (m, 4H); 7.30-7.45 (m, 3H); 7.50-7.62 (m, 2H).

3-(Nitrooxypropyl)amine Nitrate

Obtained similarly to as described in example 22, yield 80%, m.p. 90° C. FT-IR cm$^{-1}$: 1636 ($v_{as}$O—NO$_2$), 880 ($v_s$O—NO$_2$). $^1$H NMR (400 MHz, MeOH-d$_4$) ppm: 4.80 (t, 2H), 3.60 (t, 2H), 2.10 (m, 2H).

Example 25-II

N-[(3-Hydroxy)propyl]-2-[1-phenyl-2-methyl-5-(4-methylsulphonylphenyl)-1H-pyrrol-3-yl]acetamide Prepared from 6a and propanolamine similarly to example 22-II, yield 64%. $^1$H NMR (CDCl$_3$) ppm: 1.61-1.72 (m, 2H); 2.04 (s, 3H); 2.37 (s broad, 1H); 2.99 (s, 3H); 3.43-3.46 (m, 2H); 3.54 (s, 2H); 3.63 (t, 2H, J=5.5); 6.31 (s, 1H); 7.11-7.17 (m, 4H); 7.37-7.43 (m, 3H); 7.63-7.67 (m, 2H).

Example 26

N-[(3-Nitroxy)propyl]-2-[1-(4-fluorophenyl)-2-methyl-5-(4-methylsulphonylphenyl)-1H-pyrrol-3-yl]acetamide Obtained from 6g similarly to example 22, yield 80%, m.p. 127° C. FT-IR cm$^{-1}$: 3300 (v N—H), 1640 (v C—O), 1520 (δ N—H), 1278 (v C—N), 1595 ($v_{as}$O—NO$_2$), 865 ($v_s$O—NO$_2$). $^1$H NMR (400 MHz, CDCl$_3$) ppm: 7.70 (d, 2H), 7.23 (m, 6H), 6.43 (s, 1H), 6.12 (s broad, 1H), 4.59 (t, 2H), 3.63 (t, 2H), 3.49 (s, 2H), 3.02 (s, 3H), 2.09 (s, 3H), 1.89 (m, 2H).

Example 26-II

N-[(3-Hydroxy)propyl]-2-[1-(4-fluorophenyl)-2-methyl-5-(4-methylsulphonylphenyl)-1H-pyrrol-3-yl]acetamide Obtained from 6g and propanolamine similarly to example 22-II, yield 70%, m.p. 105° C. $^1$H NMR (400 MHz, CDCl$_3$) ppm: 7.60 (d, 2H), 7.20 (m, 6H), 6.41 (s, 1H), 5.90 (s broad, 1H), 3.98 (t, 2H), 3.63 (t, 2H), 3.49 (s, 2H), 3.04 (s, 3H), 2.09 (s, 3H), 1.86 (m, 2H).

Example 27

N-[(3-Nitroxy)propyl]-2-[1-(3-fluorophenyl)-2-methyl-5-(4-methylsulphonylphenyl)-1H-pyrrol-3-yl]acetamide Obtained from 6d similarly to example 22, yield 76%, m.p. 125° C. FT-IR cm$^{-1}$: 3300 (v N—H), 1640 (v C—O), 1520 (δ N—H), 1278 (v C—N), 1595 ($v_{as}$O—NO$_2$), 865 ($v_s$O—

NO$_2$). $^1$H NMR (400 MHz, CDCl$_3$) ppm: 7.72 (d, 2H), 7.30 (m, 4H), 7.24 (m, 2H), 6.40 (s, 1H), 6.03 (s broad, 1H), 4.49 (t, 2H), 3.62 (t, 2H), 3.40 (s, 2H), 3.11 (s, 3H), 2.07 (s, 3H), 1.88 (m, 2H).

Example 27-II

N-[(3-Hydroxy)propyl]-2-[1-(3-fluorophenyl)-2-methyl-5-(4-methylsulphonylphenyl)-1H-pyrrol-3-yl]acetamide Obtained from 6d and propanolamine similarly to example 22-II, yield 72%, m.p. 102° C. $^1$H NMR (400 MHz, CDCl$_3$) ppm: 7.66 (d, 2H), 7.29 (m, 4H), 7.21 (m, 2H), 6.39 (s, 1H), 6.11 (s broad, 1H), 3.92 (t, 2H), 3.59 (t, 2H), 3.52 (s, 2H), 3.09 (s, 3H), 2.10 (s, 3H), 1.90 (m, 2H).

Example 28

(S)-3-(Nitroxy)-2-[[1-phenyl-2-methyl-5-(4-methylsulphonylphenyl)-1H-pyrrol-3-yl]acetamido]propanoic Acid TEA (2.88 mmol) and BOP (0.769 mmol) are added to acid 6a (0.56 mmol) in THF (10 ml), then it is stirred at RT for 1 h. (S)-2-Amino-3-nitroxypropionic acid (1.189 mmol) is added and it is stirred at RT for 2-3 h. It is filtered and concentrated, the residue is taken up in 10% K$_2$CO$_3$ and the resultant precipitate is separated by filtration. The filtrate, concentrated at reduced pressure, is treated with a solution of 10% K$_2$CO$_3$, it is extracted with DCM, washed with 2N HCl, dried and concentrated, yield 90%. $^1$H NMR (CDCl$_3$): 2.00 (s, 3H); 2.96 (s, 3H); 3.51 (s, 2H); 4.87-4.95 (m, 3H); 6.44 (s, 1H); 6.82-6.85 (broad s, 1H); 7.11-7.15 (m, 4H); 7.36-7.45 (m, 3H); 7.59-7.63 (m, 2H); 10.35-10.45 (broad s, 1H). MS ESI: m/z 501.8 (M+H$^+$).

(S)-2-Amino-3-nitroxypropionic Acid

HNO$_3$ conc. (3 mL) is added, at 0° C., to DCM (20 ml), it is stirred for 10 min, S-serine (16 mmol) is added and it is stirred at 0° C. for 50 min, then acetic anhydride (2 ml) is added dropwise and the reaction mixture is left to return to RT and is stirred at that temperature for 40 min. The product is precipitated by adding ethyl ether, filtered, washed with ether and dried. Oil, $^1$H NMR (CD$_3$SO): 4.77-4.99 (m, 3H); 8.31 (broad s).

Example 28-II (S)-3-(Hydroxy)-2-[[1-phenyl-2-methyl-5-(4-methylsulphonylphenyl)-1H-pyrrol-3-yl]acetamido]propanoic Acid The following are added, at 0° C., to acid 6a (0.8 mmol) in DCM (10 ml): DIPEA (2.43 mmol), EDC (1.63 mmol), HOBt (0.27 mmol) and L-serine ethyl ester dihydrochloride (0.8 mmol). It is stirred at RT for 12 hours, then it is washed with H$_2$O, the organic phase is separated, dried and concentrated. The residue is purified by chromatography (silica, EtOAc/MeOH (9:1)) obtaining: N-[1-(carboxyethyl)-2-hydroxyethyl]-2-[1-phenyl-2-methyl-5-(4-methanesulphonylphenyl)-1H-pyrrol-3-yl]-acetamide. Oil, yield 77%. $^1$H NMR (CDCl$_3$) ppm: 1.25 (t, 3H); 2.05 (s, 3H); 2.70 (broad t, 1H); 2.97 (s, 3H); 3.51 (s, 2H); 3.93 (m, 2H); 4.20 (m, 2H); 4.63 (m, 1H); 6.48 (s, 1H); 6.74 (broad d, 1H); 7.11-7.16 (m, 4H); 7.37-7.40 (m, 3H); 7.60-7.64 (m, 3H). The carboxyethyl derivative (0.55 mmol) is treated with NaOH (0.55 mmol) in EtOH (5 ml), at 0° C., for 1 hour. It is acidified with 3N HCl to pH 6; the solvent is evaporated and the residue is taken up in EtOAc. The organic phase is washed until neutral with NaCl s.s., dried and concentrated. The residue is treated with EtOAc/n-hexane to give the product, m.p. 80-83° C., yield 50%. $^1$H NMR (DMSO-d$_6$) ppm: 1.97 (s, 3H); 3.11 (s, 3H); 3.34 (s, 2H); 3.55-3.75 (m, 2H); 4.23-4.31 (m, 1H); 4.95-5.04 (s broad, 1H); 6.54 (s, 1H); 7.10-7.22 (m, 4H); 7.40-7.49 (m, 2H); 7.59-7.66 (m, 2H); 8.06-8.10 (broad d, 1H); 12.59 (broad s, 1H). MS ESI: m/z 455 (M−H$^+$); m/z 495 (M+K$^+$).

Example 29

(S)-3-(Nitroxy)-2-[[1-(4-fluorophenyl)-2-methyl-5-(4-methylsulphonylphenyl)-1H-pyrrol-3-yl]acetamido]propanoic Acid TEA (0.5 ml) and BOP (0.84 mmol) are added to a solution of acid 6g (0.7 mmol) in THF. After 1 h, the nitrate of (S)-2-amino-3-nitroxypropionic acid (1.5 mmol) is added and it is stirred for a further 2 h at RT. Then it is concentrated and the residue is dissolved in 10% K$_2$CO$_3$, then it is filtered. The solution thus obtained is acidified to pH 2 with 2N HCl and the precipitate obtained is filtered and dried; yield 80%, m.p. 109° C. FT-IR cm$^{-1}$: 3300 (ν N—H), 1734 (ν C═O), 1640 (ν C—O), 1520 (δ N—H), 1278 (ν C—N), 1595 (ν$_{as}$O—NO$_2$), 865 (ν$_s$O—NO$_2$). $^1$H NMR (400 MHz, CDCl$_3$): δ 7.70 (d, 2H), 7.30 (m, 4H), 7.23 (m, 2H), 6.73 (s broad, 1H), 6.50 (s, 1H), 4.70 (m, 1H), 4.20 (m, 2H), 3.54 (s, 2H), 3.01 (s, 3H), 2.07 (s, 3H).

Example 29-II (S)-3-(Hydroxy)-2-[[1-(4-fluorophenyl)-2-methyl-5-(4-methylsulphonylphenyl)-1H-pyrrol-3-yl]acetamido]propanoic Acid Obtained from 6g and (S)-2-amino-3-hydroxypropionic acid similarly to example 28-II, yield 90%, m.p. 120° C. $^1$H NMR (400 MHz, CDCl$_3$) δ: 7.70 (d, 2H), 7.31 (m, 4H), 7.22 (m, 2H), 6.73 (s broad, 1H), 6.50 (s, 1H), 4.70 (m, 1H), 4.20 (m, 2H), 3.54 (s, 2H), 3.01 (s, 3H), 2.07 (s, 3H).

Example 30

(S)-3-(Nitroxy)-2-[1-(3-fluorophenyl)-2-methyl-5-(4-methylsulphonylphenyl)-1H-pyrrol-3-yl]acetamido]propanoic Acid Obtained from 6d and (S)-2-amino-3-nitroxypropionic acid similarly to example 28, yield 80%, m.p. 110° C. FT-IR cm$^{-1}$: 3310 (ν N—H), 1734 (ν C═O), 1640 (ν C—O), 1520 (δ N—H), 1278 (ν C—N), 1595 (ν$_{as}$O—NO$_2$), 865 (ν$_s$O—NO$_2$). $^1$H NMR (400 MHz, CDCl$_3$) δ: 7.70 (d, 2H), 7.20 (m, 6H), 6.73 (s broad, 1H), 6.50 (s, 1H), 4.60 (m, 1H), 4.12 (m, 2H), 3.51 (s, 2H), 3.10 (s, 3H), 2.09 (s, 3H).

Example 30-II (S)-3-(Hydroxy)-2-[1-(3-fluorophenyl)-2-methyl-5-(4-methylsulphonylphenyl)-1H-pyrrol-3-yl]acetamido]propanoic Acid Obtained from 6d and 2-amino-3-hydroxypropionic acid similarly to example 28, yield 89%, m.p. 115° C., $^1$H NMR (400 MHz, CDCl$_3$): δ 7.70 (d, 2H), 7.20 (m, 6H), 6.73 (s broad, 1H), 6.52 (s, 1H), 4.71 (m, 1H), 4.20 (m, 2H), 3.50 (s, 2H), 3.01 (s, 3H), 2.05 (s, 3H).

Example 31

(R,S)-4-(Nitroxy)-2-[[1-phenyl-2-methyl-5-(4-methylsulphonylphenyl)-1H-pyrrol-3-yl]acetamido]butanoic Acid Prepared similarly to example 28 from 6a and (R,S)-2-amino-4-nitroxybutanoic acid nitrate. $^1$H NMR (CDCl$_3$): 2.03 (s, 3H), 2.10-3.30 (m, 2H); 2.97 (s, 3H); 3.44 (s, 2H); 4.58-4.60 (t, 2H); 4.55-4.62 (m, 1H); 6.45 (s, 1H); 6.89-6.92 (b d, 1H); 7.05-7.10 (m, 4H); 7.30-7.40 (m, 3H); 7.52-7.58 (m, 2H). MS ESI: m/z 515.9 (M+H$^+$). 2-Amino-4-nitroxybutanoic acid, nitrate salt. Obtained from (R,S)-homoserine similarly to example 28, yield 88%, m.p. 104° C. FT-IR cm$^{-1}$: 3165 (ν N—H), 1730 (ν C═O), 1625 (ν$_{as}$O—NO$_2$), 880 (ν$_s$O—NO$_2$). $^1$H NMR (400 MHz, MeOH-d$_4$): δ 4.73 (m, 2H), 4.14 (m, 1H), 2.37 (m, 2H).

Example 31-II (R,S)-4-(Hydroxy)-2-[[1-phenyl-2-methyl-5-(4-methylsulphonylphenyl)-1H-pyrrol-3-yl]acetamido]butanoic Acid The following are added to acid 6a (0.54 mmol), in DCM (10 ml) at 0° C.: DIPEA (1.62 mmol), EDC (1.08 mmol), HOBt (0.18 mmol) and L-homoserine (0.54 mmol). The reaction mixture is stirred at RT for 12 hours; it is taken up in H$_2$O and the organic phase is separated, dried and concentrated. The residue obtained is crystallized from EtOAc. The lactone intermediate 2-[1-phenyl-2-methyl-5-(4-methylsulphonylphenyl)-1H-pyrrol-3-yl]-N-(2-oxo-tetrahydrofuran-3-yl)-acetamide is obtained, yield 63%. $^1$H NMR (CDCl$_3$): 2.06-2.17 (m, 3H+1H); 2.76-2.89 (m, 1H); 2.98 (s, 3H); 3.52 (s, 2H); 4.17-4.63 (m, 3H); 6.27-6.32 (broad d, 1H); 6.45 (s, 1H); 7.12-7.16 (m, 4H); 7.40-7.41 (m, 3H); 7.62-7.66 (m, 2H). MS ESI: m/z 453.1 (M+H$^+$). The lactone derivative (0.345 mmol) is treated with NaOH (0.0345 mmol) in EtOH (5 ml) at 0° C. for 1 hour. The solution is acidified with 3N HCl to pH 6; the solvent is concentrated and the residue is taken up in EtOAc. The organic phase is washed until neutral, dried and concentrated. The product crystallizes from diethyl ether, yield 50%. $^1$H NMR (DMSO-d$_6$): 1.69-1.87 (m, 2H); 1.97 (s, 3H); 3.12 (s, 3H); 3.30 (s, 2H); 3.33-3.42 (m, 2H); 4.21-4.32 (m, 1H); 6.52 (s, 1H); 7.10-7.19 (m, 4H); 7.43-7.46 (m, 3H); 7.60-7.64 (m, 2H); 8.15-8.20 (b d, 1H); 12.45 (bs, 1H). MS ESI: m/z 469.1 (M−H$^+$).

Example 32

(R,S)-4-(Nitroxy)-2-[[1-(4-fluorophenyl)-2-methyl-5-(4-methylsulphonylphenyl)-1H-pyrrol-3-yl]acetamido]butanoic Acid Obtained from 6g and 2-amino-4-nitroxybutanoic acid similarly to example 29, at yield of 89%, m.p. 116° C. FT-IR cm$^{-1}$: 3300 (ν N—H), 1734 (ν C═O), 1640 (ν C═O), 1520 (δ N—H), 1278 (ν C—N), 1595 (ν$_{as}$O—NO$_2$), 865 (ν$_s$O—NO$_2$). $^1$H NMR (400 MHz, CDCl$_3$): δ 7.70 (d, 2H), 7.30 (m, 6H), 6.63 (s, 1H), 6.50 (s broad, 1H), 4.69 (m, 1H), 4.40 (m, 2H), 3.46 (s, 2H), 3.07 (s, 3H), 2.40 (m, 1H), 2.35 (m, 1H), 2.09 (s, 3H).

Example 32-II (R,S)-4-(Hydroxy)-2-[[1-(4-fluorophenyl)-2-methyl-5-(4-methylsulphonylphenyl)-1H-pyrrol-3-yl]acetamido]butanoic Acid Obtained from 6g and 2-amino-4-hydroxybutanoic acid similarly to example 31, yield 82%, m.p. 125° C. $^1$H NMR (400 MHz, CDCl$_3$): δ 7.72 (d, 2H), 7.35 (m, 6H), 6.59 (s, 1H), 6.57 (s broad, 1H), 4.59 (m, 1H), 3.70 (m, 2H), 3.46 (s, 2H), 3.07 (s, 3H), 2.10 (m, 2H), 2.09 (s, 3H).

Example 33

(R,S)-4-(Nitroxy)-2-[[1-(3-fluorophenyl)-2-methyl-5-(4-methylsulphonylphenyl)-1H-pyrrol-3-yl]acetamido]butanoic Acid Obtained from 6d and 2-amino-4-nitroxybutanoic acid similarly to example 31, yield 89%, m.p. 112° C. FT-IR cm$^{-1}$: 3300 (ν N—H), 1734 (ν C═O), 1640 (ν C═O), 1520 (δ N—H), 1278 (ν C—N), 1595 (ν$_{as}$O—NO$_2$), 865 (ν$_s$O—NO$_2$). $^1$H NMR (400 MHz, CDCl$_3$) δ: 7.70 (d, 2H), 7.32 (m, 6H), 6.60 (s, 1H), 6.53 (s broad, 1H), 4.62 (m, 1H), 4.33 (m, 2H), 3.50 (s, 2H), 3.09 (s, 3H), 2.43 (m, 1H), 2.41 (m, 1H), 2.09 (s, 3H).

Example 33-II (R,S)-4-(Hydroxy)-2-[[1-(3-fluorophenyl)-2-methyl-5-(4-methylsulphonylphenyl)-1H-pyrrol-3-yl]acetamido]butanoic Acid Obtained from 6d and 2-amino-4-hydroxybutanoic acid similarly to example 31, yield 79%, m.p. 130° C., $^1$H NMR (400 MHz, CDCl$_3$) δ: 7.69 (d, 2H), 7.31 (m, 6H), 6.57 (s, 1H), 6.44 (s broad, 1H), 4.43 (m, 1H), 3.67 (m, 2H), 3.40 (s, 2H), 3.05 (s, 3H), 2.07 (m, 2H), 2.01 (s, 3H).

Example 34

(R,S)-2-Amino-N-(2-nitroxy)ethyl-2-[1-phenyl-2-methyl-5-(2-4-methylsulphonylphenyl)-1H-pyrrol-3-yl]acetamide Prepared similarly from 2-nitroxyethylamine.

Example 34-II (R,S)-2-Amino-N-(2-hydroxy)ethyl-2-[1-phenyl-2-methyl-5-(2-4-methylsulphonylphenyl)-1H-pyrrol-3-yl]acetamide Prepared similarly from 2-aminoethanol.

Example 35

(R,S)-2-Amino-N-(2-nitroxy)propyl-2-[1-phenyl-2-methyl-5-(2-4-methylsulphonylphenyl)-1H-pyrrol-3-yl]acetamide Prepared similarly from 3-nitroxypropylamine.

Example 35-II (R,S)-2-Amino-N-(2-hydroxy)propyl-2-[1-phenyl-2-methyl-5-(2-4-methylsulphonylphenyl)-1H-pyrrol-3-yl]acetamide

Example 36

2-[2-[1-Phenyl-2-methyl-5-(4-methylsulphonylphenyl)-1H-pyrrol-3-yl]ethoxy]ethyl Nitrate Tetrabutylammonium nitrate (0.9 mmol) is added to the mesylate (0.3 mmol) stated below, in toluene (5 ml), and the solution is heated under reflux for 1 h. Then H$_2$O and ether are added, the phases are separated and the organic phase is washed with NaCl s.s. and with H$_2$O, dried and concentrated. The residue is purified by chromatography (silica, hexane/EtOAc), yield 70%, m.p. 78-80° C., $^1$H NMR 200 MHz (CDCl$_3$) ppm: 2.03 (s, 3H), 2.75 (t, 2H, J=7.2), 2.95 (s, 3H), 3.64-3.77 (m, 4H), 4.61 (t, 2H, J=4.4), 6.43 (s, 1H), 7.09-7.15 (m, 4H), 7.36-7.40 (m, 3H), 7.61 (d, 2H, J=8.4). MS-ESI: m/z 467 (M+Na$^+$).

2-[2-[1-Phenyl-2-methyl-5-(4-methylsulphonylphenyl)-1H-pyrrol-3-yl]ethoxy]ethyl Methanesulphonate DMAP (0.03 mmol) and DIPEA (0.5 mmol) are added to the alcohol of example 36-II (0.3 mmol) in DCM (10 ml). MsCl (0.6 mmol) is added at 0° C., and it is stirred for 3 h at RT. Then H$_2$O (5 ml) is added, and it is stirred for 1 h, the phases are separated and the organic phase is washed with NaHCO$_3$ s.s. and with H$_2$O, then dried and concentrated. The residue is purified by chromatography (silica, hexane/EtOAc). Oil, yield 81%. $^1$H NMR 200 MHz (CDCl$_3$) δ: 2.03 (s, 3H), 2.75 (t, 2H, J=7.2), 2.95 (s, 3H), 2.97 (s, 3H), 3.65-3.77 (m, 4H), 4.34-4.39 (m, 2H), 6.43 (s, 1H), 7.09-7.14 (m, 4H), 7.35-7.39 (m, 3H), 7.60 (d, 2H, J=8.3). MS-ESI: m/z 500 (M+Na$^+$).

Example 36-II

2-[2-[1-Phenyl-2-methyl-5-(4-methylsulphonylphenyl)-1H-pyrrol-3-yl]ethoxy]ethanol p-Toluenesulphonic acid (0.1 mmol) is added at RT to 1-phenyl-2-methyl-5-(4-methylsulphonylphenyl)-3-[2-(2-(tetrahydro-2H-pyran-2-yloxy)ethoxy]ethyl-1H-pyrrole (0.7 mmol) in MeOH (6 ml). The reaction mixture is stirred for 1 h at 55° C. Then 30 ml of H$_2$O is added and it is extracted with ether. The organic phase is washed with NaCl s.s., with H$_2$O, dried and concentrated. The residue is purified by chromatography (silica, hexane/EtOAc, 3:7). Oil, yield 83%. $^1$H NMR 200 MHz (CDCl$_3$) δ: 2.03 (s, 3H), 2.23 (br s, 1H), 2.77 (t, 2H, J=7.3), 2.95 (s, 3H), 3.57-3.72 (m, 6H), 6.43 (s, 1H), 7.09-7.15 (m, 4H), 7.34-7.40 (m, 3H), 7.60 (d, 2H, J=8.3). MS-ESI: m/z 422 (M+Na$^+$).

1-Phenyl-2-methyl-5-(4-methylsulphonylphenyl)-3-[2-(2-(tetrahydro-2H-pyran-2-yloxy)ethoxy]ethyl-1H-pyrrole

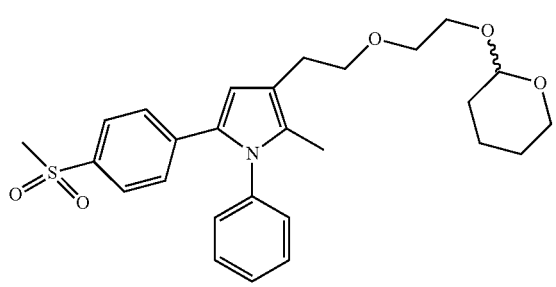 [SMILES: Cc1c(CCOCCOC2CCCCO2)cc(-c2ccc(S(C)(=O)=O)cc2)n1-c1ccccc1]

Tetrabutylammonium bromide (0.2 mmol) and 2-(bromoethoxy)tetrahydro-2H-pyran (1.4 mmol) are added, at 0° C., to 1-phenyl-2-methyl-5-(4-methylsulphonylphenyl)-3-(2-ethoxyethyl)-1H-pyrrole (0.7 mmol) in 5 ml of aqueous NaOH (50%). The suspension is stirred at 70° C. for 60 h. Then NaCl s.s. (16 ml) is added and it is extracted with ether. The organic phase is washed with NaCl s.s. and with H$_2$O, then dried and concentrated. The residue is purified by chromatography (silica, hexane/EtOAc 1:1). Oil, yield 79%. $^1$H NMR 200 MHz (CDCl$_3$) δ (ppm): 1.47-1.81 (m, 7H), 2.01 (s, 3H), 2.74 (t, 2H, J=7.2), 2.92 (s, 3H), 3.39-3.49 (m, 1H), 3.53-3.70 (m, 4H), 3.78-3.88 (m, 2H), 4.60 (m, 1H), 6.43 (s, 1H), 7.07-7.11 (m, 4H), 7.32-7.37 (m, 3H), 7.58 (d, 2H, J=8.3). MS-ESI: m/z 506 (M+Na$^+$).

1-Phenyl-3-(2-hydroxyethyl)-2-methyl-5-(4-methylsulphonylphenyl)-1H-pyrrole

Prepared as described in WO2008014821.

Example 37

2-[2-[2-(1-(4-Fluorophenyl)-2-methyl-5-(4-methylsulphonylphenyl)-1H-pyrrol-3-yl]ethoxy]ethyl Nitrate Prepared similarly to example 36, oil, yield 70%. $^1$H NMR (CDCl$_3$) ppm: 2.03 (s, 3H); 2.75 (t, 2H); 2.98 (s, 3H); 3.63-3.78 (m, 4H); 4.62 (t, 2H); 6.43 (s, 1H); 7.03-7.16 (m, 6H); 7.63-7.67 (m, 2H).

2-[2-[2-(1-(4-Fluorophenyl)-2-methyl-5-(4-methylsulphonylphenyl)-1H-pyrrol-3-yl]ethoxy]ethyl Methanesulphonate Prepared similarly to example 36, oil, yield 98%. $^1$H NMR (CDCl$_3$) ppm: 2.03 (s, 3H); 2.75 (t, 2H); 2.99 (s, 3H); 3.65-3.77 (m, 4H); 4.37 (t, 2H); 6.42 (s, 1H); 7.08-7.15 (m, 6H); 7.62-7.67 (m, 2H).

Example 37-II

2-[2-[2-(1-(4-Fluorophenyl)-2-methyl-5-(4-methylsulphonylphenyl)-1H-pyrrol-3-yl]ethoxy]ethanol Prepared similarly to example 36-II, yield 56%, m.p. 110-114° C. $^1$H NMR (CDCl$_3$) ppm: 2.01 (broad s, 1H); 2.03 (s, 3H); 2.76 (t, 2H); 2.98 (s, 3H); 3.57-3.71 (m, 6H); 6.42 (s, 1H); 7.02-7.14 (m, 6H); 7.61-7.66 (m, 2H).

4-Fluorophenyl-2-methyl-5-(4-methylsulphonylphenyl)-3-(2-(2-(tetrahydro-2H-pyran-2-yloxy)ethoxy)ethyl)-1H-pyrrole Oil, $^1$H NMR (CDCl$_3$) ppm: 1.51-1.79 (m, 6H); 2.03 (s, 3H); 2.77 (t, 2H); 2.99 (s, 3H); 3.45-3.92 (m, 8H); 4.64 (t, 1H); 6.44 (s, 1H), 7.07-7.15 (m, 6H); 7.62-7.67 (m, 2H).

Example 38

2-[2-[2-(1-(3-Fluorophenyl)-2-methyl-5-(4-methylsulphonylphenyl)-1H-pyrrol-3-yl]ethoxy]ethyl Nitrate Prepared similarly to example 36, m.p. 94-97° C., yield 70%. $^1$H NMR (CDCl$_3$): 2.07 (s, 3H); 2.77 (t, 2H); 3.01 (s, 3H); 3.67-3.79 (m, 4H); 4.64 (t, 2H); 6.44 (s, 1H); 6.88-6.96 (m, 2H); 7.10-7.18 (m, 3H); 7.36-7.38 (m, 1H); 7.66-7.69 (m, 2H).

2-[2-[2-(1-(3-Fluorophenyl)-2-methyl-5-(4-methylsulphonylphenyl)-1H-pyrrol-3-yl]ethoxy]ethyl Methanesulphonate Oil, $^1$H NMR (CDCl$_3$): 2.07 (s, 3H); 2.76 (t, 2H); 2.98 (s, 6H); 3.66-3.76 (m, 4H); 4.37 (t, 2H); 6.42 (s, 1H); 6.83-6.95 (m, 2H); 7.02-7.20 (m, 3H); 7.29-7.40 (m, 1H); 7.61-7.66 (m, 2H).

Example 38-II

2-[2-[2-(1-(3-Fluorophenyl)-2-methyl-5-(4-methylsulphonylphenyl)-1H-pyrrol-3-yl]ethoxy]ethanol Prepared similarly to example 36-II. Oil. $^1$H NMR (CDCl$_3$): 2.06 (s, 3H); 2.17 (broad s); 2.76 (t, 2H); 2.98 (s, 3H); 3.57-3.77 (m, 6H); 6.42 (s, 1H); 6.83-6.93 (m, 2H); 7.02-7.16 (m, 3H); 7.29-7.40 (m, 1H); 7.61-7.66 (m, 2H).

3-Fluorophenyl-2-methyl-5-(4-methylsulphonylphenyl)-3-(2-(2-(tetrahydro-2H-pyran-2-yloxy)ethoxy)ethyl)-1H-pyrrole Oil $^1$H NMR (CDCl$_3$): 1.41-1.96 (m, 6H); 2.04 (s, 3H); 2.74 (t, 2H); 2.96 (s, 3H); 3.41-3.90 (m, 8H); 4.61 (t, 1H); 6.43 (s, 1H), 6.81-7.39 (m, 6H); 7.60-7.64 (m, 2H).

Example 39

2-[2-[2-(1-(3,4-Difluorophenyl)-2-methyl-5-(4-methylsulphonylphenyl)-1H-pyrrol-3-yl]ethoxy]ethyl Nitrate Prepared similarly to example 36, m.p. 93-96° C. $^1$H NMR (CDCl$_3$): 2.04 (s, 3H); 2.74 (t, 2H); 2.97 (s, 3H); 3.63-3.78 (m, 4H); 4.62 (t, 2H); 6.42 (s, 1H); 6.88-7.09 (m, 2H); 7.13-7.21 (m, 3H); 7.63-7.71 (m, 2H).

2-[2-[2-(1-(3,4-Difluorophenyl)-2-methyl-5-(4-methylsulphonylphenyl)-1H-pyrrol-3-yl]ethoxy]ethyl Methanesulphonate Oil, $^1$H NMR (CDCl$_3$): 2.05 (s, 3H); 2.77 (t, 2H); 2.99 (s, 6H); 3.65-3.76 (m, 4H); 4.38 (t, 2H); 6.42 (s, 1H); 6.87-7.03 (m, 1H); 7.11-7.20 (m, 4H); 7.65-7.70 (m, 2H).

Example 39-II

2-[2-[2-(1-(3,4-Difluorophenyl)-2-methyl-5-(4-methylsulphonylphenyl)-1H-pyrrol-3-yl]ethoxy]ethanol Prepared similarly to example 36-II, m.p. 138-140° C. $^1$H NMR (CDCl$_3$): 2.02 (s, 3H); 2.37 (broad s); 2.73 (t, 2H); 2.6 (s, 3H); 3.54-3.72 (m, 6H); 6.39 (s, 1H); 6.85-6.98 (m, 2H); 7.01-7.18 (m, 3H); 7.59-7.66 (m, 2H).

3,4-Difluorophenyl-2-methyl-5-(4-(methylsulphonyl)phenyl)-3-(2-(2-(tetrahydro-2H-pyran-2-yloxy)ethoxy)ethyl)-1H-pyrrole Oil $^1$H NMR (CDCl$_3$): 1.48-1.81 (m, 4H); 1.98 (s, 3H); 2.69 (t, 2H); 2.93 (s, 3H), 3.36-3.4 (m, 10H); 4.56 (t, 1H); 6.38 (s, 1H), 6.81-6.99 (m, 2H); 7.06-7.20 (m, 3H); 7.59-7.63 (m, 2H).

Example 40

3-[2-[2-(1-Phenyl-2-methyl-5-(4-methylsulphonylphenyl)-1H-pyrrol-3-yl)ethoxy]propyl Nitrate Prepared similarly to example 36, yield 65%, m.p. 131-133° C., $^1$H NMR 200 MHz (CDCl$_3$) δ: 1.94-2.05 (m, 5H), 2.75 (t, 2H, J=7.2), 2.97 (s, 3H), 3.55-3.67 (m, 4H), 4.57 (t, 2H, J=6.4), 6.43 (s, 1H), 7.11-7.15 (m, 4H), 7.37-7.39 (m, 3H), 7.62 (d, 2H, J=8.6). MS-ESI: m/z 481 (M+Na$^+$).

3-(2-(1-Phenyl-2-methyl-5-(4-methylsulphonylphenyl)-1H-pyrrol-3-yl)ethoxy)propyl Methanesulphonate Oil, yield 80%. $^1$H NMR 200 MHz (CDCl$_3$) δ (ppm): 1.96-2.08 (m, 5H), 2.75 (t, 2H, J=7.2), 2.94 (s, 3H), 2.98 (s, 3H), 3.56-3.67 (m, 4H), 4.34 (t, 2H, J=6.2), 6.43 (s, 1H), 7.11-7.16 (m, 4H), 7.36-7.40 (m, 3H), 7.62 (d, 2H, J=8.3). MS-ESI: m/z 514 (M+Na$^+$).

Example 40-II

1-Phenyl-2-methyl-5-(4-methylsulphonylphenyl)-3-(2-propyloxyl)ethyl-1H-pyrrole Prepared similarly to example 36-II, oil, yield 84%. $^1$H NMR 200 MHz (CDCl$_3$) δ: 1.47-1.89 (m, 8H), 2.01 (s, 3H), 2.72 (t, 2H, J=7.1), 2.93 (s, 3H), 3.40-3.48 (m, 2H), 3.52-3.62 (m, 4H), 3.74-3.85 (m, 2H), 4.53 (m, 1H), 6.41 (s, 1H), 7.07-7.11 (m, 4H), 7.32-7.37 (m, 3H), 7.58 (d, 2H, J=8.4). MS-ESI: m/z 520 (M+Na$^+$).

Example 41

3-[2-[2-(1-(4-Fluorophenyl)-2-methyl-5-(4-methylsulphonylphenyl)-1H-pyrrol-3-yl)]ethoxy]propyl Nitrate Prepared similarly to example 36, yield 84%, m.p. 114-116° C. $^1$H NMR (CDCl$_3$): 2.01-2.04 (m, 2H), 2.06 (s, 3H); 2.77 (t, 2H), 3.02 (s, 3H); 3.56-3.66 (m, 4H), 4.59 (t, 2H); 6.44 (s, 1H); 7.09-7.17 (m, 6H); 7.67-7.69 (m, 2H).

3-(2-(4-Fluorophenyl-2-methyl-5-(4-(methylsulphonyl)phenyl)-1H-pyrrol-3-yl)ethoxy)propyl Methanesulphonate Oil, $^1$H NMR (CDCl$_3$): 1.95-2.02 (m, 2H); 2.03 (s, 3H); 2.75 (t, 2H); 2.95 (s, 3H); 2.99 (s, 3H); 3.55-3.65 (m, 4H); 4.34 (t, 2H); 6.41 (s, 1H); 7.08-7.20 (m, 6H); 7.63-7.68 (m, 2H).

Example 41-II

3-[2-[2-(1-(4-Fluorophenyl)-2-methyl-5-(4-methylsulphonylphenyl)-1H-pyrrol-3-yl)]ethoxy]propanol Prepared similarly to example 36-II, yield 40%, m.p. 100-102° C. $^1$H NMR (CDCl$_3$) ppm: 1.78-1.89 (m, 2H), 2.03 (s, 3H), 2.75 (t, 2H, J=6.9), 3.60-3.79 (m, 6H), 6.42 (s, 1H), 7.07-7.16 (m, 6H), 7.65 (m, 2H). MS-ESI: m/z 466 (M+Cl$^-$).

Example 42

3-[2-(1-(3-Fluorophenyl)-2-methyl-5-(4-methylsulphonylphenyl)-1H-pyrrol-3-yl)ethoxy]propyl Nitrate Prepared similarly to example 36, m.p. 111-113° C. $^1$H NMR (CDCl$_3$): 1.94-2.03 (m, 2H); 2.06 (s, 3H); 2.74 (t, 2H);

3.00 (s, 3H); 3.54-3.65 (m, 4H); 4.56 (t, 2H); 6.42 (s, 1H); 6.86-6.95 (m, 2H); 7.04-7.17 (m, 3H); 7.31-7.42 (m, 1H); 7.64-7.68 (m, 2H).

Example 42-II

3-[2-(1-(3-Fluorophenyl)-2-methyl-5-(4-methylsulphonylphenyl)-1H-pyrrol-3-yl)ethoxy]propanol Prepared similarly to example 36-II, Oil, $^1$H NMR (CDCl$_3$): 1.76-1.88 (m, 2H), 2.04 (s, 3H), 2.47 (broad s, 1H), 2.71 (t, 2H), 2.98 (s, 3H); 3.51-3.82 (m, 6H), 6.41 (s, 1H), 6.83-6.93 (m, 2H); 7.02-7.16 (m, 3H); 7.29-7.40 (m, 1H); 7.61-7.66 (m, 2H).

Example 43

(R,S)-2-[3-(Nitroxy)propyl]-1-[1-phenyl-2-methyl-5-(4-methylsulphonylphenyl)-1H-pyrrol-3-yl]ethanamine Prepared similarly to example 36 starting from the corresponding N—BOC amino ester.

Example 43-II (R,S)-2-[3-(nitroxy)propyl]-1-[1-phenyl-2-methyl-5-(4-methylsulphonylphenyl)-1H-pyrrol-3-yl]ethanamine Prepared similarly to example 36-II starting from the corresponding N—BOC amino ester.

Example 44

(R,S)-2-[2-(Nitroxy)ethyl]-1-[1-(4-fluorophenyl)-2-methyl-5-(4-methylsulphonylphenyl)-1H-pyrrol-3-yl]ethanamine The NH-Boc derivative (0.24 mmol), AlCl$_3$ (0.24 mmol), neutral Al$_2$O$_3$ (186.5 mg) are put in a closed tube, and irradiated with microwaves (50 PW, 100° C.) for 3 minutes. The reaction mixture is taken up in EtOAc and filtered on silica, eluting with EtOAc. The organic phase is washed with NaHCO$_3$ and with NaCl, then dried and concentrated. The residue is purified by chromatography (silica, EtOAc), oil, yield 20%. $^1$H NMR (CDCl$_3$) ppm: 1.98 (s, 3H); 2.95 (s, 3H); 2.95 (s, 3H); 3.70-3.79 (m, 4H); 4.39-4.46 (m, 1H); 4.60-4.63 (m, 2H); 6.83 (s, 1H), 7.09-7.13 (m, 6H); 7.59-7.63 (m, 2H).

(R,S)-2-[2-(Nitroxy)ethyl]-1-[[1-(4-fluorophenyl)-2-methyl-5-(4-methylsulphonylphenyl)-1H-pyrrol-3-yl]-N-tert-butoxycarbonyl]ethanamine The methanesulphonate (0.23 mmol) stated below, dissolved in toluene (5 mL), is treated with tetrabutylammonium nitrate (0.960 mmol) under reflux for 1.5 h, then H$_2$O and EtOAc are added. The phases are separated, the organic phase is washed with H$_2$O, dried and concentrated. It is purified by chromatography (silica, CH$_2$Cl$_2$/EtOAc), oil, yield 77.5%. $^1$H NMR (CDCl$_3$): 1.41 (s, 9H); 2.06 (s, 3H); 2.96 (s, 3H); 3.70-3.81 (m, 4H), 4.61 (t, 2H); 4.87-5.02 (m, 2H); 6.48 (s, 1H); 7.01-7.14 (m, 6H), 7.61-7.66 (m, 2H).

(R,S)-2-(tert-Butoxycarbonylamino)-2-[[1-(4-fluorophenyl)-2-methyl-5-(4-methylsulphonylphenyl)-1H-pyrrol-3-yl]ethoxy]ethyl Methanesulphonate DIPEA (0.526 mmol) and DMAP (0.037 mmol) are added to the alcohol stated below (0.375 mmol) in CH$_2$Cl$_2$ (10 mL), then MsCl (0.754 mmol) is added at 0° C. and it is stirred for 1 h at RT. Then NaHCO$_3$ s.s. is added, it is extracted with CH$_2$Cl$_2$ and the organic phase is washed with H$_2$O, dried and concentrated. $^1$H NMR (CDCl$_3$) ppm: 1.43 (s, 9H), 2.09 (s, 3H); 2.97 (s, 3H); 2.99 (s, 3H); 3.73-3.80 (m, 4H); 4.37 (t, 2H); 4.90-4.97 (m, 2H); 6.45 (s, 1H); 7.08-7.15 (m, 6H); 7.64-7.79 (m, 2H).

(R,S)-2-[2-(Hydroxy)ethyl]-1-[[1-(4-fluorophenyl)-2-methyl-5-(4-methylsulphonylphenyl)-1H-pyrrol-3-yl]-N-tert-butoxycarbonyl]ethanamine

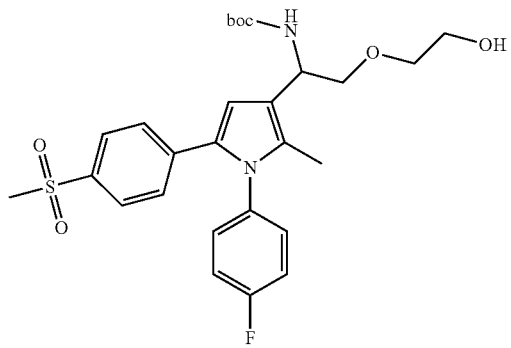

A solution of the tetrahydropyranyl ether described below (2.1 g, 0.0034 mol) and pyridinium p-toluenesulphonate (1.02 g, 0.004 mol) in methanol (50 ml) is stirred at 45° C. for 19 h. The solvent is concentrated and the residue is extracted with EtOAc, washed with H$_2$O, dried and concentrated. The product is purified by chromatography (silica, hexane-EtOAc, 1:4), 1.35 g, 75%. $^1$H NMR 400 MHz, DMSO-d6: δ 1.38 (s, 9H), 2.02 (s, 3H), 3.15 (s, 3H), 3.45-3.49 (m, 4H), 3.59-3.92 (m, 1H), 4.58 (br s, 1H), 5.01 (br s, 1H), 7.16 (d, J=12.00 Hz, 2H), 7.29-7.31 (m, 4H), 7.69 (d, J=8.00 Hz, 2H). $^{13}$C NMR 100 MHz, DMSO-d6: 11.13, 28.76, 40.82, 43.88, 47.08, 60.72, 72.55, 73.87, 78.12, 111.03, 116.85, 121.60, 127.30, 130.70, 130.83, 130.95, 130.99, 135.15, 137.85, 155.59, 160.09, 163.34. MS: 555.2 (M+Na).

(R,S)—N-tert-Butoxycarbonyl-1-amino-2-[1-(4-fluorophenyl)-2-methyl-5-(4-methylsulphonylphenyl)-1H-pyrrol-3-yl]-3-[2-(2-(tetrahydro-2H-pyran-2-yloxy)ethoxy]ethyl-1H-pyrrole

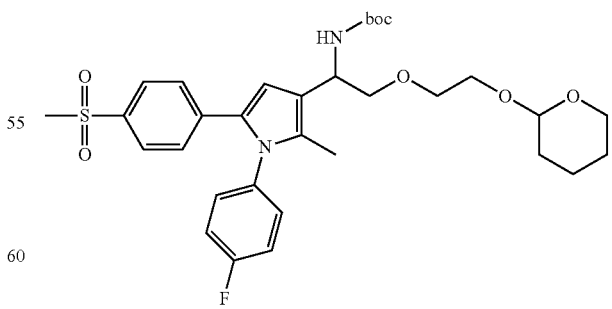

(R,S)—N-tert-Butoxycarbonyl-1-amino-2-[1-(4-fluorophenyl)-2-methyl-5-(4-methylsulphonylphenyl)-1H-pyrrolo-3-yl]ethanol (6 g, 0.0123 mol) and 3-bromoethanol-tetrahydropyranyl ether (16.43 g, 0.0736 mol) are heated at 65°

C. for 7 hours, in a 50% aqueous NaOH solution (19.8 ml, 0.2456 mol) containing tetrabutylammonium hydrogen sulphate (600 mg). Then it is extracted with DCM, the extracts are washed with NaCl s.s., with H₂O, then dried and concentrated. The residue is purified by chromatography (silica, hexane-EtOAc 1:5), 4.5 g, yield 64%. MS: 639.2 (M+Na).

(R,S)—N-tert-Butoxycarbonyl-1-amino-2-[1-(4-fluorophenyl)-2-methyl-5-(4-methylsulphonylphenyl)-1H-pyrrolo-3-yl]ethanol

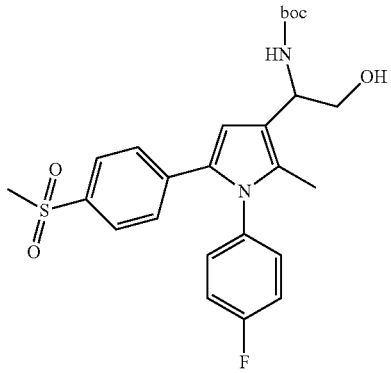

A solution of the ester (10 g, 26 mmol), described below, in THF (75 ml) is added dropwise at 0° C. to a suspension of lithium aluminium hydride (2.1 g, 55.6 mmol), then it is stirred at 0° C. for 1 h. It is neutralized by adding 10% NaOH, it is filtered on Celite and concentrated. The residue is taken up in EtOAc and washed with 1N HCl, H₂O and NaCl s.s, then dried and concentrated. The residue is purified by chromatography (silica, hexane-EtOAc 1:1) to give the product, 5.4 g, yield 59%. ¹H NMR 400 MHz, CDCl₃: δ 1.47 (s, 9H), 2.12 (s, 3H), 2.70-0.00 (m, 1H), 3.01 (s, 3H), 3.83-3.92 (m, 2H), 4.83 (d, J=8.00 Hz, 1H), 5.01 (br s, 1H), 6.47 (s, 1H), 7.11-7.13 (m, 2H), 7.15 (d, J=8.00 Hz, 2H), 7.69 (d, J=8.00 Hz, 2H).

¹³C NMR 100 MHz, CDCl₃: 11.08, 28.39, 44.44, 50.14, 79.96, 109.18, 116.5, 119.62, 127.43, 130.03, 131.10, 131.78, 134.46, 137.16, 137.99, 156.36, 160.77, 163.25. MS: 511.5 (M+Na).

Ethyl-(R,S)—N-tert-Butoxycarbonyl-2-amino-2-[1-(4-fluorophenyl)-2-methyl-5-(4-methylsulphonylphenyl)-1H-pyrrolo-3-yl]acetate

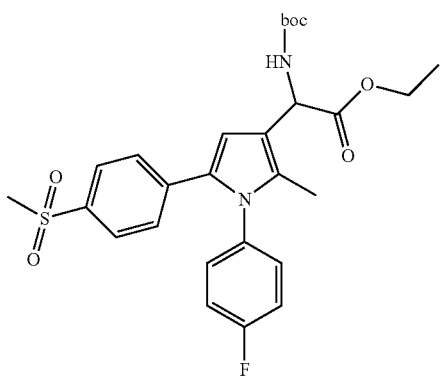

(R,S)-2-Amino-2-[1-(4-fluorophenyl)-2-methyl-5-(4-methylsulphonylphenyl)-1H-pyrrolo-3-yl]acetic Acid (10 g, 0.02326 mol) in methanol (15 ml) is treated with Boc-anhydride (10.1 g, 0.04651 mol), the reaction mixture is stirred at RT for 18 h. Then it is diluted with H₂O and it is extracted with EtOAc. It is washed with H₂O, dried and concentrated. The residue is purified by chromatography (silica, hexane EtOAc 1:20) Yield: 7 g, 57%. ¹H NMR 400 MHz, DMSO-d₆: δ 1.18 (t, J=8.00 Hz, 3H), 1.39 (s, 9H), 2.02 (s, 3H), 3.16 (s, 3H), 4.09-4.14 (m, 2H), 5.12 (d, J=8.00 Hz, 1H), 6.65 (s, 1H), 7.18 (d, J=8.00 Hz, 2H), 7.33-7.35 (m, 4H), 7.52 (d, J=8.00 Hz, 1H), 7.71 (d, J=8.00 Hz, 2H). MS: 553.2 (M+Na).

Example 45

(R,S)-2-[3-(Nitroxy)propyl]-1-[1-(4-fluorophenyl)-2-methyl-5-(4-methylsulphonylphenyl)-1H-pyrrol-3-yl]ethanamine Prepared similarly to example 44, oil, ¹H NMR (CDCl₃) ppm: 1.95-2.02 (m, 2H); 2.04 (s, 3H); 2.97 (s, 3H); 3.60-3.72 (m, 4H), 4.19-4.29 (m, 1H), 4.52-4.60 (m, 2H), 6.56 (s, 1H); 7.07-7.15 (m, 6H); 7.07-7.15 (m, 6H); 7.62-7.67 (m, 2H).

(R,S)-2-[3-(Nitroxy)propyl]-1-[[1-(4-fluorophenyl)-2-methyl-5-(4-methylsulphonylphenyl)-1H-pyrrol-3-yl]-N-tert-butoxycarbonyl]ethanamine Oil, ¹H NMR (CDCl₃) ppm: 1.43 (s, 9H); 1.95-2.05 (m, 2H); 2.08 (s, 3H); 2.98 (s, 3H); 3.55-3.69 (m, 4H); 4.53 (t, 2H); 4.82-4.98 (m, 2H); 6.44 (s, 1H); 7.07-7.14 (m, 6H); 7.63-7.68 (m, 2H).

(R,S)-2-(tert-Butoxycarbonylamino)-2-[[1-(4-fluorophenyl)-2-methyl-5-(4-methylsulphonylphenyl)-1H-pyrrol-3-yl]ethoxyl]propyl Methanesulphonate Oil, yield 78.4%. ¹H NMR (CDCl₃) ppm: 1.42 (s, 9H); 1.76-2.11 (m, 5H); 2.93 (s, 3H); 2.97 (s, 3H); 3.55-3.67 (m, 4H); 4.31 (t, 2H); 4.86-5.04 (m, 2H); 6.45 (s, 1H); 7.06-7.14 (m, 6H); 7.62-7.66 (m, 2H).

Example 45-II (R,S)-2-[3-(Nitroxy)propyl]-1-[1-(4-fluorophenyl)-2-methyl-5-(4-methylsulphonylphenyl)-1H-pyrrol-3-yl]ethanamine Prepared similarly to example 44-II. Oil. ¹H NMR (CDCl₃): 1.80 (t, 2H); 1.93 (s, 3H); 2.97 (s, 3H); 3.64-3.79 (m, 6H); 4.03-4.29 (m, 1H); 6.62 (s, 1H); 7.00-7.37 (m, 6H); 7.62-7.75 (m, 2H).

(R,S)—N-tert-Butoxycarbonyl-1-amino-2-[1-(4-fluorophenyl)-2-methyl-5-(4-methylsulphonylphenyl)-3-[2-(2-(tetrahydro-2H-pyran-2-yloxy)propyloxyl]ethyl-1H-pyrrole Prepared similarly to example 44-II starting from 3-bromopropanol-tetrahydropyranyl ether, yield: 64%, MS: 653.2 (M+Na).

Example 46

2-(Nitrooxy)-[2-[(1-(4-fluorophenyl)-2-methyl-5-(4-methylsulphonylphenyl)-1H-pyrrol-3-yl]ethoxy] acetate 1-Phenyl-3-(2-hydroxyethyl)-2-methyl-5-(4-methylsulphonylphenyl)-1H-pyrrole (0.4 mmol), DMAP (0.4 mmol) and EDC (0.8 mmol) in DCM (5 ml) are added to a solution of 2-(nitrooxy)acetic acid (0.8 mmol) in DCM (20 ml). The reaction mixture is stirred for 3 hours at RT, then washed with NaCl s.s. The organic phase is dried and concentrated. The residue is purified by chromatography (silica, hexane/ethyl acetate 1:1), yield 85%. m.p. 127-129° C. $^1$H NMR 200 MHz (CDCl$_3$) δ 2.01-2.12 (m, 5H), 2.46 (t, 2H, J=7.0), 2.82 (t, 2H, J=7.0), 2.97 (s, 3H), 4.28 (t, 2H, J=6.9), 4.49 (t, 2H, J=6.0), 6.41 (s, 1H), 7.11-7.15 (m, 4H), 7.36-7.38 (m, 3H), 7.62 (d, 2H, J=8.2). MS-ESI: m/z 509 (M+Na$^+$).

Example 47

3-(Nitrooxy)-[2-[(1-(4-fluorophenyl)-2-methyl-5-(4-methylsulphonylphenyl)-1H-pyrrol-3-yl]ethoxy] butanoate Prepared from 4-(nitrooxy)butanoic acid similarly to example 46, yield 85%, m.p. 127-129° C. $^1$H NMR 200 MHz (CDCl$_3$) δ: 2.01-2.12 (m, 5H), 2.46 (t, 2H, J=7.0), 2.82 (t, 2H, J=7.0), 2.97 (s, 3H), 4.28 (t, 2H, J=6.9), 4.49 (t, 2H, J=6.0), 6.41 (s, 1H), 7.11-7.15 (m, 4H), 7.36-7.38 (m, 3H), 7.62 (d, 2H, J=8.2). MS-ESI: m/z 509 (M+Na$^+$).

Example 48

2-(Nitroxy)-N-[2-(1-phenyl-2-methyl-5-(4-methylsulphonylphenyl)-1H-pyrrol-3-yl)-ethyl]acetamide Obtained from 2-[1-phenyl-2-methyl-5-(4-methylsulphonylphenyl)-1H-pyrrol-3-yl]-ethanamine by treatment with nitroxyacetic acid similarly to example 8.

Example 48-II

2-(Hydroxy)-N-[2-(1-phenyl-2-methyl-5-(4-methylsulphonylphenyl)-1H-pyrrol-3-yl)-ethyl]acetamide A solution of 2-(acetoxy)-N-[2-(1-phenyl-2-methyl-5-(4-methylsulphonylphenyl)-1H-pyrrol-3-yl)-ethyl]acetamide (0.95 g, 0.210 mmol) in methanol (10 mL) is treated with K$_2$CO$_3$ (0.58 g, 0.421 mmol) in water (10 mL). The reaction mixture is heated at 50° C. for 2 h, then it is concentrated and the residue is extracted with CH$_2$Cl$_2$. It is dried and concentrated, obtaining the product at yield of 98%. $^1$H NMR 400 MHz, CDCl$_3$: δ 2.05 (s, 3H), 2.41 (s, 1H), 2.74 (t, J=4.00 Hz, 2H), 3.00 (s, 3H), 3.56-3.58 (m, 2H), 4.13 (s, 2H), 6.44 (s, 1H), 6.56 (s, 1H), 7.14-7.16 (m, 4H), 7.39-7.44 (m, 3H), 7.65 (d, J=8.00 Hz, 2H).

2-(Acetoxy)-N-[2-(1-phenyl-2-methyl-5-(4-methylsulphonylphenyl)-1H-pyrrol-3-yl)-ethyl]acetamide TEA (0.29 g, 0.296 mmol) and acetoxyacetyl chloride (0.323 g, 0.00237 mol) are added, at 0° C., to a solution of 2-[1-phenyl-2-methyl-5-(4-methylsulphonylphenyl)-1H-pyrrol-3-yl]-ethanamine (W2008014821), (0.7 g, 0.00197 mol), in CH$_2$Cl$_2$ (10 mL). It is stirred at RT for 2 h. Then it is poured into water and extracted with CH$_2$Cl$_2$, washed with NaHCO$_3$ s.s., and then with H$_2$O, dried and concentrated. The solid obtained (0.85 g, 95.5%) is used as it is for the next step.

Example 49

2-(Nitroxy)-N-methyl-N-[2-(1-phenyl-2-methyl-5-(4-methylsulphonylphenyl)-1H-pyrrol-3-yl)-ethyl] acetamide Obtained similarly starting from N-methyl-2-[1-phenyl-2-methyl-5-(4-methylsulphonylphenyl)-1H-pyrrol-3-yl]-ethanamine.

Example 49-II

2-(Hydroxy)-N-methyl-N-[2-(1-phenyl-2-methyl-5-(4-methylsulphonylphenyl)-1H-pyrrol-3-yl)-ethyl] acetamide Obtained similarly starting from N-methyl-2-[1-phenyl-2-methyl-5-(4-methylsulphonylphenyl)-1H-pyrrol-3-yl]-ethanamine.

Example 50

3-(Nitroxy)-N-[2-(1-phenyl-2-methyl-5-(4-methylsulphonylphenyl)-1H-pyrrol-3-yl)-ethyl]propionamide Obtained similarly to example 48.

Example 50-II

3-(Hydroxy)-N-[2-(1-phenyl-2-methyl-5-(4-methylsulphonylphenyl)-1H-pyrrol-3-yl)-ethyl]propionamide Obtained similarly to example 48-II.

Example 51

3-(Nitroxy)-N-methyl-N-[2-(1-phenyl-2-methyl-5-(4-methylsulphonylphenyl)-1H-pyrrol-3-yl)-ethyl] propionamide Obtained similarly starting from N-methyl-2-[1-phenyl-2-methyl-5-(4-methylsulphonylphenyl)-1H-pyrrol-3-yl]-ethanamine.

Example 51-II

3-(Hydroxy)-N-methyl-N-[2-(1-phenyl-2-methyl-5-(4-methylsulphonylphenyl)-1H-pyrrol-3-yl)-ethyl] propionamide Obtained similarly to example 48-II starting from N-methyl-2-[1-phenyl-2-methyl-5-(4-methylsulphonylphenyl)-1H-pyrrol-3-yl]-ethanamine.

Example 52

(R,S)-2-Amino-3-(nitroxy)-N-[2-(1-phenyl)-2-methyl-5-(4-methylsulphonylphenyl)-1H-pyrrol-3-yl)-ethyl]propionamide Obtained similarly to example 52-II starting from (R,S)—N-(benzyloxycarbonyl)-2-amino-3-(nitroxy)-N-[2-(1-phenyl)-2-methyl-5-(4-methylsulphonylphenyl)-1H-pyrrol-3-yl)-ethyl]propionamide.

Example 52-II (R,S)-2-Amino-3-(hydroxy)-N-[2-(1-phenyl)-2-methyl-5-(4-methylsulphonylphenyl)-1H-pyrrol-3-yl)-ethyl]propionamide Pd/C (95 mg, 10%) is added to a solution of (R,S)—N-(benzyloxycarbonyl)-2-amino-3-(hydroxy)-N-[2-(1-phenyl)-2-methyl-5-(4-methylsulphonylphenyl)-1H-pyrrol-3-yl)-ethyl]propionamide (0.9 g, 0.15 mmol) in THF (15 mL), then it is hydrogenated at 1 atm for 1.5 h, it is filtered and concentrated. The raw product is purified by chromatography (silica, 0-5% MeOH in $CHCl_3$), yield 50%. $^1H$ NMR 400 MHz, DMSO-$d_6$: δ 2.00 (s, 3H), 2.42 (t, J=8.00 Hz, 2H), 3.14 (s, 3H), 3.28-3.31 (m, 2H), 3.86-3.87 (m, 1H), 4.40 (t, J=2.80 Hz, 2H), 6.54 (s, 1H), 7.17 (d, J=8.00 Hz, 2H), 7.21-7.23 (m, 2H), 7.44-7.49 (m, 3H), 7.64 (d, J=8.00 Hz, 2H).

(R,S)—N-(Benzyloxycarbonyl)-2-amino-3-(hydroxy)-N-[2-(1-phenyl)-2-methyl-5-(4-methylsulphonylphenyl)-1H-pyrrol-3-yl)-ethyl]propionamide TEA (0.605 g, 0.59 mmol), HOBt (0.06 g, 0.03 mmol) and EDC (0.9 g, 0.47 mmol), at 4-5° C., are added to a solution of N-benzyloxycarbonyl-serine (0.95 g, 0.39 mmol) in DCM (15 mL) at 0° C.; after stirring for 5 min, 2-[(1-phenyl)-2-methyl-5-(4-methylsulphonylphenyl)-1H-pyrrol-3-yl]-ethanamine (1.4 g, 0.39 mmol) in DCM (3 mL) is added, then it is stirred at RT for 3 h. The reaction mixture is washed with 1.5 N HCl, $NaHCO_3$ s.s. and with $H_2O$, then dried and concentrated. The residue is purified by chromatography (silica, 0-15% EtOAc in hexane), yield 1.3 g, 57%. $^1H$ NMR 400 MHz, DMSO-d6: δ 1.98 (s, 3H), 2.55-2.58 (m, 2H), 3.13 (s, 3H), 3.26 (t, J=6.00 Hz, 2H), 3.53-3.59 (m, 2H), 4.02 (d, J=7.08 Hz, 1H), 4.85 (t, J=5.60 Hz, 1H), 4.95-5.06 (m, 2H), 6.54 (s, 1H), 7.16-7.23 (m, 5H), 7.30-7.36 (m, 5H), 7.43-7.49 (m, 3H), 7.63 (d, J=8.56 Hz, 2H), 7.99 (s, 1H). UPLC: 576 (M+1)

Pharmacological Activity of the Compounds of the Invention
Assessment In Vitro of Inhibitory Activity Against COX-1 and COX-2 Enzymes The murine monocyte/macrophage cell line J774 is grown in Dulbecco's modified Eagle's medium (DMEM), enriched with glutamine (2 mM), HEPES (25 mM), penicillin (100 u/mL), streptomycin (100 µg/mL), 10% of fetal bovine serum (FBS) and 1.2% of sodium pyruvate. The cells are distributed in 24-well plates at a density of $2.5 \times 10^5$ cells/mL or in culture dishes with a diameter of 10 cm ($1 \times 10^7$ cells/10 mL/dish) and kept for 2 hours at 37° C. in a $CO_2$ (5%)/$O_2$ (95%) atmosphere. Just before the experiments, the culture medium is replaced with fresh medium without FBS to avoid interference during the radio-immunological phase and the cells are stimulated as described below.

Evaluation of COX-1 Activity.

The cells are pretreated with the test compounds for 15 minutes and then incubated for 30 minutes with arachidonic acid ($15 \times 10^{-6}$ m). At the end of incubation the supernatants are collected for evaluating, by means of radio-immunological assays, the amount of $PGE_2$ produced.

Evaluation of COX-2 Activity.

The cells are stimulated, for 24 hours, with lipopolysaccharide of E. coli (10 µg/mL), to induce production of COX-2, in the absence and/or in the presence of the test compounds. The supernatants are collected for evaluating, by means of radio-immunological assays, the amount of $PGE_2$ produced.

Statistical Analysis.

In each group of experiments, wells were used in triplicate for the different treatment conditions. The results are the mean value of 3 experiments and are expressed as percentage inhibition of production of $PGE_2$ of the compounds tested relative to the control. The data were evaluated using the sigmoidal dose-response equation (variable slope) (GraphPad software). $IC_{50}$ and the 95% precision intervals were calculated with the program GraphPad Instat (GraphPad software).

Tests In Vitro for Evaluating Release of NO
In-Vitro Protocol.

The activity of the compounds was evaluated on isolated rings of thoracic aorta of normotensive male Wistar rats (250-350 g). After light anaesthesia with ether, the rats were sacrificed by cervical dislocation and exsanguination. The aortas were immediately excised, extraneous tissues were removed and the endothelial layer was removed by gently rubbing the surface with a hypodermic needle. Rings of aorta with a width of 5 mm were suspended, with a preload of 2 g, in 20-ml organ baths, containing a solution of "Tyrode" (composition of the saline solution in mM: NaCl 136.8; KCl 2.95; $CaCl_2$ 1.80; $MgSO_4$ 1.05; $NaH_2PO_4$ 0.41; $NaHCO_3$ 11.9; glucose 5.5), thermostatically controlled at 37° C. and kept in an atmosphere of $O_2$ (95%) and $CO_2$ (5%). Voltage changes were recorded by means of an isometric transducer (FTO3 Erba), connected to a microdynamometer (Buxco Electronics).

Evaluation of Release of NO.

60 minutes after preparation, removal of the endothelium was confirmed by acetylcholine (ACH) (10 µM) treatment of the vascular rings pre-contracted with KCl (20 mM). Relaxation of less than 10% of the contraction induced by KCl was considered as representative of acceptable removal of the endothelial layer, whereas organs displaying relaxation ≥10% were discarded. 40 minutes after confirmation of complete removal of the endothelium, the aortas were contracted by treatment with a single dose of KCl (20 mM) and after the contraction reached a stable plateau, increasing cumulative concentrations (with progressive increments of 3 times) of the test compounds (1 nM-10 µM) were added. It was found from preliminary experiments that the contraction induced by KCl (20 mM) remained stable in a tonic state for at least 40 minutes. The same experiments were performed in the presence of a well-known inhibitor of guanylate cyclase: ODQ 1 µM, which was incubated in aorta preparations after confirmation of removal of the endothelium.

Analysis of the results. The vasorelaxing activity was evaluated as a percentage (%) relative to the contractile tone induced by 20 mM KCl. The pharmacodynamic efficacy parameter (Emax) corresponds to the maximum vasorelaxing effect induced by the molecule tested, expressed as percentage relative to the contractile tone induced by 20 mM KCl. When the limit concentration of 10 µM (the highest concentration administered) of the test compounds has not reached the maximum effect, the efficacy parameter (Emax) corresponds to the vasorelaxing effect induced by the limit concentration (expressed as percentage relative to the contractile tone induced by 20 mM KCl). The pharmacodynamic parameter of potency of the compounds was expressed as $pIC_{50}$ calculated as the negative logarithm of the molar concentration of test compound that reduces the contractile tone induced by 20 mM KCl by half. The $pIC_{50}$ was not calculated (N.C.) for compounds that showed an Emax parameter below 50%. The parameters of efficacy and potency were expressed as mean±standard error, for 5-10 experiments. The experimental data were analysed by the program GraphPad Prism 3.0.

Evaluation of Release of Nitrites in Hepatic Homogenate

Since NO has a very short half-life (of the order of a few seconds) and is rapidly oxidized to nitrite and nitrate ions, testing for these inorganic metabolites is often used for determining whether NO has been released by NO-donors in biological samples.

In particular, some compounds of the invention, naproxcinod and sodium nitroprussiate (SNP) were incubated, at a concentration of 1 mM at 37° C. in rat liver homogenate, enriched with suitable cofactors (GSH 2.5 mM; NADH 1 mM; NADPH 1 mM). At predetermined intervals, aliquots of this mixture were taken and were added to an aqueous solution of KI (0.1 M) and $H_2SO_4$ (0.1 M). In these conditions, the nitrite ions (that have possibly formed in the homogenate from the NO released by the test compounds) are selectively and instantly reduced again to NO, which is detected and titrated amperometrically by means of an NO-selective electrode (Apollo 4000 system; ISO-NOP sensor, WPI).

Analysis of the Results

By evaluating the time-dependent increase in nitrite concentrations in the liver homogenate, it was possible to extrapolate two descriptive parameters:

Maximum Release:

maximum nitrite concentration released in the liver homogenate after 4 hours of incubation of the test compound and expressed as percentage of maximum nitrite concentration released in liver homogenate after 4 hours of incubation of the reference NO-donor SNP. SNP was selected since it is regarded as an extremely rapid NO-donor, able to release equimolar amounts of NO in a short time and by a non-enzymatic mechanism.

$T_{1/2}$:

Time (in minutes) required for an amount of nitrite to be released by the test compound equal to half its maximum release.

The results relating to inhibition of COX-2 and the NO donor property for representative compounds of the invention are shown in Tables 7-8; all the compounds stated below showed on COX-1, at 10 μM, inhibition of less than 20%, and are therefore COX-2 selective.

TABLE 7 pharmacological activity in vitro of the compounds of formula (I).

| Compound (Example) | Cyclooxygenase inhibition COX-2 IC$_{50}$ (μM) | NO release properties | |
|---|---|---|---|
| | | E$_{max}$ | pIC$_{50}$ |
| Example 1 | 0.043 | 66 ± 3 | 5.85 ± 0.04 |
| Example 2 | N.T. | 58 ± 5 | 5.46 ± 0.07 |
| Example 3 | 0.019 | 69 ± 4 | 6.48 ± 0.06 |
| Example 4 | 0.170 | 77 ± 2 | 6.75 ± 0.05 |
| Example 5 | N.T. | 64.9 ± 1.4 | 6.34 ± 0.06 |
| Example 8 | 0.007 | 82 ± 1 | 6.79 ± 0.11 |
| Example 9 | 0.002 | 41 ± 11 | N.C. |
| Example 10 | 0.027 | 41 ± 8 | N.C. |
| Example 11 | N.T. | 40 ± 8 | N.C. |
| Example 12 | 0.069 | 57 ± 14 | 5.40 ± 0.18 |
| Example 13 | 0.55 | N.T. | N.T. |
| Example 14 | 0.22 | 55 ± 15 | 5.30 ± 0.02 |
| Example 15 | N.T. | 57 ± 6 | 5.95 ± 0.13 |
| Example 16 | 0.74 | 80 ± 7 | 5.95 ± 0.06 |
| Example 18 | 0.82 | 84 ± 2 | 5.66 ± 0.03 |
| Example 20 | 1.0 | 93 ± 1 | 5.81 ± 0.03 |
| Example 23 | 0.24 | 68 ± 6 | 5.31 ± 0.05 |
| Example 29 | 0.31 | S.E | S.E |
| Example 30 | 0.14 | S.E | S.E |
| Example 32 | 1.6 | 42 ± 9 | N.C. |
| Example 33 | N.T. | 23 ± 2 | N.C. |

TABLE 7-continued pharmacological activity in vitro of the compounds of formula (I).

| Compound (Example) | Cyclooxygenase inhibition COX-2 IC$_{50}$ (μM) | NO release properties | |
|---|---|---|---|
| | | E$_{max}$ | pIC$_{50}$ |
| Example 23 | 0.24 | 68 ± 6 | 5.31 ± 0.05 |
| Example 30 | 0.14 | S.E | S.E |
| Example 32 | 1.6 | 42 ± 9 | N.C. |
| Example 33 | N.T. | 23 ± 2 | N.C. |
| Example 36 | 0.017 | 65 | 5.22 ± 0.03 |
| Example 37 | 0.014 | 49 ± 3 | N.C. |
| Example 38 | 0.028 | 60 ± 4 | 5.32 ± 0.05 |
| Example 39 | 0.92 | 43 ± 6 | N.C. |
| Example 40 | 0.015 | 48.2 ± 0.5 | N.C. |
| Example 41 | 0.19 | S.E. | N.C. |
| Example 42 | 0.43 | S.E. | N.C. |

N.T.: Not tested; N.C.: Not Calculated (see above)
S.E: Scarcely Effective: it is not possible to detect NO release comparable to the other compounds mentioned here.

TABLE 8 pharmacological activity in vitro of the compounds of formula (II). All the compounds of formula (II) stated below showed inhibition below 20% on COX-1, at 10 μM, and are therefore COX-2 selective.

| Compound (Example) | Cyclooxygenase inhibition COX-2 IC$_{50}$ (μM) | Compound (Example) | Cyclooxygenase inhibition COX-2 IC$_{50}$ (μM) |
|---|---|---|---|
| Example 1-II | 0.027 | Example 2-II | 0.089 |
| Example 3-II | 0.085 | Example 4-II | 1.1 |
| Example 5-II | 0.085 | Example 8-II | 0.023 |
| Example 9-II | 0.7 | Example 10-II | 0.26 |
| Example 12-II | 0.11 | Example 13-II | 1.1 |
| Example 14-II | 0.055 | Example 23-II | 0.30 |
| Example 24-II | 0.29 | Example 26-II | 0.068 |
| Example 27-II | 0.014 | Example 29-II | 0.16 |
| Example 30-II | 0.057 | Example 32-II | 0.086 |
| Example 36-II | 0.027 | Example 37-II | 0.089 |
| Example 38-II | 0.046 | Example 39-II | 0.42 |
| Example 41-II | 0.94 | Example 42-II | 1.5 |

Figure 2:
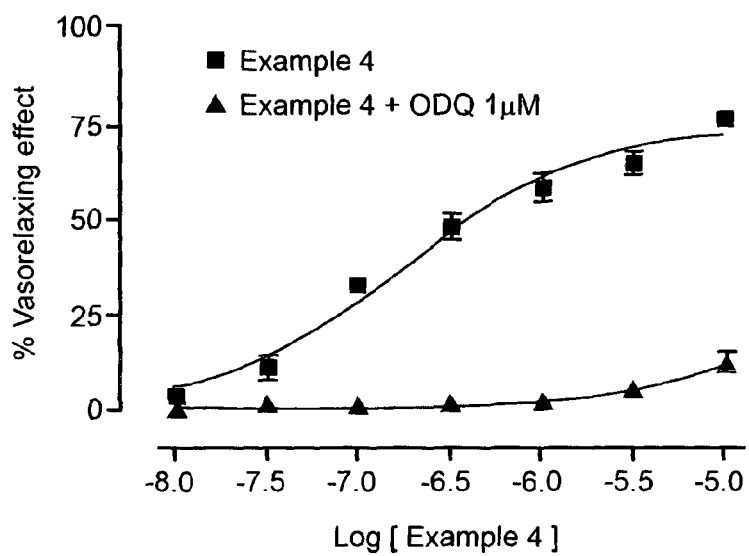
FIG. 2 shows the concentration-vasorelaxing response curves for the compound of Example 4 in the absence or presence of ODQ.
Figure 3:
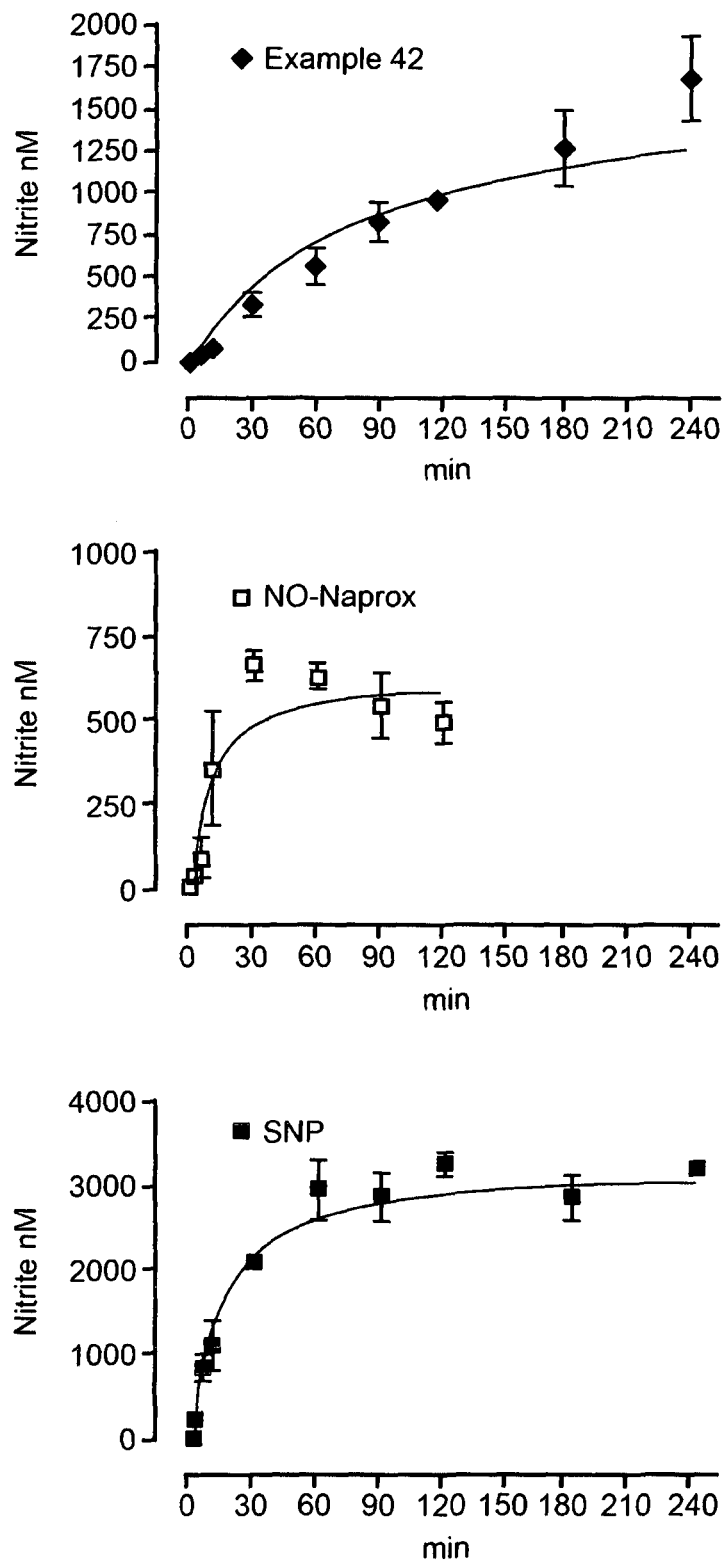
FIG. 3 shows the time-dependent increase of nitrite concentration after incubation of the compound of Example 42, naproxcinod or SNP in rat liver homogenate.

The data presented in Tables 1-2 show that the nitro esters of the invention are already COX-2 inhibitors per se and do not require, for performing said activity, conversion to a compound of formula (II) or of formula (III) as in the case of known CINODs such as naproxcinod and NO-flurbiprofen. Moreover, many nitro esters of formula (I) prove to be more potent COX-2 inhibitors than the respective alcohols of formula (II), for example those given in examples: 3, 4, 9, 10, 12, 37, 38, 41, 42. The relationship between potency in inhibition of COX-2 and the structure of the compound of formula (I)/(II) is connected with various aspects, such as the combination of the pattern of substitution of the phenyl in −1, the length and the type of chain bearing the nitro ester function. For example, for esters (I-a) we may compare examples 9, 10 with the corresponding examples 13 and 14, where the use of the chain with four carbon atoms present in naproxcinod leads to less significant results. In other cases a different substitution of the phenyl in −1 gives rise to esters (I-a) characterized by potency on COX-2 that is less dependent on chain length, as can be seen in examples: 3, 8, 12. A close relationship between potency on COX-2 and chain length is also present in the compounds of formula (I-c), where in this case shorter chains give the best effects, as follows on comparing examples 37 vs. 41, 38 vs. 42. The NO-donor properties are also greatly influenced by the pattern of substitution of the phenyl in −1, and by the length and type of chain bearing the nitro ester. With regard to the effect of substitution of the phenyl, examples 8 vs. 9 and 34 vs. 37 may be considered, with respect to chain length examples 1 vs. 6 and 34 vs. 40, with respect to type of chain by comparing examples 29 vs. 23 and vs. 32. Finally, it is known that to obtain at the same time excellent COX-2 inhibition and suitable NO-donor properties (such as for examples 3, 4, 12, 34, 37, 38) it is not sufficient to combine a nitrooxy-ester function with a good COX-2 inhibitor, still less can it be deduced from what is known. With regard to greater detail about NO releasing activity, most of the compounds proved to be adequately active at vascular level, displaying relaxing effects on the vascular smooth muscles, with variable parameters of efficacy and potency (Table 7), and as an example, the concentration-response curve relative to the vasorelaxing effect of the compound in example 4 is shown in FIG. 2. For correlating the pharmacological effects of the compounds tested with the release of NO, the activity of the compounds of formula (I) was also tested in the presence of ODQ (1H-[1,2,4]oxadiazole[4,3-a]quinoxalin-1-one) at a concentration of 1 M. ODQ is in fact an inhibitor of guanylate cyclase, able to prevent activation of this enzyme and consequent increase in levels of intracellular cGMP, responsible for the pharmacological effects of NO on the vascular smooth muscles. The vasodilator effects of all the compounds of formula (I) were antagonized by ODQ (with the sole exception of three derivates for which a residual vasorelaxing activity is not antagonized), this experimental finding indicates that the biological effect is mediated by the release of NO by the nitrooxy-ester function, with consequent activation of guanylate cyclase by NO and consequent relaxation of the smooth muscles. A similar effect was shown by naproxcinod, which exhibited partial vasorelaxing properties (Emax=62±4) and levels of potency of the order of 10 mM (pIC50=5.28±0.01). Only the compounds of example 14, example 18 and example 20 showed vasorelaxing action that was not fully antagonized by ODQ, which can therefore be attributed to an NO-independent mechanism of action, which moreover has already been described (Klein et al. Cardiovasc Res. 2007; 75: 390-397) for drugs such as celecoxib. The NO-releasing properties of the compounds of the invention were confirmed by the data obtained after incubation of some representative compounds in rat liver homogenate (Table 9; FIGS. 2-3). In this biological substrate, intrinsically equipped with the enzymatic machinery necessary for converting the nitrooxy-ester function to NO and suitably enriched with the necessary cofactors (GSH, NADH, NADPH), incubation of some of the compounds of the invention led to time-dependent production of nitrite, with a course compatible with the profile of slow NO-donors. In this experimental model, incubation of naproxcinod led to a very rapid, slight release of nitrites, with a course that does not easily relate to an NO-donor profile similar to the compounds of the invention, which are characterized by a profile that can be modulated more readily and is compatible with the desired action.

TABLE 9

Values of "Maximum release" and of T1/2, relating to nitrite production in liver homogenate by representative compounds.

| Compound | Maximum release (%) | T ½ |
|---|---|---|
| SNP | 100 | 13.5 ± 1.9 |
| Nicorandil | 18 ± 2 | 27.8 ± 8.2 |
| Example 2 | 26 ± 7 | 68.7 ± 12.5 |
| Example 37 | 25 ± 3 | 42.8 ± 6.9 |

TABLE 9-continued

Values of "Maximum release" and of T1/2, relating to nitrite production in liver homogenate by representative compounds.

| Compound | Maximum release (%) | T ½ |
|---|---|---|
| Example 38 | 28 ± 3 | 60.7 ± 8.7 |
| Example 39 | 30 ± 1 | 68.2 ± 8.5 |
| Example 42 | 52 ± 8 | 84.4 ± 11.9 |
| NO-Naproxen | 20 ± 1* | 8.6 ± 2.9 |

*the "maximum release" had already been reached at 30 min (see FIG. 3) SNP: sodium nitroprussiate.

Evaluation In Vivo of Anti-Inflammatory and Analgesic Activity

Male Swiss albino mice (23-25 g) and Wistar rats (150-200 g) were used.

Abdominal Constriction Test.

The antinociceptive activity was determined by the mouse abdominal contraction test using acetic acid (0.6%), which induces writhing, according to Koster's method (Fed. Proc., 1959, 18, 412-418). The number of stretching movements was counted for 10 minutes, starting 5 minutes after injection of acetic acid. The results relating to analgesic activity in the abdominal constriction test with representative compounds of the invention are shown in Table 10.

Carrageenan-Induced Oedema Test.

The nociceptive threshold in the rat was determined with an analgesiometer, as described by Leighton et al. (Br. J. Pharmacol., 1988, 93, 553-560), the pressure was measured before the treatment and after 30 and 60 min. To reproduce the inflammatory state in the rat, carrageenan was administered i.p. (0.1 ml, 1%) 4 h before the test.

Volume of Oedema Test.

The rat paw volumes were measured using a pletismometer. Four hours after injecting carrageenan 1.0% (0.1 ml injection), the volume of the right hind-paw was measured and compared with that of controls treated with a saline/carrageenan solution. The rats were administered the test compounds 3.5 hours after the carrageenan. The results are given as paw volume expressed in ml. The results relating to the analgesic and anti-oedemic activity in the carrageenan test for some representative compounds of the invention are shown in Table 11.

TABLE 10

Results obtained with representative compounds in the test of abdominal constriction induced by acetic acid

| Compound administered | Dose mg/kg | N writhes |
|---|---|---|
| CMC | — | 30.7 ± 2.3 |
| Example 3 | 20 | 17.1 ± 2.3 |
| Example 3 | 40 | 9.4 ± 2.5 |
| Example 4 | 40 | 17.7 ± 2.3 |
| Example 8 | 20 | 16.9 ± 2.4 |
| Example 9 | 20 | 18.4 ± 3.1 |
| Example 12 | 40 | 25.1 ± 2.3 |
| Example 13-II | 40 | 14.7 ± 2.5 |
| Example 16 | 40 | 24.9 ± 3.0 |
| Example 18 | 3 | 26.9 ± 2.6 |
| Example 18 | 10 | 21.3 ± 2.5 |
| Example 18 | 20 | 18.1 ± 3.0 |
| Example 18 | 40 | 13.5 ± 2.8 |
| Example 20 | 40 | 19.8 ± 2.4 |
| Example 32 | 10 | 22.8 ± 3.0 |
| Example 32 | 20 | 14.6 ± 2.7 |
| Example 37 | 10 | 19.1 ± 2.7 |
| Example 37 | 20 | 15.2 ± 3.3 |
| Example 37-II | 40 | 18.2 ± 3.1 |

TABLE 10-continued

Results obtained with representative compounds in the test of abdominal constriction induced by acetic acid

| Compound administered | Dose mg/kg | N writhes |
|---|---|---|
| Example 38 | 40 | 25.3 ± 3.6 |
| Example 38-II | 20 | 26.8 ± 3.2 |
| Example 38-II | 40 | 17.3 ± 3.5 |
| Example 39 | 20 | 26.3 ± 3.4 |
| Example 39-II | 20 | 24.8 ± 3.0 |

The test was carried out using 10 animals in the treated group and 20 in the control group (CMC); all the compounds were administered per os with the exception of the compound of Example 8, which was administered i.p.

Comparison of the data in vitro given in Tables 7-8 with the data in vivo in Table 10 shows that for purposes of pharmacological activity in vivo, for the compounds of the invention, not only the potency in vitro is important, but also the characteristics of solubility and of bioavailability, as can be seen on comparing for example the respective data relating to example 18 with other compounds in vitro that are much more potent, such as those in examples 3 and 37.

TABLE 11

Results obtained with representative compounds and standards in the carrageenan test

| Compound administered | Dose (mg/kg) | Weight supported (g) | | | Oedema Volume (mL) |
|---|---|---|---|---|---|
| | | Before treatment | After treatment | | |
| | | | 30 min | 60 min | |
| CMC | — | 63.2 ± 2.8 | 61.6 ± 2.8 | 62.7 ± 2.8 | 1.36 ± 0.04 |
| Carrageenan | — | 31.2 ± 3.1 | 33.4 ± 3.5 | 22.9 ± 3.7 | 2.59 ± 0.02 |
| Example 3 | 40 | 32.6 ± 2.7 | 54.1 ± 3.7 | 38.7 ± 3.1 | 2.17 ± 0.08 |
| Example 37 | 10 | 34.7 ± 2.7 | 55.1 ± 4.7 | 52.6 ± 4.0 | 1.87 ± 0.07 |
| Example 37-II | 20 | 32.5 ± 3.4 | 46.8 ± 3.7 | 38.7 ± 3.3 | 2.08 ± 0.07 |
| Example 41 | 20 | 30.9 ± 2.8 | 49.2 ± 3.7 | 50.7 ± 3.8 | 1.85 ± 0.08 |
| Celecoxib | 10 | 30.9 ± 2.6 | 52.9 ± 3.1 | 48.3 ± 3.4 | 1.91 ± 0.04 |
| Naproxcinod | 10 | 33.5 ± 3.7 | 47.9 ± 3.5 | 46.2 ± 3.8 | 1.95 ± 0.07 |
| Naproxcinod | 30 | 32.7 ± 3.8 | 48.2 ± 2.8 | 43.9 ± 3.7 | 1.88 ± 0.07 |

The test was performed using 6 animals per group, all the compounds were administered per os, 30 min before the test. The carrageenan is administered 2 h before the test. The compound of Example 41 was found to be effective even after 120 min (45.2±4.1).

TABLE 12

Results obtained with representative compounds in the test of chronic pain from MIA-induced osteoarthritis.

| Compound administered | Weight supported (g) | | | | |
|---|---|---|---|---|---|
| | Before treatment | After treatment | | | |
| | | 30 min | 4 h | 24 h | 36 h |
| CMC | 61.2 ± 3.0 | 58.7 ± 2.9 | 62.6 ± 3.1 | 63.4 ± 3.3 | 59.6 ± 3.2 |
| MIA | 32.6 ± 2.9 | 30.4 ± 3.1 | 33.5 ± 2.9 | 31.2 ± 3.2 | 33.7 ± 2.9 |
| Example 37 | 34.6 ± 3.1 | 45.1 ± 3.7 | 39.1 ± 3.5 | 33.8 ± 3.7 | N.D. |
| Example 37-II | 33.5 ± 2.6 | 51.2 ± 3.9 | 50.3 ± 3.8 | 48.1 ± 3.3 | 47.4 ± 3.3 |

The compounds are administered per os at a dose of 20 mg/kg twice daily for 14 days.

Monosodium iodoacetate (MIA), 2 mg in 25 μL is injected in the left knee of anaesthetized rats, the test is carried out according to the literature. Each experiment represents the mean value for 5 animals.

N.D.: Not Determined.

The invention claimed is:
1. A compound according to Formula (I), a solvate thereof or pharmaceutically acceptable salt:

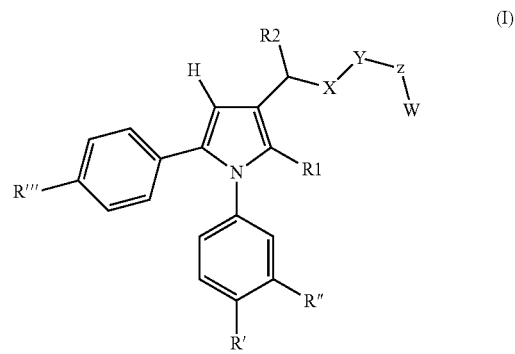

(I)

wherein:
the substituent in position 1 of the pyrrole ring is a phenyl, substituted in the meta and para positions with groups R' and R" selected independently from: hydrogen (—H), fluorine (—F), chlorine (—Cl), bromine (—Br), methyl (—CH$_3$), trifluoromethyl (—CF$_3$), methoxy (—OCH$_3$), thiomethyl (—SCH$_3$);
the substituent R1 is selected independently from the following groups: methyl (—CH$_3$), ethyl (—C$_2$H$_5$), trifluoromethyl (—CF$_3$), hydroxymethyl (—CH$_2$OH), methoxymethyl (—CH$_2$OCH$_3$);
the substituent in position −3 of the pyrrole ring is a chain, where the groups X, Y, Z, W and R2 have the following meanings:
X is selected from the groups: carbonyl —(C=O)—, —(CHR$_3$);
Y is selected from an oxygen atom (—O—) or the group —NR$_3$;
Z is selected from a carbonyl —(C=O)—, a group —(CHR$_3$)—, a group [—CH(COOH)—], or a group —(NR$_3$);
W is a saturated aliphatic chain with 1 to 3 carbon atoms, linear or branched, substituted with one or two nitro ester groups (—O—NO$_2$);
R2 is selected independently from the groups: hydrogen (—H), hydroxyl (—OH), methoxy (—OCH$_3$), or amino (—NHR$_3$);
wherein R$_3$ can be identical or different and is selected independently from: hydrogen (—H), methyl (—CH$_3$), ethyl (—CH$_2$CH$_3$), isopropyl [—CH$_2$(CH$_3$)$_2$];
the group R'" is selected independently from: methylsulphonyl (—SO$_2$Me) and sulphonamido (—SO$_2$NH$_2$);
provided that:
when X is a C=O group and Y is an oxygen atom (—O—), Z is not a carbonyl group (C=O);
when X is a —(CHR$_3$)— group, Y is an oxygen atom (—O—);
wherein the compound of Formula (I) can be an enantiomer in the (R) or (S) form, in racemic mixtures, mixtures enriched with said enantiomers or diastereomers of the compounds of Formula (I) where each chiral centre can be independently in the (R) or (S) configuration, the respective diastereomeric mixtures (1:1) or the enriched mixtures.

2. The compound of claim 1 wherein group X of Formula (I) is a carbonyl —(C=O)—, and group Y is an oxygen atom (—O—):

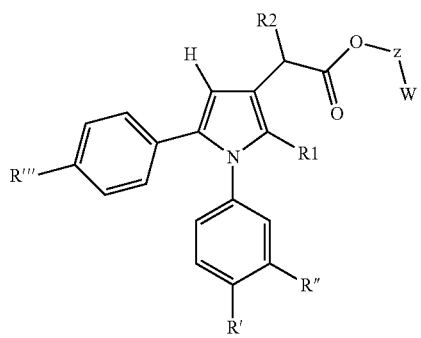

wherein the compound of Formula (I) is an ester of Formula (I-a), and wherein group Z is a group —(CHR₃).

3. The compound of claim 1 wherein group X of Formula (I) is a carbonyl (C=O) and group Y is a group —NR₃—:

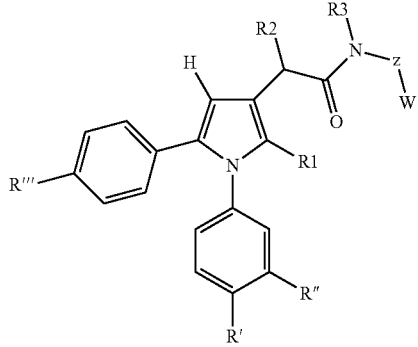

wherein the compound of Formula (I) is an amide of Formula (I-b), and wherein group Z is a group —(CHR₃)— or a [—CH(COOH)—] group.

4. The compound of claim 1 wherein group X of Formula (I) is a group —(CHR₃)— and group Y is an oxygen atom (—O—):

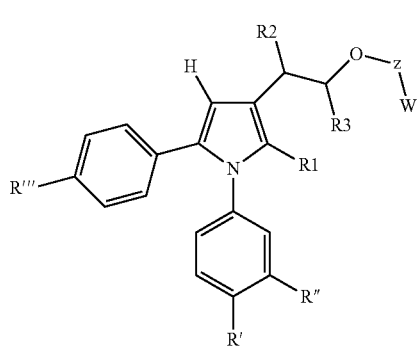

wherein the compound of Formula (I) is an ether of Formula (I-c), and wherein group Z is a group —(CHR₃).

5. The compound of claim 1 wherein X of Formula (I) is a group —(CHR₃)—, group Y is an oxygen atom (—O—), and group Z is a carbonyl group (C=O):

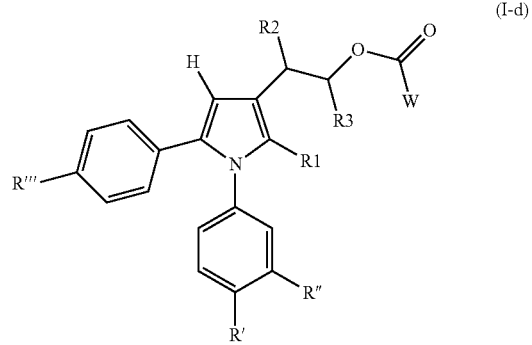

wherein the compound of Formula (I) is an ester of Formula (I-d).

6. The compound of claim 1 wherein group X of Formula (I) is a group —(CHR₃)—, group Y is a group —NR₃— and group Z is a carbonyl group (C=O):

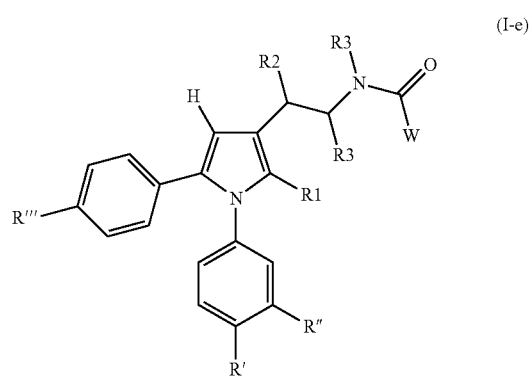

wherein the compound of Formula (I) is an amide of Formula (I-e).

7. A pharmaceutical formulation comprising a compound of Formula (I) or pharmaceutically acceptable salts or solvates thereof and a pharmaceutically acceptable vehicle.

8. A method for the treatment or amelioration of a COX-2 mediated disorder comprising administering to a subject in need thereof the compound of Formula (I) or a solvate or salt thereof.

9. The method of claim 8, where the COX-2 mediated disorder is selected from the group consisting of: inflammatory disorders of the respiratory tract, inflammatory disorders of the urogenital tract, fibromyalgia, lupus erythematosus, psoriasis and gastrointestinal inflammations.

10. A method for the treatment or amelioration of pain comprising administering to a subject in need thereof a pharmaceutically effective amount of a compound of formula (I), or a solvate or salt thereof.

11. The method of claim 10, further comprising administering an analgesic.

12. The method of claim 10, wherein the pain is due, at least in part, to a condition selected from the group consisting of: dental pain, postoperative pain, neuropathic pain, and pain induced by cancer.

13. The method of claim 11, wherein the pain is due, at least in part, to a condition selected from the group consisting of: dental pain, postoperative pain, neuropathic pain, and pain induced by cancer.

* * * * *